US009463187B2

(12) United States Patent  (10) Patent No.: US 9,463,187 B2
Bar-Or et al.  (45) Date of Patent: Oct. 11, 2016

(54) METHYLPHENIDATE DERIVATIVES AND USES OF THEM

(75) Inventors: David Bar-Or, Englewood, CO (US); Nagaraja K. R. Rao, Cardiff (GB)

(73) Assignee: Ampio Pharmaceuticals, Inc., Englewood, CO (US)

(*) Notice: Subject to any disclaimer, the term of this patent is extended or adjusted under 35 U.S.C. 154(b) by 0 days.

(21) Appl. No.: 13/288,179

(22) Filed: Nov. 3, 2011

(65) Prior Publication Data

US 2012/0101129 A1  Apr. 26, 2012

Related U.S. Application Data

(60) Division of application No. 12/260,964, filed on Oct. 29, 2008, now Pat. No. 8,076,485, which is a continuation of application No. 11/336,029, filed on Jan. 20, 2006, now abandoned.

(60) Provisional application No. 60/663,006, filed on Mar. 18, 2005, provisional application No. 60/645,778, filed on Jan. 20, 2005.

(51) Int. Cl.
   A61K 31/445  (2006.01)

(52) U.S. Cl.
   CPC .................................. *A61K 31/445* (2013.01)

(58) Field of Classification Search
   CPC .................................................. A61K 31/445
   See application file for complete search history.

(56) References Cited

U.S. PATENT DOCUMENTS

| | | | |
|---|---|---|---|
| 2,507,631 A | 5/1950 | Hartmann et al. | |
| 2,957,880 A | 10/1960 | Rometsch et al. | |
| 5,407,926 A | 4/1995 | Clark | |
| 5,658,955 A | 8/1997 | Hitzig | |
| 5,859,249 A | 1/1999 | Seido et al. | |
| 5,908,850 A | 6/1999 | Zeitlin et al. | |
| 6,025,502 A | 2/2000 | Winklter et al. | |
| 6,060,463 A | 5/2000 | Freeman | |
| 6,127,385 A | 10/2000 | Midha et al. | |
| 6,210,705 B1 | 4/2001 | Mantelle et al. | |
| 6,395,752 B1 | 5/2002 | Midha et al. | |
| 6,486,177 B2 | 11/2002 | Zeldis et al. | |
| 6,555,543 B2 | 4/2003 | Bar-Or et al. | |
| 7,267,949 B2 | 9/2007 | Richards et al. | |
| 8,076,485 B2 | 12/2011 | Bar-Or et al. | |
| 2002/0132793 A1 | 9/2002 | Epstein et al. | |
| 2005/0101582 A1 | 5/2005 | Lyons et al. | |
| 2005/0192290 A1 | 9/2005 | Melamed | |
| 2006/0183773 A1 | 8/2006 | Bar-Or et al. | |
| 2006/0189655 A1 | 8/2006 | Bar-Or et al. | |

FOREIGN PATENT DOCUMENTS

| | | |
|---|---|---|
| GB | 851972 | 10/1960 |
| WO | WO 97/48685 | 12/1997 |
| WO | WO 99/16439 | 4/1999 |
| WO | WO 99/36403 | 7/1999 |
| WO | WO 00/59880 | 10/2000 |
| WO | WO 00/74680 | 12/2000 |
| WO | WO 01/30337 | 5/2001 |
| WO | WO 01/68053 | 9/2001 |
| WO | WO 03/037247 | 5/2003 |
| WO | WO 2004/043480 | 5/2004 |
| WO | WO 2004/058289 | 7/2004 |
| WO | WO 2005/000203 | 1/2005 |

OTHER PUBLICATIONS

Auerbach "Angiogenesis Assays: A Critical Overview" Clinical Chemistry 49:132-40 (2003).*
Trisha Gura "Cancer Models: Systems for Identifying New Drugs Are Often Faulty" Science Nov. 7, 1997: vol. 278. No. 5340, pp. 1041-1042.*
Johnson, et. al. "Relationships between drug activity in NCI preclinical in vitro and in vivo models and early clinical trials." British Journal of Cancer 2001, 84, 1424-1431.*
Damia "Contemporary pre-clinical development of anticancer agents—What are the optimal preclinical models?" European Journal of Cancer 2009, 45, 2768-2781.*
Sharma "Cell line-based platforms to evaluate the therapeutic efficacy of candidate anticancer agents" Nature Reviews Cancer Apr. 2010, vol. 10, 241-253.*
Ocana, A. "Preclinical development of molecular targeted agents for cancer" Nat. Rev. Clin. Oncol. 2011, 8, 200-209.*
Online "http://dtp.nci.nih.gov/services/nci60data/onedose/759278" accessed Apr. 9, 2015.*
Online "http://dtp.nci.nih.gov/branches/btb/onedose_interp.html" accessed Apr. 9, 2015.*
Online "http://dtp.nci.nih.gov/services/nci60data/onedose/125973" accessed Apr. 9, 2015.*
Online "http://dtp.nci.nih.gov/docs/misc/common_files/submit_compounds.html" accessed Apr. 9, 2015.*
Wilhelm "Regorafenib (Bay 73/4506): a new oral multikinase inhibitor of angiogenic, stromal and oncogenic receptor tyrosine kinases with potent preclinical antitumor activity" Int. J. Cancer 2011, 129, 245-255.*

(Continued)

*Primary Examiner* — David K O'Dell
(74) *Attorney, Agent, or Firm* — Sheridan Ross P.C.

(57) ABSTRACT

The present invention provides methods of using compounds of formula I:

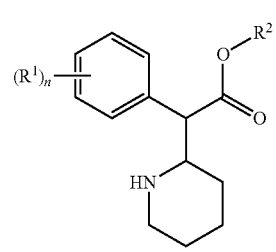

and salts and prodrugs thereof, wherein n, $R^1$ and $R^2$ are defined herein. The invention also provides certain novel compounds of formula I and pharmaceutical compositions comprising them.

3 Claims, 27 Drawing Sheets

(56) References Cited

OTHER PUBLICATIONS

"inteliHealth: Multiple Sclerosis," available on the World Wide Web at http://www.intelihealth.com/IH/iht1H/WSIHW000/9339/10372.html, downloaded on May 7, 2006.
Auci et al. "Methylphenidate and the immune system," J Am Acad Child Adolcesc Psychiatry 1997, 36(8): 1015-1016.
Breitbart et al., "A randomized, double-blind, placebo-controlled trial of psychostimulants for the treatment of fatigue in ambulatory patients with human immunodeficiency virus disease", Arch Inern Med 2001, 161(3): 411-20, Abstract only, PubMed ID: 11176767.
Bruera et al., Patient-Controlled Methylphenidate for the Management of Fatigue in Patients With Advanced Cancer: A Preliminary Report, Journal of Oncology, vol. 21, No. 23, Dec. 2003, pp. 4439-4443.
Challman et al., "Methylphenidate: its pharmacology and uses", Mayo Clin Proc 2000, 75: 711-721.
Cruse et al., Illustrated Dictionary of Immunology (2nd edition, Taylor & Francis Group, CRC Press LLC, 2003), p. 475.
Davies et al., "Synthesis of Methylphenidate Analogues and their Binding Affinities at Dopamine and Serotonin Transport Sites", Bioorganic & Medicinal Chemistry Letters, 2004, vol. 14, pp. 1799-1802.
Deutsch et al., "Synthesis and pharmacology of potential cocaine antagonists. 2. Structure—activity relationship studies of aromatic ring-substituted methylphenidate analogs,", J Med Chem 1996, vol. 39, pp. 1201-1209.
Meltzer et al., "The synthesis of bivalent 2β-carbomethoxy-3β-(3,4-dichlorophenyl)-8- heterobicyclo[3.2.1]octanes as probes for proximal binding sites on the dopamine and serotonin transporters," Bioorganic and Medicinal Chemistry, Feb. 15, 2008, vol. 16, pp. 1832-1841.
Martin et al., "Do Structurally Similar Molecules Have Similar Biological Activity?" Journal of Medicinal Chemistry, 2002, vol. 45, pp. 4350-4358.
Dorwald, Side Reactions in Organic Synthesis:A Guide to Successful Synthesis Design, Wiley-VCH, copyright May 5, 2005, p. IX of Preface, pp. 1-15.
Dunnick et al., "Decreased incidence of spontaneous mammary gland neoplasms in female F344 rats treated with amphetamine, methylphenidate, or codence", Cancer Ltt 1996, 102(1-2): 77-83; Erratum in Cancer Lett 1996 105(1): 121-122, Abstract only, PubMed ID:8603383.
Dunnick et al., "Decreased incidence of spontaneous mammary gland neoplasms in female F344 rats treated with amphetamine, methylphenidate, or codeine," Cancer Letters, 1996, vol. 102(1-2), pp. 77-83.
Dunnick et al., "Experimental studies on long-term effects of methylphenidate hydrochloride," Toxicology 1995, 103(2): 77-84 Abstract only, PubMed ID: 8545847.
Gatley et al., "Affinities of Methylphenidate derivative for dopamine, norepinephrine and seotonin transporters," Life Sciences 1996, 58(12): 231-239.
Happe, "Excessive daytime sleepiness and sleep disturbances in patients with neurological diseases: epidemiology and management", Drugs 2003, 63(24): 2725-2737 Abstract only, PubMed ID 14664652.
Haran "Beyond just tired: figuring out MS-related fatigue", available on the Worldwide Web at http://www.understandingsms.com/ms/articles/ms_beyondtired.asp, downloaded on May 7, 2006.
Krim, Lori, Thesis (Ph.D. in Chemistry) (2001), University of Pennsylvania, Chemistry Library Reading Room (Call No. QD001 2001.K92), University Microfilms Order No. 3031684, ISBN 0493-44179-4, 762 pages.
Krupp et al., "Fatigue in multiple sclerosis," Curr Neurol Neurosci Rep, 2001, vol. 1(3), pp. 294-298.
Leonard et al., "Methylphenidate: a review of its neuropharmacological, neuropsycological and adverse clinical effects," Human Psychopharmacol Clin Exp 2004, 19:151-180.
Natl Toxicol Program Tech Rep Ser, "NTP toxicology and carcinogenesis studies of methylphenidate hydrochloride (CAS No. 298-59-9) in F344/N rats and B6C3F1 mice (feed studies)," 1995, 439:1-299 Abstract only, PubMed ID 12595924.
Pan et al., "Binding of bromine-substituted analogs of methylphenidate to monoamine transporters," Euro J Pharmacol 1994, 264:177-182.
Patrick et al., "Synthesis and pharmacology of hydroxylated metabolites of methylphenidate," J Med Chem 1981, 24(1): 1237-1240.
Ritalin, available on the World Wide Web at http://ms.about.com/od/treatment/a/Ritalin.htm, downloaded on May 7, 2006.
Rozans et al., "Palliative Uses of Methylphenidate in Pateints With Cancer: A Review", J. Clin. Oncology, Jan. 1, 2002, vol. 20, No. 1, pp. 335-339.
Teo et al., "D-methylphenidate is non-genotoxic in in vitro and in vivo assays," Mutat Res 2003, 537(1): 67-79 Abstract only, PubMed ID 12742508.
Thai et al, "Asymmetric synthesis and pharmacology of methylphenidate and its para-substituted derivatives", J Med Chem 1998, 41: 591-601.
Thai et al., "Comparative pharmacokinetics and tissue distribution of the d-enantiomers of para-substituted methylphenidate analogs," Drug Metabolism and Disposition 1999, 27(6): 645-650.
Vargas et al., "Neuroglial activation and neuroinflammation in the brain of patients with autism", Annal Neurol, Early View (Articles online in advance of print), Wiley InterScience::Article Full Text HTML, available on the World Wide Web at http://www3.interscience.wile.com/cgi-bin/fulltext/109793289/main.html,ftx_abs, downloaded on Nov. 15, 2004.
Vigano et al., "Methylphenidate for the management of somatization in terminal cancer patients," J Pain Symptom Manage 1995, 10(2): 167-170 Abstract only, PubMed ID 7730689.
Wayment et al., "Effects on methylphenidate analogues on phenethylamine substrates for the striatal dopamine transporter: potential as amphetamine antagonists?" J Neurochem 1999, 72(3): 1266-1274 Abstract only, PubMed ID 10037500.
Search Report for International (PCT) Patent Application No. PCT/US2006/002008, mailed Sep. 21, 2006.
Written Opinion for International (PCT) Patent Application No. PCT/US2006/002008, mailed Sep. 21, 2006.
International Preliminary Report on Patentability for International (PCT) Patent Application No. PCT/US2006/002008, mailed Aug. 2, 2007.
Glavin et al. "Effects of Dopamine Agonists and Antagonists on Gastric Acid Secretion and Stress Responses in Rats." Life Sciences, 1987, vol. 41 No. 11, p. 1397-1408.
Marek "Psychotropic drugs and inflammatory reaction (III): Effects of single and repeated administration of psychotropic drugs on the bentonite oedema of the rat paw."Activas Nervosa Superior, 1985, vol. 27, No. 1, p. 21-22.
Schiller et al. "Methlyphenidate Hydrochloride (Ritalin) in Obstructive Pulmonary Disease." Jour Allergy, 1958, vol. 29, No. 2, p. 160-164.
"A to Z List of Cancers: Y," National Cancer Institute, 2014 [retrieved on Jan. 13, 2014], 1 pages, Retrieved from: www.cancer.gov/cancertopics/types/alphalist/y.
Beger et al, "Treatment of Pancreatic Cancer: Challenge of the Facts," World Journal of Surgery, 2003, vol. 27, No. 10, pp. 1075-1084.
Braun-Moscovici et al., "Stem cell therapy in scleroderma," Current Opinion in Rheumatology, 2002, vol. 14, Iss.6, pp. 711-716.
Chabner et al., "Chemotherapy and the war on cancer," Nature Reviews Cancer, 2005, vol. 5, Iss. 1, pp. 65-72.
Chou et al., "Structure—Activity Relationships of Substituted Benzothiophene-anthranilamide Factor Xa Inhibitors," Bioorganic & Medicinal Chemistry Letters, 2003, vol. 13. Iss. 3, pp. 507-511.
Cole et al., "Potential Tumor-Selective Nitroimidazolylmethyluracil Prodrug Derivatives: Inhibitors of the Angiogenic Enzyme Thymidine Phosphorylase," Journal of Medicinal Chemistry, 2003, vol. 46, Iss. 2, pp. 207-209.
Fisher et al., "The epidemiology of non-Hodgkin's lymphoma," Oncogene, 2004, vol. 23, Iss. 38, pp. 6524-6534.
Leaf, "The War on Cancer," Fortune, Mar. 9, 2004, 13 pages.

(56) References Cited

OTHER PUBLICATIONS

Schwartzbaum et al., "Epidemiology and molecular pathology of glioma," Nature Clinical Practice Neurology, 2006, vol. 2, No. 9, pp. 494-503.

Swigris et al., "Idiopathic Pulmonary Fibrosis: Challenges and Opportunities for the Clinician and Investigator," Chest, 2005, vol. 127, Iss. 1, pp. 275-283.

Zhu et al., "Phosphate Prodrugs of PD154075," Bioorganic & Medicinal Chemistry Letters, 2000, vol. 10, Iss. 10, pp. 1121-1124.

* cited by examiner

R Group

Methyl (1)
Ethyl
n-Propyl
i-Propyl
n-Butyl
i-Butyl
sec-Butyl
n-Amyl
Cyclopentyl
Cyclohexyl
Benzyl
2-Methoxyethyl
2-Chloroethyl

| Compound | X | Position |
|---|---|---|
| 6 | H | |
| 6a | Br | 2 |
| 6b | Br | 3 |
| 6c | Br | 4 |
| 6d | Cl | 2 |
| 6e | Cl | 3 |
| 6f | Cl | 4 |
| 6g | di-Cl | 3,4 |
| 6h | $NO_2$ | 4 |
| 6i | Me | 3 |
| 6j | Me | 4 |
| 6k | t-Bu | 4 |
| 6l | $NH_2$·HCl | 3 |
| 6m | OMe | 2 |
| 6n | OMe | 3 |
| 6o | OMe | 4 |

Preparation of 9 :

Preparation of 10 :

Preparation of 6:

Preparation of 63b:

Preparation of 63c:

Preparation of 63d:

Preparation of 63:

Preparation of 64a:

Preparation of 64b:

Preparation of 64c:

Preparation of 64d:

Preparation of 64:

| compd | X | pos | overall yield, %[a] | mp, °C | recryst sol[b] | anal. |
|---|---|---|---|---|---|---|
| 1a | H | | 18 | 199–200 | B | |
| 1i | C(CH₃)₃ | 4 | 18 | 221.5–222.5 | G | C, H, N, Cl |
| 1s | CH₃ | 4 | 13 | 204.5–205 | A | C, H, N, Cl |
| 1r | CH₃ | 3 | 19 | 200–201 | A | C, H, N, Cl |
| 1j | Cl | 2 | 18 | 192.5–193.5 | B | C, H, N, Cl |
| 1k | Cl | 3 | 22 | 205.5–206.5 | D | C, H, N, Cl |
| 1l | Cl | 4 | 7 | 201–203 | A | C, H, N, Cl |
| 1m | di-Cl | 34 | 13 | 214–215 | B | C, H, N, Cl |
| 1n | F | 2 | 20 | 205.5–206.5 | A | C, H, N, Cl |
| 1o | F | 3 | 26 | 213–214 | A | C, H, N, Cl |
| 1p | F | 4 | 12 | 208.5–210.5 | A | C, H, N, Cl |
| 1t | NH₂·HCl | 3 | 12 | 225.5–227.5 | C | C, H, N, Cl |
| 1u | NH₂·HCl | 4 | 24 | 211 (dec) | C | C, H, N, Cl |
| 1v | NO₂ | 4 | | 189–191 | F | C, H, N, Cl |
| 1w | OH[c] | 2 | | | | |
| 1x | OH | 3 | 16 | 201.5–202 | F | C, H, N, Cl |
| 1b | OH | 4 | 8 | 211–212[d] | F | C, H, N, Cl |
| 1y | OMe | 2 | 28 | 189.5–192 | C | C, H, N, Cl |
| 1z | OMe | 3 | 22 | 203–204.5 | C | C, H, N, Cl |
| 1g | OMe | 4 | 10 | 193.5–195[d] | C | |
| 1aa | di-OMe | 34 | 13 | 214.5–216 | E | C, H, N, Cl |
| 11a | C(CH₃)₃ | 4 | 6 | 199–202 | A | C, H, N, Cl |
| 11c | Cl | 2 | 23 | 186.5–188 | B | C, H, N, Cl |
| 11d | Cl | 3 | 15 | 200–201 | C | C, H, N, Cl |
| 11e | OMe | 2 | 28 | 190–191 | C | C, H, N, Cl |

[a] Free base mixture. [b] A, EtOAc/MeOH (2:1); B, EtOAc/MeOH (1:1); C, EtOAc/MeOH (1:2); D, MeOH; E, acetone/MeOH (1:1); F, acetone; G, acetone/MeOH (2:1). [c] Mixture *erythro* and *threo*. [d] Literature[28] mp 222–224 °C.

Figure 35

Where X:

| | |
|---|---|
| -H | Methylphenidate, 1 |
| -Br | *p*-Bromomethylphenidate, 2 |
| -OCH₃ | *p*-Methoxymethylphenidate, 3 |
| -OH | *p*-Hydroxymethylphenidate |

| X | Organometallic, mol% | 7 % Yield | Enantiopurity of 7 |
|---|---|---|---|
| -O-P(=O)(Ph)(Ph) | PhMgBr, 110 | 8 | ND[a] |
| -S-(2-pyridyl) | PhMgBr, 145 | 36 | ND[a] |
| -S-(2-pyridyl) | Ph₂CuBr, 300 | 37 | 90% |
| -S-(2-pyridyl) | Ph₂CuBr, 500 | 57 | 90% |
| -N(O⁻)- | PhLi, 110 | 64 | 90% |
| -N(O⁻)- | PhLi, 100 | 47 (73[b]) | 99% |
| -N(O⁻)- | PhMgBr, 300 | 22 | ND[a] |

[a]ND = Not Determined
[b]Yield based on recovered starting material

| borane reagent | mol % | temp, °C | yield, % | ratio threo/erytho |
|---|---|---|---|---|
| BH$_3$·THF | 200 | 23 | 89 | 72/28 |
| BH$_3$·Me$_2$S | 200 | 23 | 73 | 59/41 |
| (thexyl)-BH$_2$ | 200 | 0 | 46 | 35/65 |
| (-)-IPC—BH$_2$ | 300 | 23 | 40 | 24/76 |
| (+)-IPC—BH$_2$ | 300 | 23 | 55 | 100/0 |
| (cyclohexyl)$_2$—BH | 400 | 0 | 18 | 57/43 |

METHYLPHENIDATE DERIVATIVES AND USES OF THEM

CROSS-REFERENCE TO RELATED APPLICATIONS

This application is a continuation of U.S. patent application Ser. No. 11/336,029, filed Jan. 20, 2006, which claims the benefit of priority from provisional application Nos. 60/645,778, filed Jan. 20, 2005, and 60/663,006, filed Mar. 18, 2005. The complete disclosures of these priority applications are incorporated herein by reference.

FIELD OF THE INVENTION

The invention relates to uses of methylphenidate derivatives. The uses include inhibiting angiogenesis and treating angiogenic diseases and conditions.

BACKGROUND

Methylphenidate is the treatment of choice for children and adults diagnosed with attention deficit/hyperactivity disorder (ADHD), including its inattentive subtype (formerly known as attention deficit disorder or ADD). Certain derivatives of methylphenidate have also been proposed for the treatment of ADD (see U.S. Pat. No. 6,025,502) and for the treatment of other neurological disorders and conditions (see U.S. Pat. Nos. 5,859,249, 6,025,502 and 6,486,177 and PCT application WO 99/36403).

Methylphenidate is a mild central nervous stimulant and is also taught for treating apathy, fatigue, cognitive decline, and depression in cancer patients, AIDS patients and other seriously ill patients. See U.S. Pat. Nos. 5,908,850, 6,127,385, 6,395,752 and 6,486,177, Challman and Lipsky, *Mayo Clin. Proc.*, 75:711-721 (2000) and Leonard et al., *Hum. Psychopharmacol. Clin. Exp.*, 19:151-180 (2004).

It has been reported that methylphenidate is not carcinogenic, and that there is a less than expected rate of cancer, in rats and humans taking methylphenidate. See Dunnick and Hailey, *Toxicology*, 103:77-84 (1995), National Toxicology Program, *Natl. Toxicol. Program Tech. Rep. Ser.*, 439:1-299 (1995), Dunnick et al., *Cancer Lett.*, 102:77-83 (1996) and Teo et al., *Mutat. Res.*, 537:67-79 (2003). However, there is some evidence that methylphenidate is carcinogenic in mice. Dunnick and Hailey, *Toxicology*, 103:77-84 (1995) and National Toxicology Program, *Natl. Toxicol. Program Tech. Rep. Ser.*, 439:1-299 (1995). Further, some types of tumors have been reported to be decreased, while other types of tumors have been reported to be increased. See Dunnick and Hailey, *Toxicology*, 103:77-84 (1995), National Toxicology Program, *Natl. Toxicol. Program Tech. Rep. Ser.*, 439:1-299 (1995) and Dunnick et al., *Cancer Lett.*, 102:77-83 (1996).

SUMMARY OF THE INVENTION

The invention provides methods of using a compound of formula I

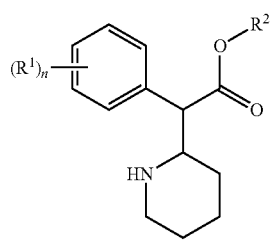

wherein n is an integer from 1 to 5, and each $R^1$ is independently aryl, heteroaryl, alkyl, cycloalkyl, alkoxy, aryloxy, acyl, carboxyl, hydroxyl, halogen, amino, nitro, sulfo or sulfhydryl. Each alkyl can optionally be substituted with hydroxyl, amino or sulfhydryl. $R^2$ is hydrogen or lower alkyl.

In a first embodiment, the invention provides a method of inhibiting angiogenesis in an animal. The method comprises administering an effective amount of a compound of formula I, or a pharmaceutically-acceptable salt or a prodrug thereof, to the animal.

In a second embodiment, the invention provides a method of treating an angiogenic disease or condition in an animal. The method comprises administering a therapeutically effective amount of a compound of formula I, or a pharmaceutically-acceptable salt or a prodrug thereof, to the animal.

In a third embodiment, the invention provides a method of treating a proliferative disorder in an animal. The method comprises administering a therapeutically effective amount of a compound of formula I, or a pharmaceutically-acceptable salt or a prodrug thereof, to the animal.

The invention also provides a compound of formula IA:

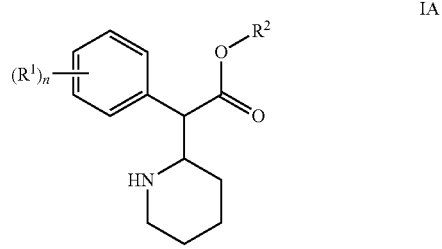

where
n is an integer from 1 to 5;
each $R^1$ is independently a moiety of the formula —C(O)—$R^8$, —O$R^7$ or —C(O)—O—$R^3$;
$R^2$ is hydrogen or lower alkyl;
$R^3$ is hydrogen, alkyl, cycloalkyl or aryl;
$R^7$ is aryl; and
$R^8$ is cycloalkyl or aryl.

The invention further provides a pharmaceutical composition comprising a pharmaceutically-acceptable carrier and a compound of formula IA:

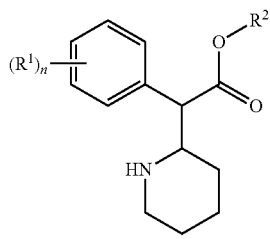

or a salt or prodrug thereof,
where
  n is an integer from 1 to 5;
  each $R^1$ is independently a moiety of the formula —C(O)—$R^8$, —O$R^7$ or —C(O)—O—$R^3$;
  $R^2$ is hydrogen or lower alkyl;
  $R^3$ is hydrogen, alkyl, cycloalkyl or aryl;
  $R^7$ is aryl; and
  $R^8$ is cycloalkyl or aryl.

BRIEF DESCRIPTION OF THE DRAWINGS

In FIG. 9B, the top dark gray bar in each instance is c-Jun and the bottom light gray bar is NFκB.

FIG. 29 depicts the synthesis for compound 64a.

FIG. 35 shows a summary of selected properties of the compounds synthesized in the Deutsch study.

DETAILED DESCRIPTION OF THE INVENTION

Figure 1A:
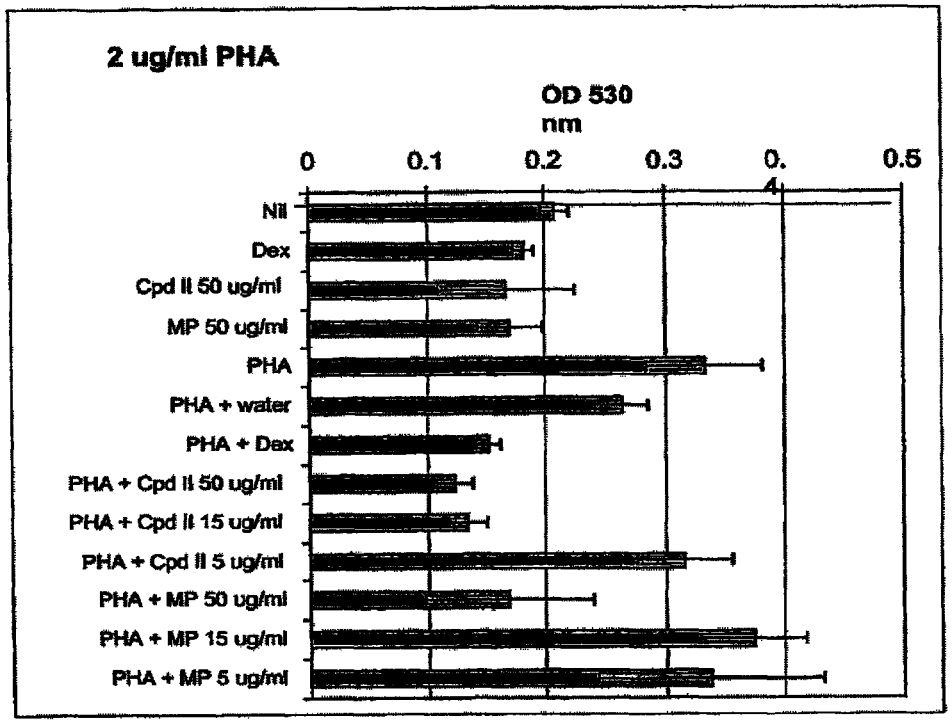
FIGS. 1A-C are graphs of OD at 530 nm for various additives to peripheral blood lymphocyte (PBL) cultures stimulated with 2 µg/ml, 5 µg/ml and 20 µg/ml phytohemagglutinin (PHA), respectively.

In one aspect, compounds of formula I are useful in the practice of the present invention.

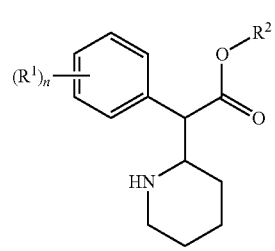

In Formula I, n is an integer from 1 to 5. Preferably n is 1 or 2.

Each $R^1$, which may be the same or different, is aryl, heteroaryl, alkyl, cycloalkyl, alkoxy, aryloxy, acyl, carboxyl, hydroxyl, halogen, amino, nitro, sulfo or sulfhydryl. Each alkyl can optionally be substituted with hydroxyl, amino or sulfhydryl. $R^1$ is preferably aryl, alkyl, cycloalkyl, alkoxy, aryloxy or acyl. More preferably $R^1$ is aryl, alkyl or cycloalkyl, even more preferably aryl, most preferably phenyl.

In formula I, $R^2$ is hydrogen or lower alkyl. Preferably, $R^2$ is —$CH_3$.

In one specific embodiment, the compound of formula II is particularly useful in the present invention:

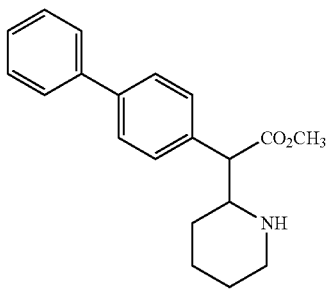

II

"Acyl" means a moiety of the formula —C(O)—$R^3$, wherein $R^3$ is H, alkyl, cycloalkyl or aryl.

"Amino" means a moiety of the formula —$NR^4R^5$, wherein each of $R^4$ and $R^5$ is independently H or lower alkyl, preferably lower alkyl.

"Alkoxy" means a moiety of the formula —$OR^6$, wherein $R^6$ is alkyl. An example of an alkoxy group is methoxy (—O—$CH_3$).

"Alkyl" means a monovalent saturated straight-chain or branched hydrocarbon containing 1-8 carbon atoms. Each alkyl may, optionally, be substituted with one or more amino, hydroxyl or sulfhydryl groups.

"Aryl" means a monovalent mono-, bi- or tricyclic aromatic hydrocarbon moiety of 6 to 14 ring carbon atoms. Preferred is phenyl.

"Aryloxy" means a moiety of the formula —OR', wherein $R^7$ is aryl. An example of an aryloxy group is phenoxy.

"Carboxyl" means a moiety of the formula —C(O)—$OR^3$, wherein $R^3$ is H, alkyl, cycloalkyl or aryl.

"Cycloalkyl" means a saturated, monovalent mono- or bicyclic hydrocarbon moiety of three to ten ring carbon atoms. Preferably the cycloalkyl contains 4-8 ring carbon atoms. The most preferred cycloalkyl is cyclohexyl.

"Halogen" means chlorine, fluorine, bromine or iodine. Preferred is chlorine or bromine.

"Heteroaryl" means a monovalent monocyclic or bicyclic aromatic moiety of 5 to 12 ring atoms containing one, two, or three ring heteroatoms each of which is independently selected from N, O, and S, the remaining ring atoms being C.

"Hydroxyl" means —OH.

"Lower alkyl" means a saturated straight-chain or branched hydrocarbon containing 1-4 carbon atoms.

"Nitro" means —$NO_2$.

"Sulfhydryl" means —SH.

"Sulfo" means —$SO_3H$.

"Prodrug" means any compound which releases an active parent drug according to formula I in vivo when such prodrug is administered to a mammalian subject. Prodrugs of a compound of formula I are prepared by modifying one or more functional group(s) present in the compound of formula I in such a way that the modification(s) may be cleaved in vivo to release the parent compound. Prodrugs include compounds of formula I wherein a hydroxy, amino, or sulfhydryl group in a compound of formula I is bonded to any group that may be cleaved in vivo to generate the free hydroxyl, amino, or sulfhydryl group, respectively. Examples of prodrugs include, but are not limited to, esters (e.g., acetate, formate, and benzoate derivatives), carbamates (e.g., N,N-dimethylaminocarbonyl) of hydroxy functional groups in compounds of formula I, and the like.

"Inhibit" or "inhibiting" is used herein to mean to reduce (wholly or partially) or to prevent.

"Treating" or "treatment" of a disease or condition includes: (1) preventing the disease or condition, i.e., causing the clinical symptoms of the disease or condition not to develop in a mammal that may be exposed to or predisposed to the disease or condition, but does not yet experience or display symptoms of the disease or condition; (2) inhibiting the disease or condition, i.e., arresting or reducing the development of the disease or condition or its clinical symptoms; or (3) relieving the disease or condition, i.e., causing regression of the disease or condition or its clinical symptoms, including curing the disease or condition.

An "effective amount" means the amount of a compound that, when administered to an animal for treating a disease or condition or for causing an effect is sufficient to do so. The "effective amount" can and will most likely vary depending on the compound, the disease or condition and its severity, or the effect sought to be caused, and the age, weight, etc., of the animal to be treated.

Methods of synthesizing the compounds of formula I useful in the present invention are known in the art. See, e.g., U.S. Pat. Nos. 5,859,249 and 6,025,502, PCT application WO 99/36403, Pan et al., *Eur. J. Pharmacol.*, 264, 177-182 (1994), Gatley et al., *Life Sci.*, 58, 231-239 (1996), Deutsch et al., *J. Med. Chem.*, 39, 1201-1209 (1996), That et al., *J. Med. Chem.*, 41, 591-601 (1998), Wayment et al., *J. Neurochem.*, 72:1266-1274 (1999), and Krim Thesis (Krim, Lori, Thesis (Ph.D. in Chemistry) (2001), University Of Pennsylvania, Chemistry Library Reading Room (Call No. QD001 2001.K92), University Microfilms Order No. 3031684, ISBN 0-493-44179-41 the complete disclosures of which along with the references cited therein are incorporated herein by reference.

Figure 10:
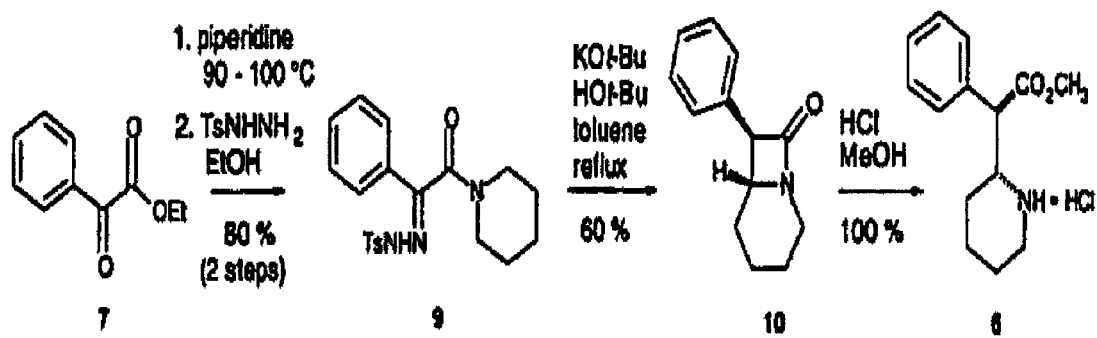
FIG. 10 illustrates a novel and stereoselective synthesis of the hydrochloride salt of dl-threo methylphenidate or Ritalin.

The Krim Thesis (Krim, Lori, Thesis (Ph.D. in Chemistry) (2001), University Of Pennsylvania, Chemistry Library Reading Room (Call No. QD001 2001.K92), University Microfilms Order No. 3031684, ISBN 0-493-44179-4) describes the development of a novel and stereoselective synthesis of the hydrochloride salt of dl-threo methylphenidate or Ritalin 6 (FIG. 10). The construction of 6 is accomplished by an intramolecular C—H insertion reaction of the carbene generated from tosylhydrazone 9 to furnish β-lactam 10. The equilibrating reaction conditions allow for the diastereoselective synthesis of the β-lactam 10 in which the phenyl ring is oriented on the convex face of the bicyclic ring system. Hydrolysis of the β-lactam with acidic methanol provides the hydrochloride salt of dl-threo methylphenidate in four chemical steps, and in 48% overall yield, a significant improvement over the previously reported pathway. The flexibility of this synthesis of methylphenidate allowed for the facile manipulation of all three moieties (aryl, amine, and ester) of the molecule, which resulted in the preparation of a wide variety of novel methylphenidate analogs by Krim and colleagues.

Methylphenidate was first synthesized in 1944 as a mixture of all four possible stereoisomers. Panizzon, L. *Helv. Chim. Acta* 27:1748 (1944). Surprisingly, the syntheses of dl-threo methylphenidate and its analogs have been based solely on this strategy for over 50 years. The Panizzon synthesis was only recently improved by Deutsch and coworkers in 1996. Deutsch et al., *J. Med. Chem.*, 39:1201 (1996). The Deutsch group modified some of the reagents and reaction conditions, but the tactics used in the synthetic sequence were not altered. The Panizzon synthesis incorporating the Deutsch modifications is shown in FIG. 11.

Figure 11:
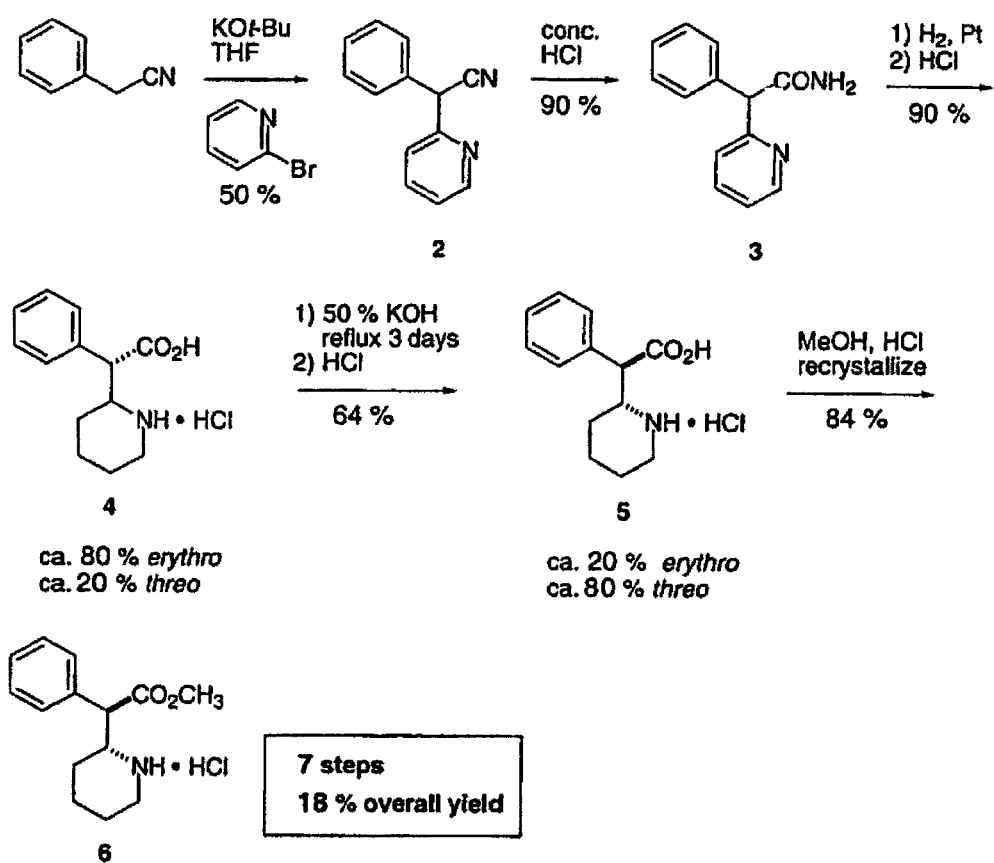
FIG. 11 shows the synthesis of dl-threo methylphenidate and the mixture of possible stereoisomers.

In FIG. 11, alkylation of 2-bromopyridine with the anion of phenylacetonitrile provided the nitrile 2. Hydrolysis of 2 with concentrated hydrochloric acid gives the acetamide 3. Hydrogenation of the pyridine ring of 3 and conversion of the amide to the carboxylic acid affords 80% of the undesired erythro isomer. The threo diastereomer is about 80 times more potent than the erythro diastereomer, and Ritalin is therefore, currently sold as a mixture of the d- and l-threo isomers. Additionally, the erythro racemate has been shown to possess very little therapeutic effect and, in fact, results in toxic hypertensive effects. Accordingly, the undesired erythro diastereomer must be epimerized to the more potent threo diastereomer. This epimerization requires harshly basic reaction conditions, i.e., refluxing 50% potassium hydroxide for 3 days. Reesterification and crystallization provides the hydrochloride salt of dl-threo methylphenidate, 6. This chemical sequence affords threo methylphenidate in 7 chemical steps and in 18% overall yield.

The three major improvements which Deutsch and coworkers incorporated into this synthesis are worthy of mention. In the first step, the yield and ease of the alkylation of phenyl acetonitrile were improved by employing potassium t-butoxide in tetrahydrofuran with 2-bromopyridine, as opposed to the Panizzon method of sodium amide in toluene with 2-chloropyridine. Additionally, the Deutsch protocol for the hydrolysis of nitrile 2 to amide 3 uses concentrated hydrochloric acid which gives an increased yield over the previous method of using concentrated sulfuric acid. The last and most significant modification of the synthesis made by Deutsch was to epimerize the major erythro diastereomer to the desired threo isomer at the carboxylic acid 4 stage of the synthesis. Prior to Deutsch's work, the epimerization step was carried out on the mixture of amides which was obtained after hydrogenation of the pyridine ring. The Deutsch group found that epimerizing the acid was more efficiently reproducible and provided higher overall yields.

Despite the improvements made by Deutsch, some obvious drawbacks to this reaction sequence remain, especially for an industrial synthesis. The synthesis is relatively lengthy and utilizes inconvenient reaction conditions for large scale preparation, such as a catalytic hydrogenation reaction. Perhaps the most unattractive feature of this synthesis is that it is non-selective, requiring an epimerization in order to obtain the threo isomer. Since only the threo isomers are desired, an exploitation of efficient synthetic methods to selectively produce the threo isomer would be a significant process improvement.

Figure 12:
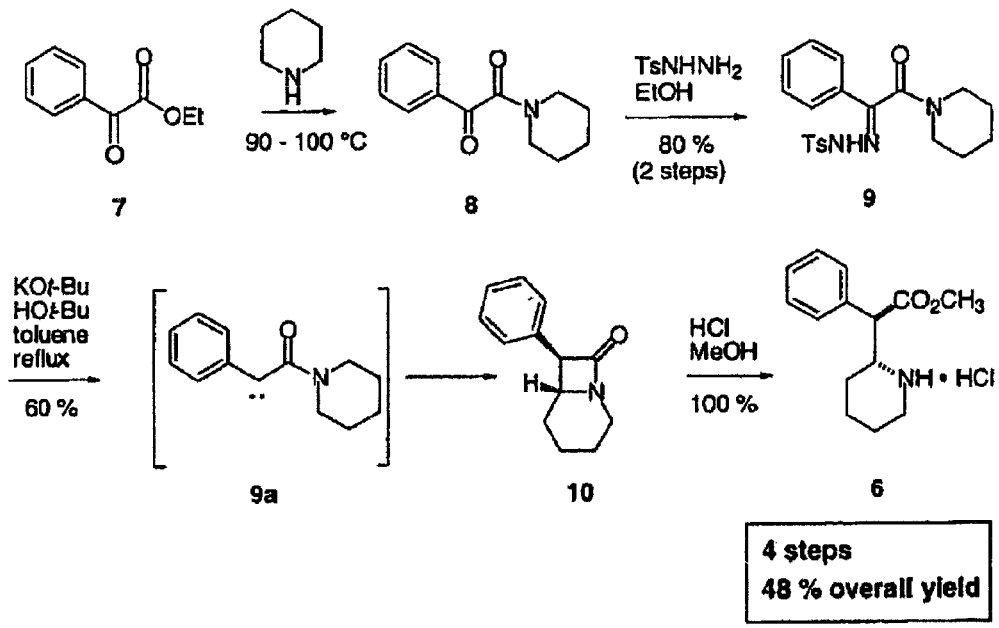
FIG. 12 shows a synthesis to stereoselectively render threo methylphenidate.

Due to the drawbacks associated with the Panizzon/Deutsch synthesis of racemic threo methylphenidate, Dr. Jeffrey Axten, a member of the Winkler group at the University of Pennsylvania, initiated a synthetic project to stereoselectively render threo methylphenidate. The stereoselective synthesis devised by Dr. Axten and subsequently optimized and utilized by Krim, also a member of the Winkler group, is depicted in FIG. 12 (hereinafter referred to as the "Winkler group synthesis"). See Axten et al., *J. Org. Chem.*, 63:9628 (1998). See also PCT Publication No. WO 99/36403, which is also concerned with this method of synthesis.

In FIG. 12, condensation of ethyl phenylglyoxalate 7 with piperidine, neat, at 90° C. affords the α-keto amide 8 after a simple trituration. Imai et al., *Chem. Pharm. Bull.*, 35:2646 (1987). Exposure of this α-keto amide to tosylhydrazide provides tosylhydrazone 9 which precipitates from the reaction mixture. Treatment of the tosylhydrazone with excess potassium t-butoxide in refluxing toluene gives rise to β-lactam 10 via the intermediacy of carbene 9a in the intramolecular C—H insertion reaction. The β-lactam was obtained in 60% yield on crystallization of the crude reaction mixture. The equilibrating reaction conditions allow for the diastereoselective synthesis of this β-lactam (6:1 mixture of exo:endo adducts), in which the phenyl ring is oriented on the convex face of the bicyclic ring system. The relative stereochemistry of the β-lactam was determined unambiguously by the use of X-ray crystallography. Methanolysis of the β-lactam with acidic methanol provides the hydrochloride salt of dl-threo methylphenidate as a single diastereomer in which the relative stereochemistry of the β-lactam has been completely preserved. In terms of industrial scale preparation, it is important to note that all of these compounds are crystalline solids which involve no column chromatography for purification. Also, each of these steps is readily amenable to scale-up. This chemical sequence furnishes dl-threo methylphenidate in just 4 chemical steps and in almost 50% overall yield.

Figure 13:
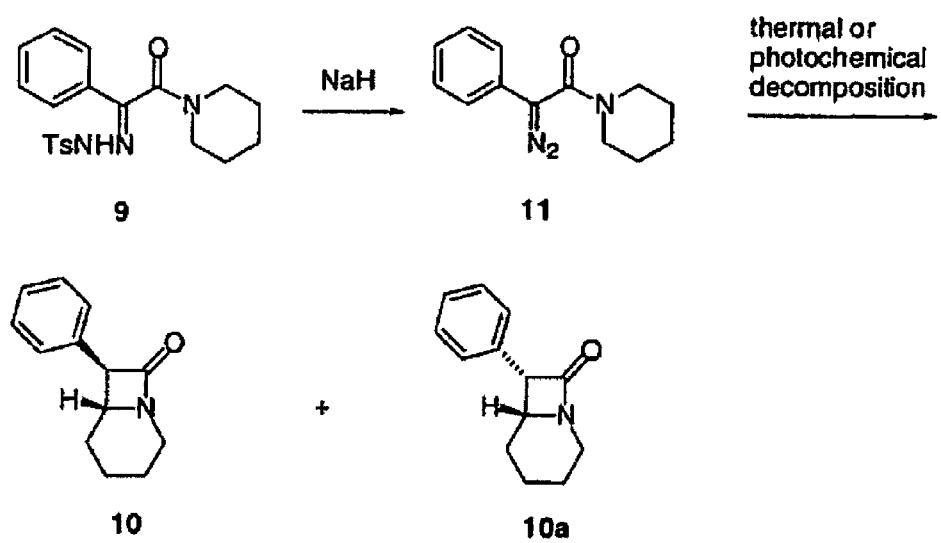
FIG. 13 shows an example of β-lactam formation from an α-keto amide.

The key step in this efficient reaction sequence is the intramolecular C—H insertion reaction and this reaction is worthy of comment. The first example of β-lactam formation from an α-keto amide, as shown in FIG. 13, was reported by Corey and Felix in 1965. Corey and Felix, *J. Am. Chem. Soc.*, 87: 2518 (1965). They reported the stereoselective formation of a β-lactam product in 50% yield by irradiation of 11, which was obtained by treatment of 9 with NaH. However, the stereochemistry of the β-lactam had not been established. Corey and Felix reported the thermal decomposition of 11 to give the same product. In re-investigating their results, the Winkler group established that irradiation of 11 leads to the formation of a 4:1 mixture of exo-10 and endo-10a in quantitative yield, while we observe a 3.5:1 ratio of exo-10 to endo-10a under thermal conditions (toluene reflux).

The past 30 years have seen a significant increase in the utility of diazocarbonyl compounds as precursors to carbon-carbon bond formation. Insertion reactions of carbenes into C—H bonds were first introduced by Meerwein, Rathjen, and Werner (Meerwein et al., *Ber. Dtsch. Chem. Ges.*, 75:1610 (1942)) and since then, have created great interest in the synthetic community. Until the late 1990's, when there were dramatic advances in metal carbenoid species, almost all of the synthetically useful applications of C—H insertion reactions were intramolecular. Intramolecular carbene C—H insertion reactions have been well studied and reviewed (Khlebnikov et al., *Adv. In Heterocyclic Chem.*, 65:93 (1996) and Ye et al., *Chem. Rev.*, 94:1091 (1994)) and therefore this reaction will not be discussed here in great detail. However, the regio- and stereoselectivity of the insertion reaction in Krim's synthesis of methylphenidate is noteworthy.

First, the regioselectivity of this noteworthy reaction will be discussed. In general, C—H insertion leading to the formation of a five membered ring is the favored process. However, construction of other ring sizes by carbene C—H insertion is also possible depending on certain variables. The regioselectivity in the insertion reaction, which eventually determines the control of the ring size of a certain molecule, can depend upon: the type of diazo function, the degree of substitution where the insertion takes place, the proximity of a heteroatom, and steric factors. For instance, the position a to a heteroatom (be it N, O or S) is ideally situated for C—H insertion. It has been generally recognized (Kirmse, *Carbene Chemistry*, $2^{nd}$ ed., Wiley & Sons, NY, 1973, 1) that carbene insertion into C—H bonds of heteroatomic compounds proceeds, if possible, with insertion into the C—H bond a to the heteroatom. Several research groups have exploited this preference for insertion in the development of syntheses for the preparation of β-lactams. Corey and Felix, *J. Am. Chem. Soc.,* 87:2518 (1965): Brown et al., *Tetrahedron Lett.,* 27:247 (1986); Doyle et al., *Tetrahedron Lett.,* 30:5397 (1989).

Figure 14:
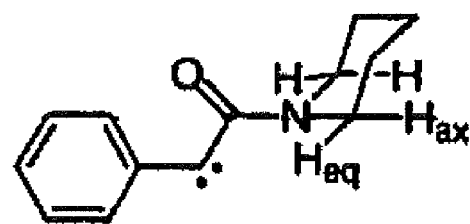
FIG. 14 depicts the planar geometry of the amide.

The stereochemistry of the carbene insertion can be rationalized by preferential C—H insertion into the equatorial C—H bond (Doyle et al., *Synlett,* 1075 (1995)) so that the amide may retain its planar geometry as seen in FIG. 14. It is worthy of note that the 6:1 stereoselection is a thermodynamic value, as there may be equilibration under the reaction conditions in forming the β-lactam (excess t-butoxide in refluxing toluene). The epimerizable conditions allow the phenyl ring to orient itself onto the convex face of the bicyclic ring system. The kinetic ratio for insertion is approximately 3.5-4:1, as this was the ratio of exo:endo adducts which were seen during photochemical or thermal decomposition of the diazocarbonyl.

Figure 15:
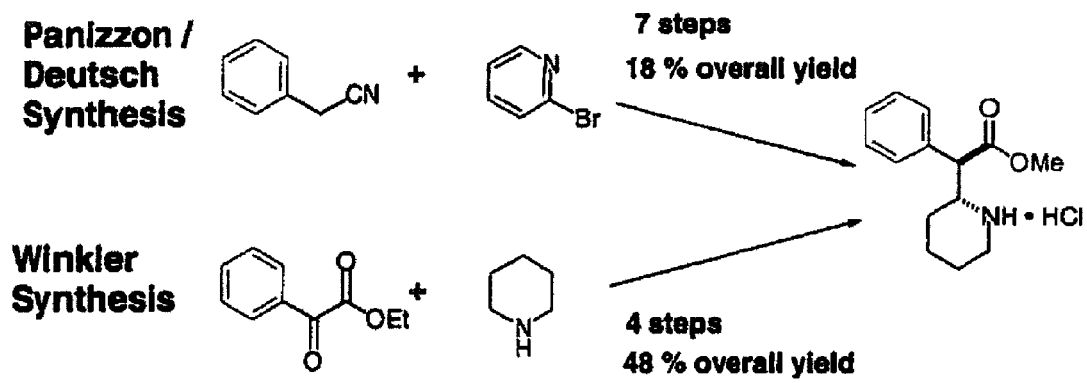
FIG. 15 is a comparison of the Panizzon/Deutsch synthesis of methylphenidate with the Winkler synthesis.

FIG. 15 compares the Panizzon/Deutsch synthesis of methylphenidate with the Winkler group's synthesis. The Winkler group's synthesis significantly reduces the number of steps, as well as greatly increases the overall yield.

A flexible synthesis of methylphenidate is crucial for the development of potentially important methylphenidate analogs. The unique flexiblity of the Winkler group's synthesis is evident by comparing the starting materials of the two methylphenidate syntheses, FIG. 15. The Panizzon/Deutsch synthesis allows for some modifications in the aromatic substitution pattern of methylphendiate, as one could start with various substituted phenyl acetonitrile derivatives. However, this synthesis is extremely inflexible with regard to the amine portion of the molecule since this moiety originates from 2-bromopyridine.

On the other hand, the Winkler group's synthesis allows for the easy manipulation in both the aryl and amine regions of methylphenidate. The Winkler group was able to start with a wide variety of aryl keto esters which are readily available in just one step from the corresponding aryl halide. Additionally, almost any secondary amine, be it cyclic or acyclic, may be employed in the Winkler group's synthesis in order to provide a wide variety of novel methylphenidate analogs. Thus, the Winkler group's approach towards the synthesis of methylphenidate allows for the preparation of diverse analogs which were previously inaccessible.

Figure 16:
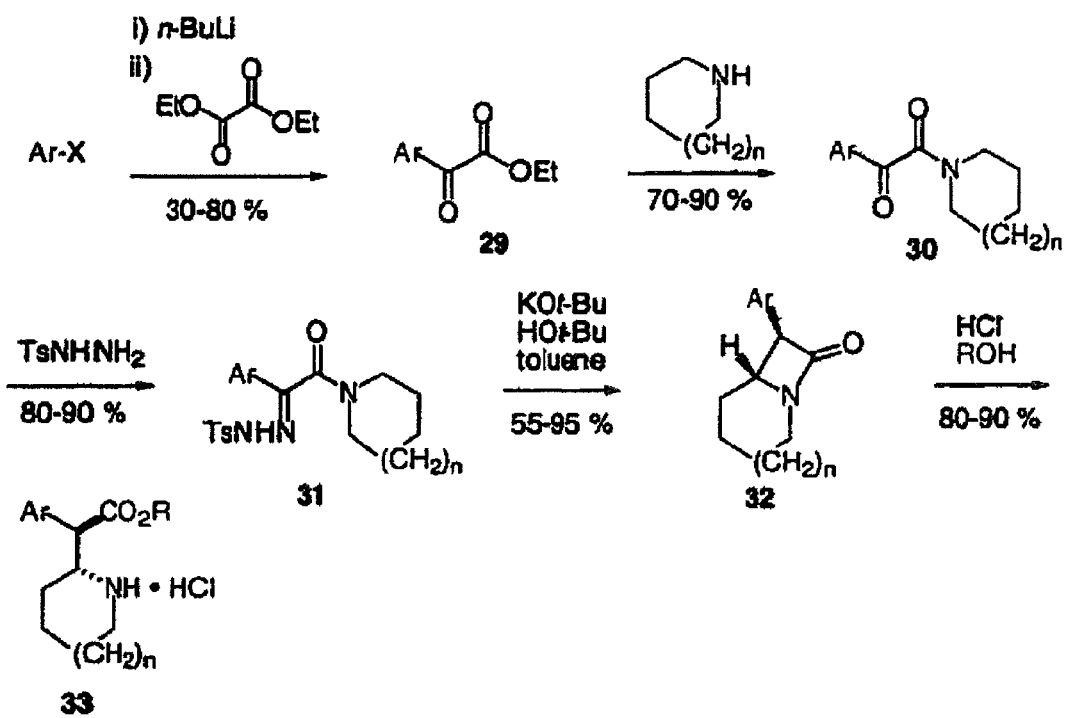
FIG. 16 is a review of the Winkler group's synthesis of methylphenidate.

Studies on methylphenidate have been limited to modifications of the ester or of the substitution pattern on the aryl moiety, due to the limitations of the previously reported synthetic sequence of methylphenidate. The concise and flexible approach to methylphenidate developed in the Winkler laboratory greatly increased the degree of variation that is possible in the preparation of methylphenidate analogs, allowing for the first time the facile manipulation of each moiety (aryl, amine, and ester) of methylphenidate. FIG. 16 is a review of this synthesis of methylphenidate. This general schematic depicts the flexibility which the Winkler group exploited in the preparation of novel methylphenidate analogs.

In FIG. 16, the requisite α-keto ester 29 can be prepared by the treatment of almost any aryl halide with n-butyllithium, followed by exposure to diethyl oxalate. The α-keto ester can be condensed with a wide variety of secondary amines, cyclic or acyclic, to provide α-keto amide 30. The α-keto amide can be carried through the same reaction sequence described above to provide a novel β lactam 32. The lactam can then be opened with acid and an alcohol in order to obtain a large number of methylphenidate analogs 33.

The synthesis of several methylphenidate analogs were next described in the Krim Thesis. To simplify, the discussion in the Krim Thesis was divided into three categories corresponding to the region of the molecule that had been modified: ester, aryl, and amine. Here, only the first two categories of analogs will be described.

Figure 17:
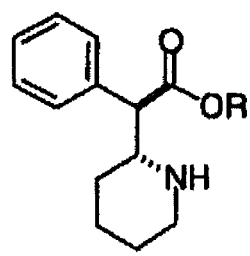
FIG. 17 depicts esters prepared by Portoghese and Malspeis.

The first methylphenidate analogs were synthesized in 1960 by Portoghese and Malspeis. Portoghese and Malspeis, *J. Pharm. Sci.,* 50:494 (1961). These researchers prepared a series of methylphenidate alkyl esters. The esters prepared by Portoghese and Malspeis are shown in FIG. 17.

Due to the limitations of the Panizzon synthesis, the only accessible aromatic analogs were those with substituents placed on the aromatic ring of the starting aromatic moiety, phenylacetonitrile (see above). Until recently, only a handful of these analogs had been prepared. The first aromatic methylphenidate analog had a para hydroxy group on the aromatic ring and was synthesized in 1981. Patrick et al., *J. Med. Chem.,* 24:1237 (1981). The next aromatic analogs were not prepared until more than a decade later by Pan and Gatley; these analogs had ortho, meta, or para bromine atoms placed on the phenyl ring. Pan and Gatley, *Eur. J. Pharmacol.,* 264:177 (1994).

Figure 18:
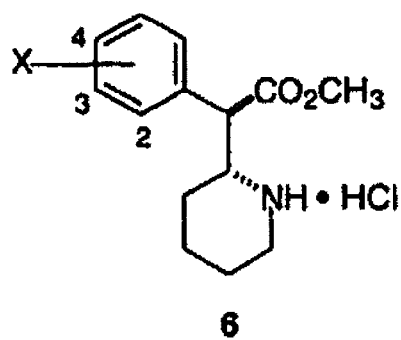
FIG. 18 is a representative sampling of the Deutsch analogs.

A broad survey of aromatic methylphenidate analogs was not conducted until the Deutsch study in 1996. Deutsch et al., *J. Med. Chem.* 39:1201 (1996). This group investigated approximately thirty analogs containing diverse groups positioned at different sites on the phenyl ring. The Krim Thesis reports that a representative sampling of the Deutsch analogs is shown in FIG. 18.

Figure 19:
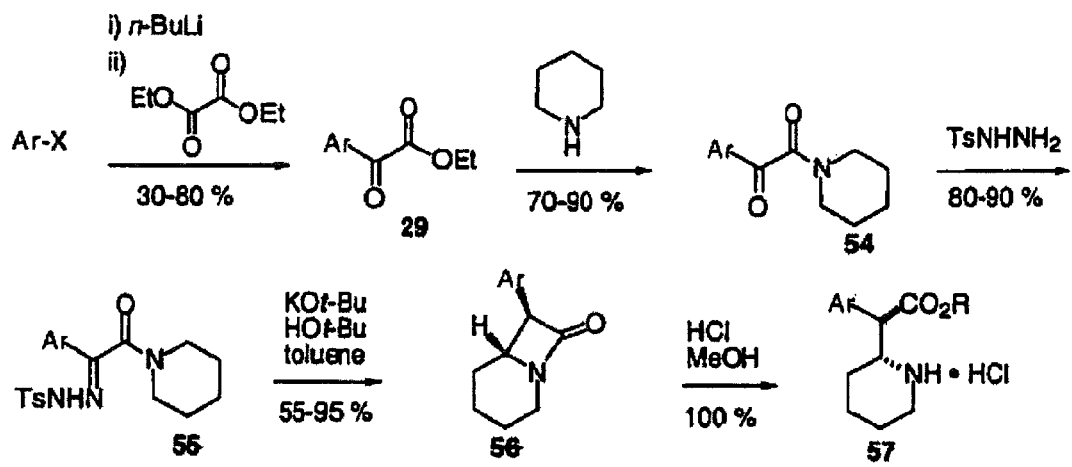
FIG. 19 depicts a general method by which aromatic analogs where synthesized by Krim.

The general method by which the aromatic analogs were synthesized by Krim as described in the Krim Thesis is shown in FIG. 19. Any aryl halide (Ar—X) can be used as the starting material. Exposure of the aryl halide to n-BuLi followed by treatment with excess diethyl oxalate (Middleton et al., *J. Org. Chem.,* 45:2883 (1980)) provides the corresponding aryl α-keto ester. This ketoester can then be carried through the reaction sequence shown to provide a novel aromatic methylphenidate analog.

Figure 20:
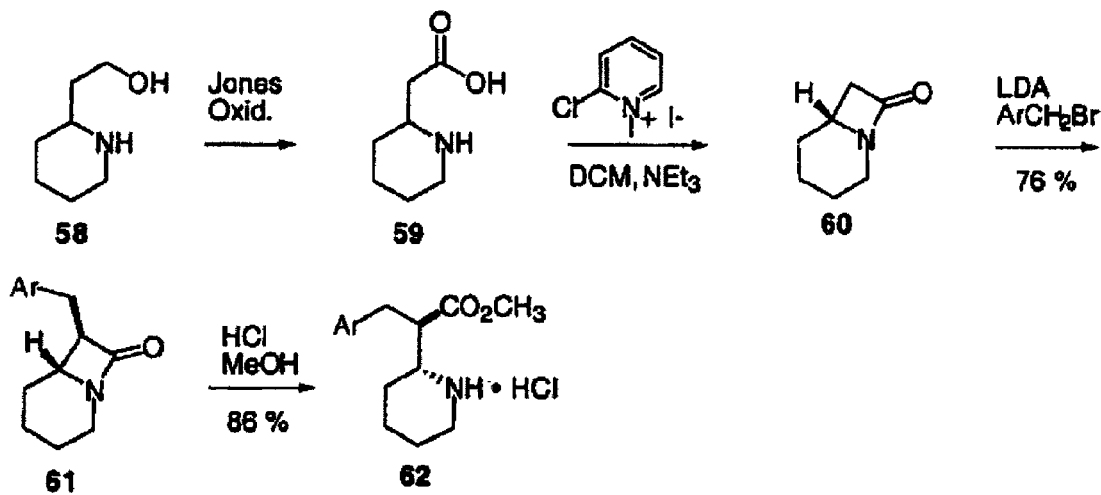
FIG. 20 shows a synthesis for preparing benzyl and diphenyl methyl analogs.

Along with the aromatic analogs prepared by the method shown above, additional analogs were prepared in order to distance the aryl moiety from the ester-bearing carbon. Specifically, the benzyl and diphenyl methyl analogs were prepared via the methodology shown in FIG. 20.

The known β-lactam 60 was prepared starting with commercially available 2-ethanolpiperidine 58. Murahashi et al., *Tetrahedron Lett.,* 5949 (1988). Subsequent Jones oxidation to the amino acid 59, followed by cyclization using Mukaiyama's coupling reagent (Bald et al., *Chem. Letters,* 1163 (1975)) provides the bare β-actam 60. Alkylation of the β-lactam with LDA and either benzyl bromide or diphenylmethyl bromide produced alkylated lactam 61 where the aromatic ring is on the convex face of the bicyclic ring system. The lactam was then opened with hydrochloric acid and methanol to provide the desired aromatic analogs 62.

Figure 21:
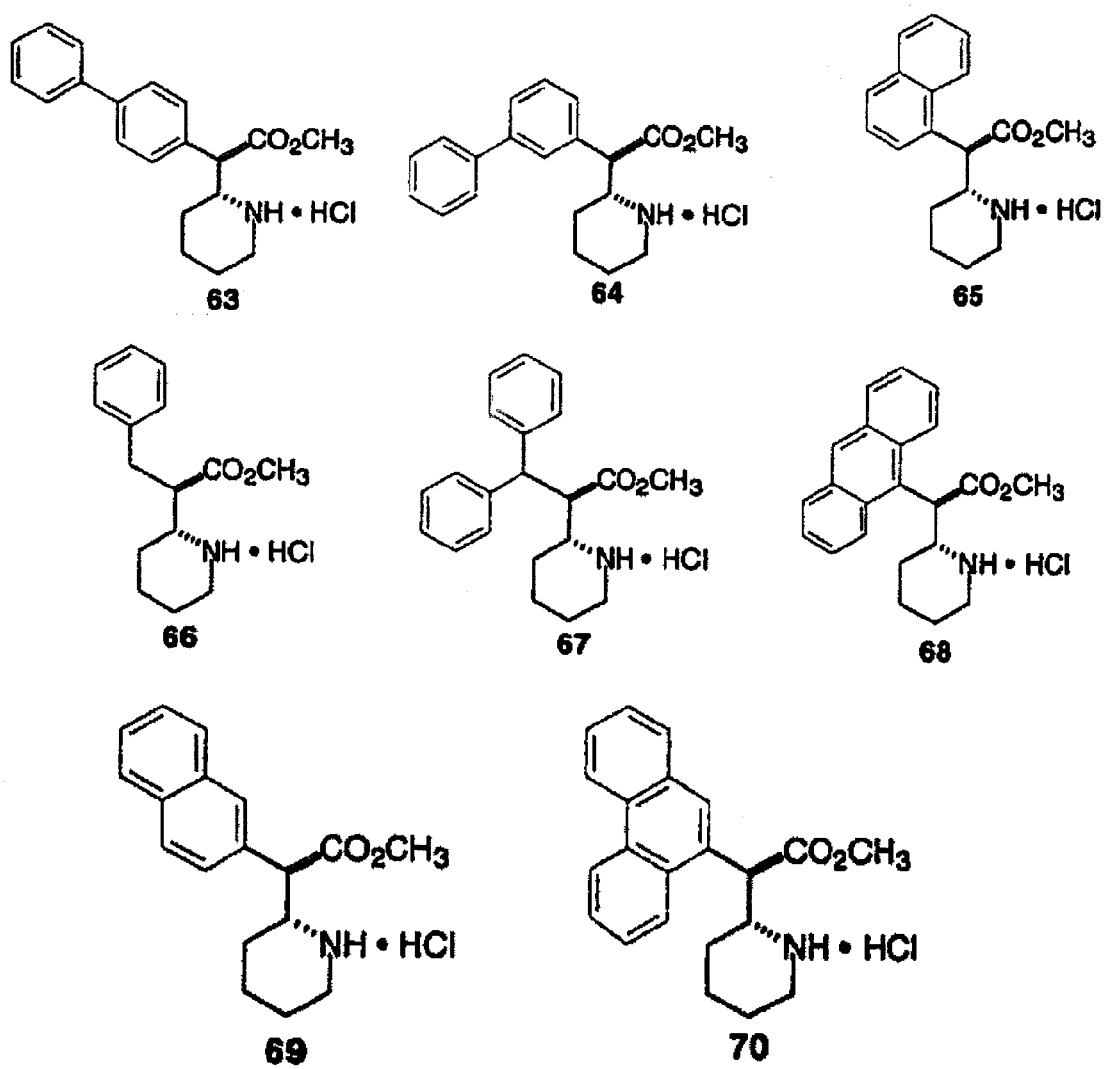
FIG. 21 depicts some of the aromatic analogs prepared by the Winkler group.

Some of the aromatic analogs that were prepared by the Winkler group are shown in FIG. 21.

The Krim Thesis also includes detailed experimental procedures for the synthesis of several methyphenidate derivatives. Some of these procedures are described below.

All reactions were carried out under an argon atmosphere using flame dried glassware. Diethyl ether and tetrahydrofuran (THF) were distilled from sodium/benzophenone. Benzene, toluene, acetonitrile, triethylamine, hexamethylphosphoric triamide (HMPA), diisopropylamine and dichloromethane (DCM) were distilled from calcium hydride. Commercial reagents were used as received.

Thin layer chromatography was performed on 0.25 mm silica gel plates from Merck. The plates were visualized with UV-light followed by staining with phosphomolybdic acid, cerie sulfate, anisaldehyde or potassium permanganate. Flash column chromatography was performed using 230-400 mesh (particle size 0.04-0.063 mm) silica gel supplied by Mallinckrodt or E. Merck.

Infrared spectra were recorded on a Perkin-Elmer 1600 Series FT-IR spectrophotometer and were recorded neat or on a KBr plate. Unless otherwise noted, NMR spectra were obtained on a Broker AMX-500 spectrometer using deuterated chloroform as solvent. $^1$H NMR and $^{13}$C NMR spectra were recorded at 500 MHz and 125.7 MHz respectively and referenced as δ 7.24 for proton and δ 77.0 for carbon. High resolution mass spectra were obtained by Mr. John Dykins and Dr. Rakesh Kohli at the University of Pennsylvania Mass Spectrometry Service Center on either a VG micromass 70/70H high resolution double-focusing electron impact/chemical ionization spectrometer with a Kratos DS-50-S data system or a VG ZAB-E spectrometer. Single-crystal X-ray diffraction structure determination was performed by Dr. Pat Caroll at the University of Pennsylvania. Melting points were obtained on a Thomas Hoover capillary melting point apparatus and are uncorrected.

Figure 22:
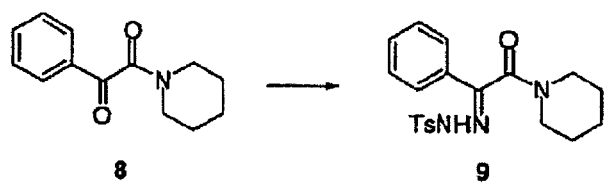
FIG. 22 depicts the synthesis for compound 9.

To a solution of amide 8 (FIG. 22) in dimethoxyethane was added p-toluenesulfonhydrazide (1.1 equivalent) at room temperature. This solution was cooled to 0° C. and anhydrous HCl gas bubbled through the solution for 30 seconds. The reaction mixture was gently refluxed for 3-12 hours (as determined by monitoring by TLC). The solution was cooled first to room temperature at which point a precipitate formed and then further cooled to 0° C. Diethyl ether was added to induce more crystallization. The precipitate was collected by filtration, washed with cold ether, and subsequently allowed to air dry to give pure tosylhydrazone. The tosylhydrazone was recrystallized in ether:ethanol (3:1) to give needlelike crystals of 9 (80%): Melting point: 191° C. (dec): $^1$H NMR (500 MHz, CDCl$_3$): δ 8.48 (s, 1H), δ 7.80 (d, 2H, J=8.32 Hz), δ 7.55-7.57 (m, 2H), δ 7.31-7.36 (m, 3H), 7.19 (d, 2H, J=8.14 Hz), δ 3.65 (t, 2H, J=5.3 Hz), δ 3.14 (t, 2H, J=5.6 Hz), δ 2.32 (s, 3H), 61.59-1.62 (m, 4H), δ 1.40-1.42 (m, 2H); $^{13}$C NMR (125 MHz, CDCl$_3$): δ 161.9, 150.6, 144.0, 135.1, 132.1, 130.5, 129.5, 128.7, 127.9, 126.2, 47.3, 42.1, 26.2, 25.5, 24.1, 21.5; IR (KBr pellet): 3062, 2945, 1623, 1448, 1409, 1335, 1298, 1251, 1163, 1081, 1016, 982, 937, 858, 659, 545 cm$^{-1}$; Mass Spectrum m/z (relative intensity); HRMS calculated for C$_{20}$H$_{23}$N$_3$O$_3$S (M+NH$_4$+) 403.1804. found 403.1809.

Figure 23:
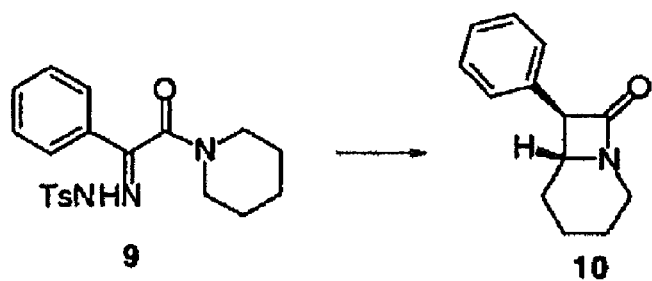
FIG. 23 depicts the synthesis for compound 10.

To a solution of tosylhydrazone 9 (FIG. 23) in toluene was added a 1 M solution of potassium tert-butoxide in tert-butanol (1.1 equiv.) dropwise at room temperature. The mixture was heated to reflux and monitored by both thin layer chromatography (TLC) as well as by the color of the reaction mixture. The originally yellow solution turns bright orange as the diazo compound is formed. After 30 minutes at reflux, the solution returns to a yellow color and TLC showed no starting material. The reaction mixture is washed with water (2 times) and then washed with brine. The aqueous portions are combined and extracted with ethyl acetate. The organic extracts were combined, dried over MgSO$_4$, filtered, and evaporated. The resulting oil or semisolid was purified by flash column chromatography. Further purification by recrystallization from ether yielded a single diastereomer as white crystals of 10 (60%; threo:erythro 6:1): Melting point: 87° C.; $^1$H NMR (500 MHz, CDCl$_3$): δ 7.29-7.32 (m, 2H), δ 7.21-7.27 (m, 3H), δ 3.94 (d, 1H, J=1.49 Hz), δ 3.90 (dd, 1H, J=13.6, 4.4 Hz), δ 3.33-3.36 (m, 1H), δ 2.75-2.81 (m, 1H), δ 2.13-2.17 (m, 1H), δ 1.88-1.91 (m, 1H), δ 1.65-1.69 (m, 1H), δ 1.34-1.46 (m, 3H); $^{13}$C NMR (125 MHz, CDCl$_3$): δ 166.1, 135.5, 128.6, 128.4, 127.1, 63.3, 56.6, 38.8, 30.4, 24.3, 22.1; IR (KBr pellet): 2943, 1746, 1450, 1399, 743 cm$^{-1}$; Mass Spectrum m/z (relative intensity); HRMS calculated for C$_{13}$H$_{15}$NO (M+H$^+$) 202.1232. found 202.1226.

Figure 24:
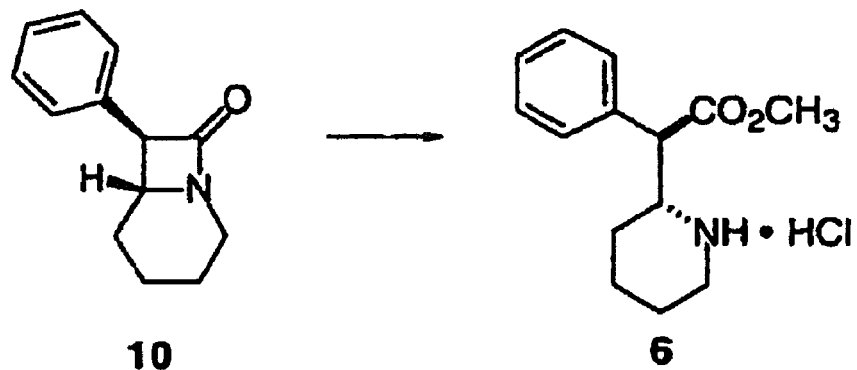
FIG. 24 depicts the synthesis for compound 6.

To a solution of β-lactam 10 (FIG. 24) in MeOH at 0° C., anhydrous HCl gas was gently bubbled through the solution for approximately five minutes. The reaction mixture was allowed to stir at room temperature for 1-5 hours (until all starting material was gone by TLC). The solvent was evaporated and the resultant solid was triturated with ether. The offwhite solid was collected by filtration and washed with ether to give amine salt. This was recrystallized in MeOH-ether to give white crystals of 6 (86%): melting point: 206° C.; $^1$H NMR (500 MHz, D$_2$O): δ 7.34-7.40 (m, 3H), δ 7.24-7.27 (m, 2H), δ 3.92 (d, 1H, J=9.17 Hz), δ 3.75 (ddd, 1H, J=11.5, 2.5 Hz), δ 3.65 (s, 3H), δ 3.38 (d, 1H, J=12.8 Hz), δ 3.00 (ddd, 1H, J=12.9, 3.1 Hz), δ 1.77-1.81 (m, 1H), δ 1.69-1.72 (m, 1H), δ 1.49-1.59 (m, 2H), δ 1.26-1.41 (m, 2H); $^{13}$C NMR (125 MHz, D$_2$O): δ 173.1, 133.2, 129.4, 128.8, 128.6, 57.7, 53.6, 53.2, 45.5, 26.2, 21.7, 21.2; IR (KBr pellet): 3461, 2936, 2807, 2512, 1739, 1584, 1459, 1430, 1320, 1207, 1172, 1148, 1011, 736, 703 cm$^{-1}$: Mass Spectrum m/z (relative intensity); HRMS calculated for C$_{14}$H$_{19}$NO$_2$ (M+H$^+$) 234.1494. found 234.1489.

Figure 25:
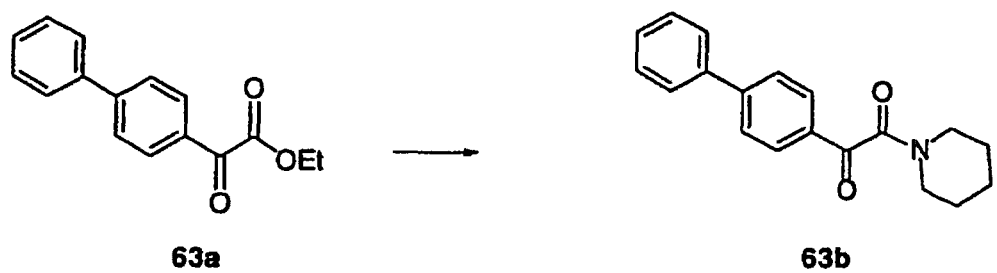
FIG. 25 depicts the synthesis for compound 63b.

A neat mixture of piperidine and aryl α-keto ester 63a (FIG. 25) (equimolar amounts of each) was stirred at 90-100° C. for 2-5 days. The resultant oil was purified by column chromatography (5% diethyl ether-benzene) to give 63b (77%): $^1$H NMR (500 MHz, CDCl$_3$): δ 7.99-8.01 (m, 2H), δ 7.69-7.72 (m, 2H), δ 7.59-7.62 (m, 2H), δ 7.44-7.47 (m, 2H), δ 7.38-7.41 (m, 1H), δ 3.70 (m, 2H), δ 3.30 (dd, 2H, J=5.55, 5.55 Hz), δ 1.69 (dddd, 4H, J=5.67, 5.67, 5.67, 2.74 Hz), δ 1, 1245, 1217, 974, 753 cm$^{-1}$; Mass Spectrum m/z (relative intensity); HRMS calculated for C$_{19}$H$_{19}$NO$_2$(M+H$^+$) 294.1494. found 294.1489.

Figure 26:
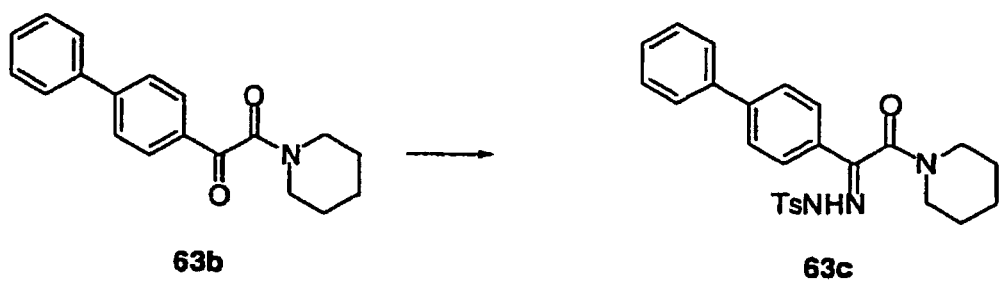
FIG. 26 depicts the synthesis for compound 63c.

To a solution of amide 63b (FIG. 26) in dimethoxyethane was added p-toluenesulfon-hydrazide (1.1 equivalent) at room temperature. This solution was cooled to 0° C. and anhydrous HCl gas bubbled through the solution for 30 seconds. The reaction mixture was gently refluxed for 3-12 hours (as determined by monitoring by TLC). The solution was cooled first to room temperature at which point a precipitate formed and then further cooled to 0° C. Diethyl ether was added to induce more crystallization. The precipitate was collected by filtration, washed with cold ether, and subsequently allowed to air dry to give pure tosylhydrazone. The resultant yellow solid was purified by crystallization with diethyl ether to give 63c (83%): $^1$H NMR (500 MHz, CDCl$_3$): δ 8.12 (s, 1H), δ 7.86 (d, 2H, J=8.33 Hz), δ 7.63-7.64 (m, 2H), δ 7.55-7.59 (m, 4H), δ 7.41-7.44 (m, 2H), δ 7.34-7.37 (m, 1H), δ 7.28 (d, 2H, J=8.10 Hz), δ 3.71 (t, 2H, J=5.55 Hz), δ 3.21 (t, 2H, J=5.55 Hz), δ 2.38 (s, 3H), δ 1.65-1.68 (m, 4H), δ 1.54 (s, 2H), δ 1.47-1.49 (m, 2H); $^{13}$C NMR (125 MHz, CDCl$_3$): δ 161.9, 150.3, 144.0, 143.2, 139.8, 135.1, 130.9, 129.5, 128.8, 127.9, 127.8, 127.3, 126.9, 126.6, 65.7, 47.3, 42.2, 26.3, 25.5, 24.1, 21.5, 15.2; IR (neat): 1625, 1447, 1407, 1348, 1252, 1168, 1078 cm$^{-1}$; Mass Spectrum m/z (relative intensity); HRMS calculated for C$_{26}$H$_{27}$N$_3$O$_3$S (M+Na) 484.1671. found 484.1676.

Figure 27:
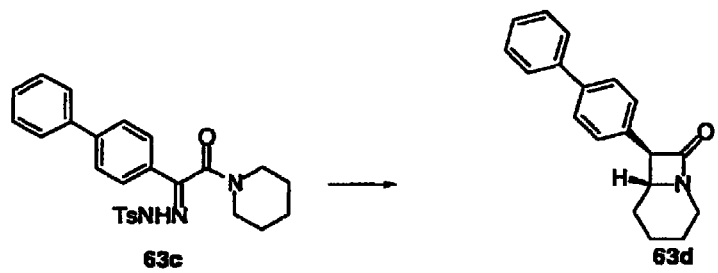
FIG. 27 depicts the synthesis for compound 63d.

To a solution of tosylhydrazone 63c (FIG. 27) in toluene was added a 1 M solution of potassium tert-butoxide in tert-butanol (1.1 equiv.) dropwise at room temperature. The mixture was heated to reflux and monitored by both thin layer chromatography as well as by the color of the reaction mixture. The originally yellow solution turns bright orange as the diazo compound is formed. After 30 minutes at reflux, the solution returns to a yellow color and TLC showed no starting material. The reaction mixture is washed with water (2 times) and then washed with brine. The aqueous portions are combined and extracted with ethyl acetate. The organic extracts were combined, dried over $MgSO_4$, filtered, and evaporated. The resultant white solid was purified by column chromatography (45% diethyl ether: petroleum ether) to give 63d (80%; threo:erythro 4.2:1): $^1$H NMR (500 MHz, $CDCl_3$): δ 7.28-7.60 (m, 9H), δ 3.99 (s, 1H), δ 3.91-3.95 (m, 1H), δ 3.38-3.41 (m, 1H), δ 2.76-2.84 (m, 1H), δ 2.16-2.20 (m, 1H), δ 1.92-1.93 (m, 1H), δ 1.65-1.71 (m, 2H), δ 1.35-1.52 (m, 2H); $^{13}$C NMR (125 MHz, $CDCl_3$): δ 166.2, 140.8, 140.3, 134.7, 128.9, 128.7, 127.7, 127.5, 127.3, 127.1, 127.0, 126.9, 63.2, 56.8, 39.0, 30.5, 24.5, 22.2; IR (neat): 2936, 2854, 1746, 1652, 1487, 1445, 1399 $cm^{-1}$; Mass Spectrum m/z (relative intensity); HRMS calculated for $C_{19}H_{19}NO(M+H^+)$ 278.1545. found 278.1546.

Figure 28:
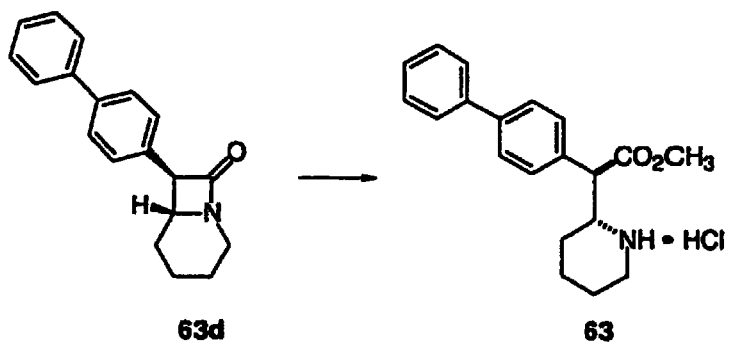
FIG. 28 depicts the synthesis for compound 63.

To a solution of β-lactam 63d (FIG. 28) in MeOH at 0° C., anhydrous HCl gas was gently bubbled through the solution for approximately five minutes. The reaction mixture was allowed to stir at room temperature for 1-5 hours (until all starting material was gone by TLC). The solvent was evaporated and the resultant solid was triturated with ether. The off-white solid was collected by filtration and washed with ether to give the amine salt. The resultant white solid was purified by trituration with diethyl ether:methanol (10:1) to give 63 (37%): melting point: 203° C. (dec); $^1$H NMR (500 MHz, $CD_3OD$): δ 7.64-7.66 (m, 2H), δ 7.59-7.61 (m, 2H), δ 7.41-7.44 (m, 2H), δ 7.32-7.39 (m, 3H), δ 3.97 (d, 1H, J=9.83 Hz), δ 3.83-3.88 (m, 1H), δ 3.74 (s, 3H), δ 3.44-3.47 (m, 1H), δ 3.11 (ddd, 1H, J=12.84, 12.84, 3.15 Hz), δ 1.79-1.89 (m, 2H), δ 1.67-1.76 (m, 1H), δ 1.39-1.60 (m, 3H); $^{13}$C NMR (125 MHz, $CD_3OD$): δ 173.2, 142.9, 141.4, 134.1, 130.1, 129.9, 128.9, 128.8, 127.9, 59.3, 55.0, 53.5, 46.7, 27.7, 23.4, 22.8; IR (KBr pellet): 2948, 2804, 2716, 1732, 1455, 1435, 1208, 1173, 1008 $cm^{-1}$; Mass Spectrum m/z (relative intensity); HRMS calculated for $C_{20}H_{23}NO_2$ $(M+H^+)$ 310.1807. found 310.1801.

Figure 29:
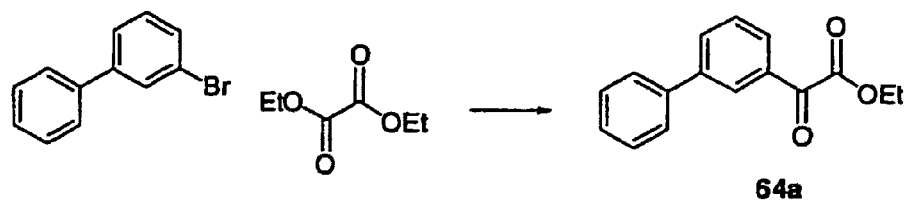

To a 2M solution of the corresponding aryl halide (FIG. 29) dissolved in anhydrous diethyl ether and anhydrous toluene (1:1) was added freshly titrated n-butyllithium (2.5 M in hexanes) (1 equiv.) dropwise at room temperature. This solution was stirred for 15 minutes at room temperature and subsequently stirred at 45-55° C. for 30 minutes. In a separate flask, diethyloxalate (4 equiv) in anhydrous diethyl ether (3M) was cooled to −78° C. To this cooled solution, the aryllithium was added dropwise via cannula and was allowed to stir at −78° C. for 1 hour. To quench the reaction, 2N HCl was added dropwise at 0° C. Distilled water was added to help dissolve the salts formed and the resulting aqueous layer was extracted with ether. The ether extracts were washed with water, dried over $MgSO_4$, filtered, and evaporated. The excess diethyloxalate was removed from the crude product via short path distillation (1 mm Hg). The resultant oil was purified by column chromatography (50% benzene: petroleum ether) to give 64a (43%): $^1$H NMR (500 MHz, $CDCl_3$): δ 8.21 (t, 1H, J=1.69 Hz), δ 7.96-7.97 (m, 1H), δ 7.86-7.87 (m, 1H), δ 7.56-7.60 (m, 3H), δ 7.46 (t, 2H, J=7.46 Hz), δ 7.38-7.40 (m, 1H), δ 4.45 (q, 2H, J=7.15 Hz), δ 1.42 (t, 3H, J=7.14 Hz); $^{13}$C NMR (125 MHz, $CDCl_3$): δ 186.3, 163.7, 142.1, 139.6, 133.5, 133.0, 129.3, 128.9, 128.8, 128.5, 128.0, 127.1, 62.4, 14.1; IR (neat): 1737, 1688, 1454, 1317, 1277, 1185 $cm^{-1}$; Mass Spectrum m/z (relative intensity); HRMS calculated for $C_{16}H_{14}O_3$ $(M+H^+)$ 255.1021. found 255.1020.

Figure 30:
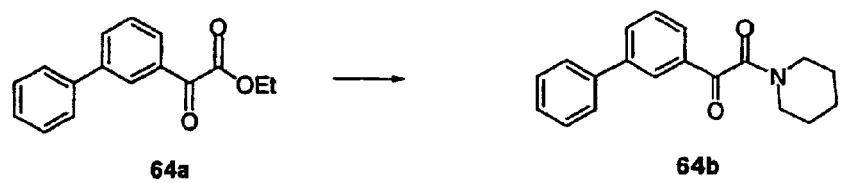
FIG. 30 depicts the synthesis for compound 64b.

A neat mixture of piperidine and aryl α-keto ester 64a (FIG. 30) (equimolar amounts of each) was stirred at 90-100° C. for 2-5 days. The resultant oil was purified by column chromatography (30% diethyl ether: benzene) to give 64b (69%): $^1$H NMR (500 MHz, $CDCl_3$): δ 8.16 (t, 1H, J=1.76 Hz), δ 7.89 (ddd, 1H, J=2.65, 1.23 Hz), δ 7.84 (ddd, 1H, J=2.88, 1.43), δ 7.55-7.60 (m, 3H), δ 7.43-7.46 (m, 2H), δ 7.36-7.39 (m, 1H), δ 3.69-3.70 (m, 2H), δ 3.29-3.31 (m, 2H), δ 1.67-1.69 (m, 4H), δ 1.54-1.55 (m, 2H); $^{13}$C NMR (125 MHz, $CDCl_3$): δ 191.8, 165.4, 142.2, 139.7, 133.7, 133.2, 129.4, 128.9, 128.5, 128.0, 127.9, 127.1, 47.0, 42.2, 26.2, 25.4, 24.3; IR (neat): 2939, 2858. 1681, 1643, 1597, 1450, 1198, 978, 750 $cm^{-1}$; Mass Spectrum m/z (relative intensity); HRMS calculated for $C_{19}H_{19}NO_2$ $(M+H^+)$ 294.1494. found 294.1492.

Figure 31:
FIG. 31 depicts the synthesis for compound 64c.

To a solution of amide 64b (FIG. 31) in dimethoxyethane was added p-toluenesulfon-hydrazide (1.1 equivalent) at room temperature. This solution was cooled to 0° C. and anhydrous HCl gas bubbled through the solution for 30 seconds. The reaction mixture was gently refluxed for 3-12 hours (as determined by monitoring by TLC). The solution was cooled first to room temperature at which point a precipitate formed and then further cooled to 0° C. Diethyl ether was added to induce more crystallization. The precipitate was collected by filtration, washed with cold ether, and subsequently allowed to air dry to give pure tosylhydrazone. The resultant white solid was purified by crystallization with diethyl ether to give 64c (83%): $^1$H NMR (500 MHz, $CDCl_3$): δ 8.15 (s, 1H), δ 7.85 (d, 2H, J=8.32 Hz), δ 7.77 (t, 1H, J=1.68 Hz), δ 7.60 (ddd, 1H, J=7.68, 1.08 Hz), δ 7.53-7.54 (m, 3H), δ 7.35-7.46 (m, 4H), 67.27 (d, 2H, J=8.18 Hz), δ 3.70 (t, 2H, J=5.20 Hz), δ 3.21 (t, 2H, J=5.61 Hz), δ 2.37 (s, 3H), δ 1.65 (s, br, 4H), δ 1.45 (s, br, 2H); $^{13}$C NMR (125 MHz, $CDCl_3$): δ 161.9, 150.5, 144.2, 141.8, 140.2, 135.1, 132.7, 129.6, 129.4, 129.2, 128.9, 128.0, 127.7, 127.0, 125.1, 124.8, 47.4, 42.3, 26.4, 25.6, 24.1, 21.5; IR (KBr pellet): 1625, 1448, 1347, 1168 $cm^{-1}$; Mass Spectrum m/z (relative intensity); HRMS calculated for $C_{26}H_{27}N_3O_3S$ (M+Na) 484.1671. found 484.1677.

Figure 32:
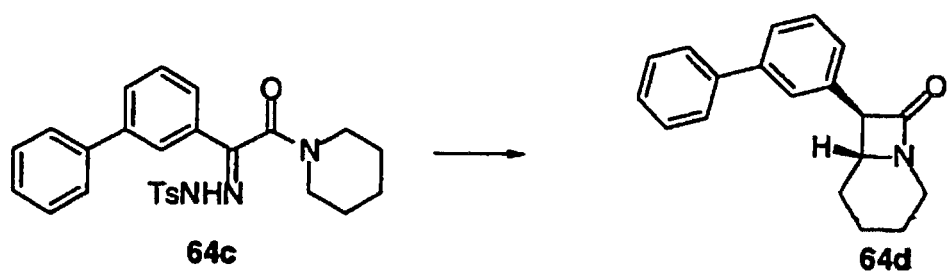
FIG. 32 depicts the synthesis for compound 64d.

To a solution of tosylhydrazone 64c (FIG. 32) in toluene was added a 1 M solution of potassium tert-butoxide in tert-butanol (1.1 equiv.) dropwise at room temperature. The mixture was heated to reflux and monitored by both thin layer chromatography as well as by the color of the reaction mixture. The originally yellow solution turns bright orange as the diazo compound is formed. After 30 minutes at reflux, the solution returns to a yellow color and TLC showed no starting material. The reaction mixture is washed with water (2 times) and then washed with brine. The aqueous portions are combined and extracted with ethyl acetate. The organic extracts were combined, dried over $MgSO_4$, filtered, and evaporated. The resultant orange solid was purified by column chromatography (45% diethyl ether: petroleum ether) to give 64d (78%; threo:erythro 4:1): $^1$H NMR (500 MHz, $CDCl_3$): δ 7.14-7.69 (m, 9H), δ 4.02 (s, 1H), δ 3.89-3.95 (m, 1H), δ 3.39-3.47 (m, 1H), δ 2.75-2.83 (m, 1H), δ 2.17-2.20 (m, 1H), δ 1.90-1.92 (m, 1H), δ 1.62-1.70 (m, 2H), δ 1.30-1.52 (m, 2H); $^{13}$C NMR (125 MHz, $CDCl_3$): δ 166.2, 141.9, 140.9, 136.1, 129.1, 128.7, 127.4, 127.3, 127.2, 127.2, 126.2, 126.2, 126.2, 63.6, 56.9, 39.0, 30.5, 24.5, 22.2; IR (neat): 2939, 2857, 1747, 1650, 1599, 1445, 1403, 1284, 756 $cm^{-1}$; Mass Spectrum m/z (relative intensity); HRMS calculated for $C_{19}H_{19}NO(M+H^+)$ 278.1545. found 278.1543.

Figure 33:
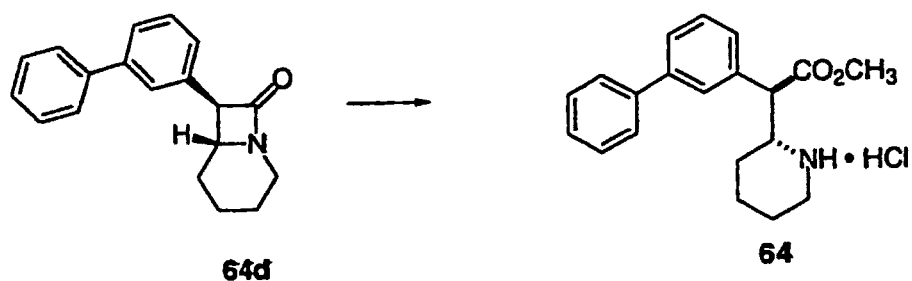
FIG. 33 depicts the synthesis of compound 64.

To a solution of R-lactam 64d (FIG. 33) in MeOH at 0° C., anhydrous HCl gas was gently bubbled through the solution for approximately five minutes. The reaction mixture was allowed to stir at room temperature for 1-5 hours (until all starting material was gone by TLC). The solvent was evaporated and the resultant solid was triturated with ether. The off-white solid was collected by filtration and washed with ether to give the amine salt. The resultant white solid was purified by crystallization with diethyl ether to give 64 (52%): melting point: 190° C. (dec); $^1$H NMR (500 MHz, $CD_3OD$): δ 7.59-7.63 (m, 3H), δ 7.54-7.55 (m, 1H), δ 7.42-7.49 (m, 3H), δ 7.33-7.36 (m, 1H), δ 7.27-7.28 (m, 1H), δ 4.02 (d, 1H, J=9.79 Hz), δ 3.90 (ddd, 1H, J=10.3, 10.3, 2.53 Hz), δ 3.74 (s, 3H), δ 3.44-3.48 (m, 1H), δ 3.11 (ddd, 1H, J=12.78, 12.78. 2.87 Hz), δ 1.78-1.88 (m, 2H), δ 1.68-1.75 (m, 1H), δ 1.43-1.59 (m, 3H); $^{13}$C NMR (125 MHz, $CD_3OD$): δ 173.3, 143.7, 141.5, 135.8, 130.9, 130.0, 128.8, 128.3, 128.2, 128.1, 59.3, 55.3. 53.5, 46.7, 27.7, 23.3, 22.8; IR (KBr pellet): 2949, 1733, 1456, 1436, 1263, 1199, 1168, 1024 $cm^{-1}$; Mass Spectrum m/z (relative intensity); HRMS calculated for $C_{20}H_{23}NO_2$ ($M+H^+$) 310.1807. found 310.1809.

As noted above, published PCT application number WO 99/36403 is also concerned with the Winkler group synthesis. In one portion, this PCT application provides guidance with respect to the synthesis of methylphenidate using the Winkler group synthesis. This guidance will be repeated here, but with reference to FIG. 12 of the Krim thesis.

As reported in PCT application number WO 99/36403, phenyl glyoxylic acid piperidine amide 8 can be prepared by condensation of ethyl phenyl glyoxylate 7 with piperidine as described (Achiwa et al., *Chem. Pharm. Bull.*, 35:2646-2655 (1987)) or by any other method.

Para-toluenesulfonylhydrazide (also designated p-toluenesulfonhydrazide) and tert-butanol are available from commercial sources (e.g., Sigma Chemical Co., St. Louis, Mo.). Potassium tert-butoxide is commercially available both in the form of a solid and in the form of a 1 molar solution in tert-butanol.

The yield of the second intermediate product 9 is improved by subjecting the second reaction mixture to reflux after combining the phenyl glyoxylic acid piperidine amide 8, the p-toluenesulfonylhydrazide, and the acidic solution. Any known method of subjecting the mixture to reflux may be used. By way of example, when the acidic solution of the second reaction mixture is an acidic ethanol solution, the second reaction mixture may be heated by contacting the vessel containing the second reaction mixture with, for example, a temperature-adjustable heating mantle to effect vaporization of ethanol in the vessel. Vaporized ethanol may be condensed using, for example, a jacketed condenser wherein when cold water passes through the jacket of the condenser, vaporized ethanol condenses on the interior surface of the condenser, and the condensed ethanol is returned by the influence of gravity to the vessel. When the second reaction mixture is subjected to reflux, reflux preferably continues for a period of about four hours, although any duration of reflux between about one hour and about four hours may be used.

The second reaction mixture is preferably made by combining a selected molar amount of the phenyl glyoxylic acid piperidine amide 8 and at least about the same molar amount of the p-toluenesulfonylhydrazide. The concentration of the phenyl glyoxylic acid piperidine amide 8 in the second reaction mixture may be, for example, about 2 molar. The concentration of the p-toluenesulfonylhydrazide in the second reaction mixture may also be, for example, about 2 molar. Concentrations of the phenyl glyoxylic acid piperidine amide 8 and the p-toluenesulfonylhydrazide may be as high as the solubility limits of the compounds.

The acidic solution of the second reaction mixture may be any acidic solution in which phenyl glyoxylic acid piperidine amide 8 and p-toluenesulfonylhydrazide are soluble and in which the second intermediate product 9 precipitates. By way of example, the acidic solution may comprise ethanol and an acid such as sulfuric acid or 1,2-dimethoxyethane and acid such as sulfuric acid or hydrochloric acid. Preferably, the acidic solution comprises an acid ethanol solution comprising ethanol and at least a trace amount of sulfuric acid. By "a trace amount of sulfuric acid" is meant a sufficient concentration of acid to catalyze formation of the second intermediate product 9 in the second reaction mixture. By way of example, the concentration of acid which is useful in the second reaction mixture may be from about 1 millimolar to about 20 millimolar. Thus, for example, the concentration of sulfuric acid in the acidic ethanol solution may be from about 1 millimolar to about 20 millimolar.

The second intermediate product 9 may be crystallized and recovered from the second reaction mixture prior to preparation of the third reaction mixture. Any crystallization procedure may be used. The second intermediate product 9 may be crystallized by cooling the second reaction mixture to approximately normal ambient temperature (i.e., circa twenty degrees Celsius). The crystalline form of the second intermediate product 9 may be separated from the second reaction mixture by filtration. Following filtration, the crystalline form of the second intermediate product 9 may be washed using a small amount of cold ethanol (e.g., about 5 milliliters of ethanol at about 25 degrees Celsius to wash about 12 grams of product), a small amount of diethyl ether (e.g., from about 10 to about 20 milliliters to wash about 12 grams of product), and the like. Following such a washing step, the second intermediate product 9 may be air dried prior to preparing the third reaction mixture.

The organic solvent of the third reaction mixture may be any solvent in which the second intermediate product 9 is soluble or may be suspended and which has a boiling point which is sufficiently high to permit generation of a diazo compound and to permit conversion of the diazo compound into a carbenoid intermediate. The organic solvent may, for example, be toluene or 1,4-dioxane.

The deprotonating solution may be any solution which comprises a deprotonating agent which is a sufficiently strong base to deprotonate the hydrazone 9. The deprotonating solution may, by way of example, comprise a salt of tert-butoxide and tert-butanol, a solution of sodium methoxide, a solution of sodium hydroxide, or a solution of potassium hydroxide. Preferably, the deprotonating solution comprises 1.0 molar potassium tert-butoxide in tert-butanol.

The third reaction mixture is preferably made by combining a selected molar amount of the phenyl glyoxylic acid piperidine amide tosylhydrazone 9 and at least about the same molar amount of the deprotonating agent. The concentration of the phenyl glyoxylic acid piperidine amide tosylhydrazone 9 in the third reaction mixture may be, for example, from about 0.1 molar to about 0.5 molar. The concentration of the deprotonating agent in the third reaction mixture may also be, for example, from about 0.1 molar to about 0.5 molar.

The yield of the third intermediate product 10 is improved by subjecting the third reaction mixture to reflux after combining the second intermediate product 9, the deprotonating agent and the organic solvent. Any known method of subjecting the mixture to reflux may be used. By way of example, when the organic solvent of the third reaction mixture is toluene, the third reaction mixture may be heated by contacting the vessel containing the third reaction mixture with, for example, a temperature-adjustable heating mantle to effect vaporization of toluene in the vessel. Vaporized toluene may be condensed using, for example, a jacketed condenser wherein when cold water passes through the jacket of the condenser, vaporized toluene condenses on the interior surface of the condenser, and the condensed toluene is returned by the influence of gravity to the vessel. When the third reaction mixture is subjected to reflux, reflux preferably continues for a period of at least about ninety minutes, although any duration of reflux between about thirty minutes and about two hours may be used, the duration of reflux being variable, depending on how long it must be maintained to permit the reaction to proceed to completion.

The third intermediate product 10 may be crystallized and recovered from the third reaction mixture prior to preparation of the fourth reaction mixture. Any crystallization procedure may be used. By way of example, the third intermediate product 10 may be crystallized by cooling the third reaction mixture to approximately normal ambient temperature (i.e., about 20 degrees Celsius). The third reaction mixture may be 'washed' by combining it with a composition comprising water to form an aqueous phase and an organic phase. The organic phase may be separate from the aqueous phase. This 'washing' procedure may be repeated several times. The organic phase may be dried by sealing it in a container which contains a desiccant such as magnesium sulfate. The organic phase may then be filtered, and the organic solvent may be evaporated. The 'dried' third reaction mixture may be combined with organic solvents such as diethyl ether and light petroleum ether to form a precipitation mixture. The third intermediate product 10 precipitates in the precipitation mixture.

Precipitation of the third intermediate product 10 in the precipitation mixture may be accelerated using known methods, such as cooling the precipitation mixture, scratching the interior surface of a glass vessel containing the precipitation mixture using a glass rod, seeding the precipitation mixture, and the like. The crystalline third intermediate product 10 may be separated from the precipitation mixture using any known method, such as filtration. Separation of the third intermediate product 10 from the precipitation mixture may be improved by 'washing' the crystalline third intermediate product 10 using a solvent such as light petroleum ether and air drying the product. Furthermore, the yield of the crystalline third intermediate product 10 from the precipitation mixture may be improved by evaporating liquid from the precipitation mixture and crystallizing the third intermediate product 10 therefrom, as described herein.

In the fourth reaction mixture, it is preferable to combine a selected molar amount of the third intermediate product 10 with a molar excess of methanol.

The acidified methanol solution of the fourth reaction mixture preferably comprises HCl. When the acid of the acidified methanol solution is HCl, the concentration of HCl in the acidified methanol solution is preferably about equal to the concentration of HCl in a solution of methanol saturated with HCl gas at zero degrees Celsius.

The yield of threo-methylphenidate 6 is improved by subjecting the fourth reaction mixture to reflux after combining the third intermediate reaction product 10 and the acidified methanol solution. Any known method of subjecting the mixture to reflux may be used. By way of example, the fourth reaction mixture may be heated by contacting the vessel containing the fourth reaction mixture with, for example, a temperature-adjustable heating mantle to effect vaporization of methanol in the vessel. Vaporized methanol may be condensed using, for example, a jacketed condenser wherein when cold water passes through the jacket of the condenser, vaporized methanol condenses on the interior surface of the condenser, and the condensed methanol is returned by the influence of gravity to the vessel. When the fourth reaction mixture is subjected to reflux, reflux preferably continues for a period of at least about thirty minutes, although any duration of reflux between about thirty minutes and about two hours may be used, although the duration of reflux may vary, depending on how long the reaction must be maintained to permit the reaction to proceed to completion. The fourth reaction mixture may also be prepared and permitted to react at about 25 degrees Celsius.

Threo-methylphenidate 6 (FIG. 11) may be separated from the fourth reaction mixture using any known method for removing methanol and acid from a composition. By way of example, methanol may be evaporated from the fourth reaction mixture. A solvent such as ethyl acetate may be mixed with the residue, and the mixture may be triturated. The triturated mixture may be diluted with a solvent such as diethyl ether. Crystalline threo-methylphenidate 6 may be separated from the solvents using any known method, such as filtration, and may thereafter be air dried.

Example 1 of PCT application number WO 99/36403 describes the synthesis of threo-methylphenidate, including specific amounts of materials and specific reaction conditions. The synthesis was performed as follows.

Phenyl glyoxylic acid piperidine amide was prepared by condensation of ethyl phenyl glyoxylate with piperidine as described in Achiwa et al., *N. Chem. Pharm. Bull.,* 35:2646-2655 (1987).

Then, a first reaction mixture comprising 8.50 grams (0.039 mole) phenyl glyoxylic acid piperidine amide, 8.00 grams (0.043 mole) p-toluenesulfonylhydrazide, and 20 milliliters of an acidic solution, which comprised ethanol and a trace of sulfuric acid, was prepared and subjected to reflux for about four hours. The first reaction mixture was cooled to room temperature (i.e., about 20 degrees Celsius). After cooling, a white crystalline first intermediate product comprising phenyl glyoxylic acid piperidine amide tosylhydrazone was present in the first reaction mixture. The first reaction mixture was filtered to separate the crystalline first intermediate product from the first reaction mixture. The crystalline first intermediate product was washed in situ on the filter with a small amount of cold ethanol (i.e., about 5 milliliters at about 25 degrees Celsius) and then with a small amount of diethyl ether (i.e., about 10-25 milliliters). Following these washing steps, the crystalline first intermediate product was air dried on the filter. The yield of the first intermediate product was 12.0 grams, representing an 81% reaction yield. The properties of the first intermediate product were: Melting point: 191-193° C. (decomposes): $^1$H NMR (500 MHz, CDCl$_3$) (chemical shift values in parts per million): 8.48 (s, 1H), 7.80 (d, 2H, J=8.2 Hz), 7.55 (m, 2H), 7.31-7.35 (m, 3H), 7.19 (d, 2H, J=8.2 Hz), 3.65 (app t, 2H, J=5.3 Hz), 3.14 (app t, 2H, J=5.5 Hz), 2.28 (s, 3H), 1.60 (m, 4H), 1.40 (m, 2H); $^{13}$C NMR (125 MHz, CDCl$_3$) (chemical shift values in parts per million): 161.9, 150.6, 144.0, 135.1, 132.1, 130.5, 129.5, 128.7, 127.9, 126.2, 47.3, 42.1, 26.2, 25.5, 24.1, 21.4; IR (KBr pellet): 1623.3, 1163.1 cm$^{-1}$; High resolution mass spectrum (HRMS) calculated for $C_{20}H_{23}N_3O_3S$ (M+NH$_4$): 403.1804. found 403.1809.

Next, a second reaction mixture was prepared comprising 9.25 grams (0.024 mole) phenyl glyoxylic acid piperidine amide tosylhydrazone, 200 milliliters of toluene, and 24.5 milliliters of a deprotonating solution comprising 1.0 molar potassium tert-butoxide in tert-butanol. After combining the components of the second reaction mixture, the second reaction mixture became a clear orange liquid upon heating. The second reaction mixture was then subjected to reflux for about ninety minutes, during which time the orange color attributable to the phenyl glyoxylic acid piperidine amide tosylhydrazone gradually disappeared and a precipitate comprising potassium p-toluensulfinate formed. After cooling the second reaction mixture to room temperature, the second reaction mixture was mixed with 50 milliliters of water to form a mixture having an aqueous phase and an organic phase. The organic phase was separated from the aqueous phase, and the aqueous phase was discarded. The organic phase was mixed with 50 milliliters of water and was again separated from the aqueous phase of the mixture. The organic phase was dried by sealing the organic phase in a container which contained magnesium sulfate. Following drying, the organic phase was filtered and evaporated to yield 5.27 grams of a pale yellow oil. The pale yellow oil was dissolved in 10 milliliters of diethyl ether, and 15 milliliters of light petroleum ether was gradually added to the solution with swirling to yield a precipitation mixture. Upon standing at room temperature, the second intermediate product, which comprised trans-1-aza-2-oxo-3-phenyl-bicyclo [4.2.0]octane, crystallized in the precipitation mixture. In some preparations, scratching of the container containing the precipitation mixture or seeding of the precipitation mixture was required. The precipitation mixture was cooled to about 5 degrees Celsius in a refrigerator, and the second intermediate product was collected by filtration, washed with a small amount (i.e. about 10 milliliters) of light petroleum ether, and air dried. The yield of the second intermediate product was 2.90 grams, representing a 60% yield with respect to the first intermediate product. Additional second intermediate product could be obtained by evaporating the precipitation mixture and crystallizing the second intermediate product as described. The second intermediate product had the following properties: Melting point: 87° C.; $^1$H NMR (500 MHz, CDCl$_3$) (chemical shift values in parts per million): 7.29-7.32 (m, 2H), 7.21-7.27 (m, 3H), 3.94 (d, 1H, J=1.5 Hz), 3.90 (app dd, 1H, J=13.3, 4.3 Hz), 3.34 (m, 1H), 2.77 (m, 1H), 2.15 (m, 1H), 1.89 (m, 1H), 1.66 (m, 1H), 1.34-1.46 (m, 3H); $^{13}$C NMR (125 MHz, CDCl$_3$) (chemical shift values in parts per million): 166.1, 135.5, 128.6, 128.4, 127.1, 63.3, 56.6, 38.8, 30.4, 24.3, 22.1; IR (KBr pellet): 1745.7, 1399.1 cm$^{-1}$; HRMS calculated for C$_{13}$H$_{15}$NO (M+H): 202.1232. found 202.1226. The trans-stereochemistry of the second intermediate product was established by X-ray crystallographic analysis, using known methods.

A third reaction mixture was prepared comprising 10 milliliters of HCl-saturated methanol and 0.50 gram (0.00248 mole) trans-1-aza-2-oxo-3-phenyl-bicyclo [4.2.0] octane. HCl-saturated methanol was prepared by saturating methanol with HCl gas while cooling the methanol in an ice water bath. The third reaction mixture was subjected to reflux for from about thirty to about ninety minutes, which permitted the reaction to proceed to completion. HCl-saturated methanol was evaporated, 5 milliliters of ethyl acetate was added to the residue, and the residue was triturated. The mixture of triturated residue and ethyl acetate was diluted by adding 10 milliliters of diethyl ether to the mixture. The residue, comprising threo-methylphenidate, was collected by filtration, washed with a small amount (i.e. about 10-20 milliliters) of diethyl ether and air dried. The yield of the product was 600 milligrams, which represents a 90% yield of threo-methylphenidate from trans-1-aza-2-oxo-3-phenyl-bicyclo [4.2.0] octane. The product, threo-methylphenidate, had the following properties: Melting point: 206° C.; $^1$H NMR (500 MHz, D$_2$O) (chemical shift values in parts per million): 7.34-7.40 (m, 3H), 7.24-7.27 (m, 2H), 3.92 (d, 1H, J=9.2 Hz), 3.76 (m, 1H), 3.65 (s, 3H), 3.38 (broad d, 1H, J=12.8 Hz), 3.00 (dt, 1H, J=12.9, 3.1 Hz), 1.79 (m, 1H), 1.70 (m, 1H), 1.49-1.60 (m, 2H), 1.26-1.41 (m, 2H); $^{13}$C NMR (125 MHz, D$_2$O) (chemical shift values in parts per million): 173.1, 133.2, 129.4, 128.8, 128.6, 57.7, 53.6, 53.2, 45.5, 26.2, 21.7, 21.2; IR (KBr pellet): 2400-3000 (broad), 1738.8, 1429.9, 1171.8 cm$^{-1}$: HRMS calculated for C$_{14}$H$_{19}$NO$_2$ (M+H): 234.1494. found 234.1489.

Example 2 of PCT application number WO 99/36403 teaches that the following synthetic procedures were used to generate methylphenidate analogs. All of the procedures were performed in flame-dried glassware which had been purged with argon. The melting point of individual compounds was assessed using a Thomas Hoover capillary melting point apparatus. Infrared spectra were recorded using a Perkin-Elmer 1600 series Fourier transform infrared spectrometer $^1$H and $^{13}$C NMR spectra were recorded using a Bruker AM-500 spectrometer. High resolution mass spectra were assessed using a VG Micromass 7070H high resolution chemical ionization spectrometer equipped with a Kratos DS-50-S data handling system.

First, Example 2 of PCT application number WO 99/36403 teaches that methylphenidate analogs can be prepared by the following method (corresponding to FIGS. 16 and 19 of the Krim thesis):

Aryl α-Keto Ester Formation

A 2.5 molar solution of a selected, freshly titrated n-butyllithium in hexanes was added dropwise at room temperature to 1 equivalent of a 2 molar solution of a selected aryl halide dissolved in a 1:1 mixture of anhydrous diethyl ether and anhydrous toluene. This solution was stirred for 15 minutes at room temperature and then stirred at 45-55° C. for 30 minutes. In a separate flask, 4 equivalents of diethyloxalate in 3 molar anhydrous diethyl ether was cooled to −78° C. To this cooled solution, the aryllithium was added dropwise using a cannula, and the mixture was stirred at −78° C. for 1 hour. To quench the reaction, 2 normal HCl was added dropwise to the mixture at 0° C. Distilled water was then added to further dissolve the salts formed, and the resulting aqueous layer was extracted using ether. The ether extracts were washed with water, dried over MgSO$_4$, filtered and evaporated. Excess diethyloxalate was removed from the crude aryl α-keto ester product by short path distillation at a pressure of 1 millimeter of mercury. The resulting material was purified by column chromatography to yield the purified aryl α-keto ester.

α-Keto Amide Formation

A neat mixture of a selected amine and the aryl α-keto ester (equimolar amounts of each) was stirred at 90-100° C. for 2-5 days. The resulting oil was triturated or, alternatively, purified by column chromatography to yield the α-keto amide.

α-Tosylhydrazone Formation

To a solution of the α-keto amide dissolved in dimethoxyethane was added 1.1 equivalent of p-toluenesulfonhydrazide at room temperature. This solution was cooled to 0° C., and anhydrous HCl gas was bubbled through the solution for 30 seconds. The reaction mixture was gently refluxed for 3-12 hours, as determined by monitoring by thin layer chromatography. The solution was cooled, first to room temperature, at which point a precipitate formed, then further cooled to 0° C. Diethyl ether was added to induce further crystallization. The precipitate was collected by filtration, washed with cold ether, and subsequently allowed to air dry to yield the pure tosylhydrazone. The tosylhydrazone was recrystallized in a 3:1 mixture of ether:ethanol to yield needle-like crystals of the α-tosylhydrazone.

β-Lactam Formation

To a solution of the α-tosylhydrazone in toluene was added 1.1 equivalent of a 1 molar solution of potassium tert-butoxide in tert-butanol. This solution was added dropwise at room temperature. The mixture was heated to reflux and monitored by both thin layer chromatography and the color of the reaction mixture. The originally yellow solution turned bright orange as the diazo compound was formed. After 30 minutes at reflux, the solution re-assumed a yellow color and TLC indicated that no starting material was present. The reaction mixture was washed twice with water, and then washed with brine. The aqueous portions were combined and extracted with ethyl acetate. The organic extracts were combined, dried over $MgSO_4$, filtered and evaporated. The resulting oil (or semi-solid, in some experiments) was purified by flash column chromatography. If the product was solid, further purification by recrystallization from ether was performed to yield a single diastereomer in the form of white crystals of the β-lactam.

Amine Salt Formation

Anhydrous HCl gas was gently bubbled through a solution of the β-lactam in MeOH at 0° C. for approximately five minutes. The reaction mixture was stirred for 1-5 hours at room temperature, until thin layer chromatography indicated that all starting material had been consumed. The solvent was evaporated, and the remaining solid was triturated with ether. The off-white solid was collected by filtration, washed with ether, and recrystallized in a methanol-ether mixture to yield white crystals of the amine salt.

Second, Example 2 of PCT application number WO 99/36403 also teaches that methylphenidate analogs can be prepared by a second method (corresponding to FIG. 20 of the Krim thesis):

Alkylation of 1-Aza-Bicyclo[4.2.0]octan-8-one

Methylphenidate analogs may, alternatively, be made by alkylating a 1-aza-bicyclo ketone as illustrated by benzylation of 1-aza-bicyclo[4.2.0]octan-8-one. A solution of the β-lactam 1-aza-bicyclo[4.2.0]octan-8-one in tetrahydrofuran (THF) was added dropwise to a freshly prepared solution of lithium diisopropanolamine (LDA; 1.5 equivalents) in THF which had been pre-cooled to −78° C. The enolate was formed by allowing the reaction to proceed for 20 minutes at −78° C., at which point 1.5 equivalents of benzyl bromide were added dropwise. The reaction mixture was warmed to 0° C. and stirred for an additional 30 minutes. The alkylation reaction was quenched by slow addition of water to the reaction mixture. The organic and aqueous layers were separated, and the aqueous layer was washed using ethyl acetate. The organic portions were combined, washed with brine, dried over $MgSO_4$, filtered and evaporated to yield a single diastereomer of the alkylated lactam which was subsequently purified by column chromatography. The lactam was then opened with hydrochloric acid and methanol to provide the desired analog.

Pan et al., *Eur. J. Pharmacol.*, 264:177-182 (1994) ("Pan") describes the synthesis of bromine-substituted methylphenidate analogs. In particular, Pan describes the synthesis of the o-bromo, m-bromo and p-bromo methylphenidate (bromo substitutents on the phenyl ring). The Panizzon synthesis of methylphenidate was modified to prepare p-bromomethylphenidate. Briefly, methylphenidate's molecular skeleton was prepared by base catalyzed reaction of p-bromophenylacetonitrile with o-chloropyridine. Following hydrolysis of the nitrile group to an amide, the pyridine ring was reduced to produce a 4:1 mixture of the erythro and threo isomers of ritalinic acid amide. Epimerization with NaOH, acid hydrolysis of the amide, and treatment with methanol/hydrogen chloride then gave dl-threo-p-bromomethylphenidate hydrochloride in about 10% overall yield. An early batch used in in vivo experiments was about 85% pure due to the presence of erythro isomers of p-bromomethylphenidate and a trace of dl-threo-methylphenidate. These impurities were removed by several recrystallizations from methanol/ether before in vitro binding experiments were performed. Nuclear magnetic resonance (NMR) spectroscopic data were consistent with the assigned structure (63.26 doublet for the benzylic hydrogen showing the threo configuration; 67.18 and 7.44 doublets for the aromatic protons) and a purity of >98%. Chiral high performance liquid chromatography (HPLC) using a Daicel 250×10 mm column eluted with hexane-isopropanol-diethylamine (98:2:0.1, v/v at 4 ml/min) showed two peaks of equal area at 10 and 12 minutes. The analogous o- and m-bromo derivatives were also prepared from the corresponding o- and m-bromophenylacetonitriles, and shown by NMR and chiral HPLC to be >95% pure.

Gatley et al., *Life Sciences,* 58:231-239 (1996) ("Gatley") describes the synthesis of several methylphenidate derivatives substituted on the phenyl ring. The o-bromo, m-bromo and p-bromo methylphenidate derivatives were prepared as described in Pan et al., *Eur. J. Pharmacol.*, 264:177-182 (1994). The procedures of Patrick et al., were used to prepare p-hydroxy and p-methoxy-methylphenidate, and to resolve d-threo- and l-threomethylphenidate (Patrick et. al., *J. Med. Chem.*, 24:1237-1240 (1981) and Patrick et al., *J. Pharmacol. Exp. Ther.*, 241:152-158 (1987)). p-Iodomethylphenidate was prepared from methylphenidate via nitration and diazotization. m-Iodo-p-hydroxymethylphenidate was synthesized by electrophilic iodination of p-hydroxy-methylphenidate. All the methylphenidate analogs were obtained as the crystalline hydrochlorides and stored at 0-4 degrees.

Deutsch et al., *J. Med. Chem.*, 39:1201-1209 (1996) ("Deutsch") reports that several methylphenidate derivatives substituted on the phenyl ring have been synthesized by others. These were the 4-OH, 3,4,5-tri-MeO, 2-Br, 3-Br, 4-Br, 4-OMe and 3-1,4-OH derivatives. See Faraj et al., *J. Pharmacol. Exp. Ther.*, 191:535-547 (1974); Patrick et al., *J. Med. Chem.*, 24:1237-1240 (1981); Wolters et al., *J. Pharm. Sci.*, 64:2013-2014 (1975); Pan et al., *Eur. J. Pharmacol.*, 264:177-182 (1994); Chaturvedi et al., *Soc. Neurosci. Abst.*, 20(1), no. 381.15 (1994). Also a series of alkyl esters had been synthesized. See Portoghese and Malspeis, *J. Pharm. Sci.*, 50:494-501 (1961).

Deutsch et al., *J. Med. Chem.*, 39:1201-1209 (1996) ("Deutsch") also describes the synthesis of several additional methylphenidate derivatives substituted on the phenyl ring. Synthesis was accomplished by alkylation of 2-bromopyridine with anions derived from various substituted phenylacetonitriles. A summary of this method is shown in the reaction scheme found in FIG. 34. Also see the discussion of the Deutsch method above (from the Krim thesis).

Several significant modifications in the literature procedures were made in order to make the reaction scheme (FIG. 34) more efficient. The original method of Panizzon called for the use of sodium amide in toluene and 2-chloropyridine for the first step; most subsequent workers have used this method. As reported by Deutsch, this procedure often gives mixtures of products which sometimes required difficult chromatographic separations. In addition, certain substituent groups would be expected to be incompatible with these conditions. As reported by Deutsch, the use of potassium tert-butoxide in tetrahydrofuran (THF) and 2-bromopyridine worked better. The ketone byproducts 4 that were sometimes produced are easily removed in the next step. The use of concentrated hydrochloric acid was preferable to the standard condition of concentrated sulfuric acid for the hydrolysis of the nitriles 3 to the amides 5. The yields were generally higher, and the problem of aromatic ring sulfonation, when X=OCH$_3$, was avoided. Most workers have used the piperidine amides 6 and 7 in the 50% KOH epimerization procedure; this was found by Deutsch to be very unreliable. Variable results from run to run and low yields were often obtained. When the amides were first hydrolyzed and the acids 8 used for epimerization, the reaction proceeded much more reliably. Interestingly, the acids formed an insoluble "oil" in the 50% KOH solution. For the 2-chloro compound, base-catalyzed epimerization did not work well. However, treatment with 6N HCl under reflux for three days produced a threo/erythro ratio of 60:40. In all cases except the 2-hydroxyl compound, the desired threo isomer was obtained by crystallization of the mixture of hydrochloride salts of the methylphenidate derivatives 1 and 11 from various solvents. In several cases the pure erythro amides 6 were isolated by crystallization or simple solvent washing. They were hydrolyzed to the erythro acids 10 with a small amount of epimerization (ca. 10%) and then converted to methyl esters from which the pure erythro methylphenidate analogs could be isolated by crystallization.

The alkylation procedure above failed for 4-nitro- and 4-(trifluoromethyl)-phenylacetonitrile. No condensation product could be isolated. Apparently, the intermediate enolates from these compounds are not reactive enough toward the relatively poor electrophile 2-bromopyridine. With 2-amino-phenylacetonitrile, only the 2-aminoindole could be isolated (this compound does not appear to be described in the literature and its structure is based on the IR, MS, and $^1$H-NMR spectral data). (±)-threo-4-Nitromethylphenidate (1v) was synthesized by the direct nitration of (±)-threo-methylphenidate with fuming nitric acid. The product of this reaction was difficult to purify because of the formation of the 3-nitro isomer (presumed impurity based on [$^1$H]-NMR analysis).

The 50% KOH epimerization step worked best with the acids 8 rather than the amides 6 and 7. The potassium salts of 8 are insoluble in 50% KOH and float on top as an "oil." This oil is relatively easy to separate, and after esterification the contaminating inorganics can be separated from the free base. After epimerization, the threo/erythro ratio (9:10) varied from about 1:1 for 4-tert-butyl and 3,4-dimethoxy to about 20:1 for 2-fluoro, but was generally about 4:1. The less soluble threo hydrochloride salt was easily separated by crystallization. In cases where less of the threo isomer was produced, purification was more difficult.

The assignment of threo and erythro to the isomers of methylphenidate congeners was based on several factors. First, by analogy with 1a, the hydrogenation step (5 to 6 and 7) would be expected to produce a preponderance of the erythro isomers in all cases. In fact, the hydrogenation reaction always produced an approximate 80/20 mixture of isomers. Further analysis of these mixtures was always consistent with the major isomer being erythro. Also, based on $^1$H-NMR analysis of the intermediates and final products in the synthesis of 1a, a clear pattern for the two isomers was evident. This pattern was confirmed in all of the congeners synthesized in this study.

Significant refinements of the literature conditions by Deutsch gave a synthetic scheme which was more reproducible with higher overall yields. Both erythro and threo isomers of methylphenidate analogs can be produced by this method. A summary of selected properties of the compounds synthesized in this study are shown in FIG. 35.

Figure 34:
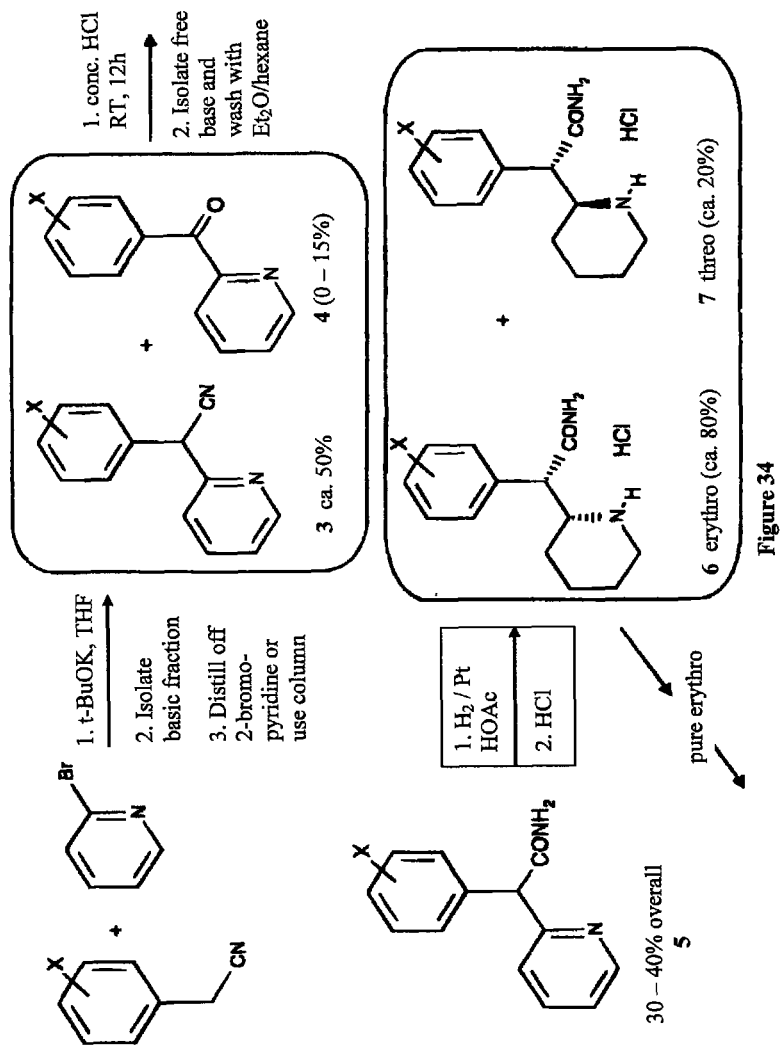
FIG. 34 shows the synthesis of several additional methylphenidate derivatives substituted on the phenyl ring, which was accomplished by alkylation of 2-bromopyridine with anions derived from various substituted phenylacetonitriles.
Figure 34:
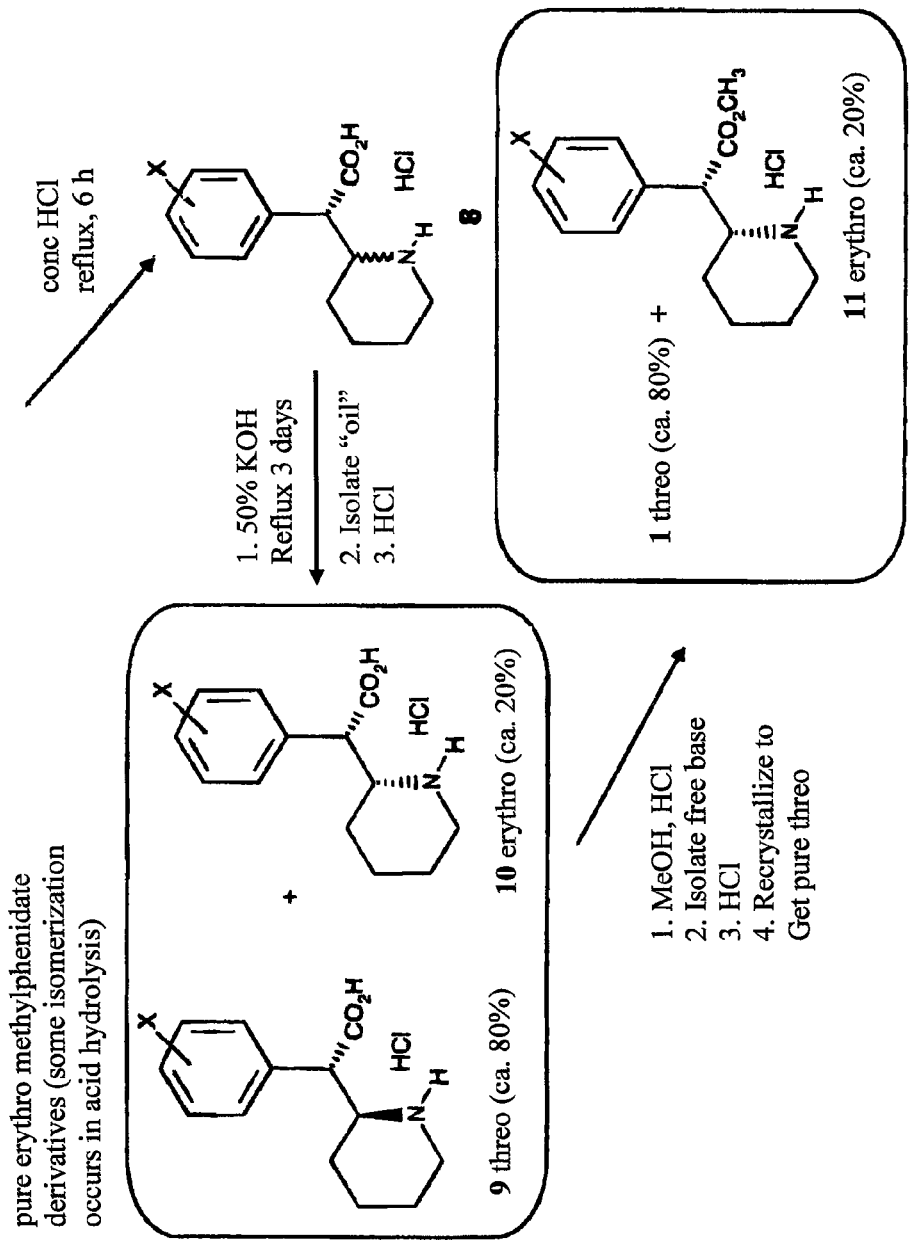

Deutsch also includes detailed experimental procedures for the synthesis of the methyphenidate derivatives. Some of these procedures are described below. Refer to FIG. 34 and FIG. 35.

Chemistry General

Reagents and solvents were mostly reagent grade and were used without further purification. Solvents or reagents that required drying or purification were prepared according to the procedures found in Vogel. Furniss, et al., eds.; *Vogel's Textbook of Practical Organic Chemistry*, 5$^{th}$ ed., (Wiley, New York, 1989). Column chromatography was carried out on Fisher Scientific Co. silica gel (Grade 62) or Fisher Scientific neutral alumina (60-325 mesh). Melting points were obtained using a Laboratory Devices Mel-Temp II instrument without corrections. Nuclear magnetic resonance spectra were recorded on a Varian Gemini 300 (300 MHz) NMR spectrometer. Mass spectra were measured on a VG 70-SE, 2 sector, forward geometry instrument. IR spectra were recorded on a Nicolet 520 FT spectrophotometer. Microanalytical data were obtained by Atlantic Microlabs, Atlanta, Ga.

Synthesis of Methyl (±)-threo- and -erythro-(3-Chlorophenyl)(2-piperidyl)acetates (1k and 11d). Typical Reaction Conditions for the Synthesis of Methylphenidate Analogs: (3-Chlorophenyl)(2-pyridyl)acetonitrile (3, X=3-Cl)

To a stirred solution of 12.3 g (0.110 mol) of t-BuOK in 60 mL of dry THF under dry N$_2$ gas was slowly added 11.8 mL (15.2 g, 0.100 mol) of 3-chlorobenzyl cyanide in 25 mL of dry THF. The mixture was stirred at room temperature for 0.5 h, and 15.8 g (9.50 mL, 0.100 moles) of 2-bromopyridine in 20 mL of dry THF was added dropwise during 1 h. The mixture was stirred at room temperature for another 1 h and then heated under reflux overnight. The THF was evaporated and 100 mL of water added while cooling with an ice bath. The aqueous layer was extracted with 3×100 mL of EtOAc, and the organic layer was washed with water and then extracted with 4×70 mL of 6 N HCl solution. The aqueous layer was then made basic with 15% NaOH solution to a pH of >11 and extracted with 3×200 mL of EtOAc; the organic layer was washed with water and dried to give a mixture that was crystallized from hexane/EtOAc (1:1) to yield 7.73 g (33.9%) of 3 as colorless crystals: mp 83.3-84.3° C.; $^1$H NMR (CDCl$_3$) δ 8.63 (dd, J=2.6, 1.5 Hz, 1H), 7.8 (td, J=7.8, 1.8 Hz, 1H), 7.45-7.26 (m, 6H), 5.29 (s, 1H); MS-CI m/z 229 (M+1, 100). Alternatively, 2-bromopyridine can be distilled out of the mixture to give impure 3 (ca. 50%) containing 7% (by $^1$H NMR analysis) of the ketone 4 (X=3-Cl).

(3-Chlorophenyl)(2-pyridyl)acetamide (5, X=3-Cl)

With stirring, 1.00 g (4.40 mmol) of 3 (X=3-Cl) was dissolved in 10 mL of 12 N HCl, heated to 40° C., and then stirred at room temperature for 15 h. The solution was poured into 50 mL of ice-water and then adjusted to a pH of 10-11 with 15% NaOH solution. The mixture was extracted with 3×40 mL of CH$_2$Cl$_2$, washed with 50 mL of water, and dried to give 0.97 g (89%) of 5 as a colorless solid: mp 97.2-98.4° C.; $^1$H NMR (D$_2$O) δ 8.61 (d, J=5.0 Hz, 1H), 7.87 (s, br, 1H), 7.68 (td, J=7.8, 1.7 Hz, 1H), 7.44 (s, 1H), 7.34-7.23 (m, 5H), 6.21 (s, br, 1H), 4.98 (s, 1H); MS-EI m/z 246 (M+, 3.4), 203 (100), 167 (71).

erythro- and threo-(3-Chlorophenyl)(2-piperidyl)-acetamides (6 and 7, X) 3-Cl)

To a solution of 0.43 g (1.7 mmol) of 5 (X=3-Cl) in 15 mL of HOAc was added 0.14 g of 5% Pt/C. This mixture was treated with $H_2$ gas at 30-40 psi for 10 h. The catalyst was removed by filtration and the filtrate evaporated to dryness. Excess concentrated HCl was then added and the mixture again evaporated to dryness to give 0.48 g (98%) of compounds 6 and 7 (83:17 by $^1$H NMR analysis); washing with EtOH gave 0.29 g (60%) of pure 6 as a white solid: mp 238.7-239.0° C.; $^1$H NMR ($D_2O$) δ 7.34-7.19 (m, 4H), 3.66-3.57 (m, 2H), 3.17-3.13 (m, 1H), 2.83-2.79 (m, 1H), 1.96-1.92 (m, 1H), 1.74-1.70 (m, 2H), 1.47-1.40 (m, 3H); MS-CI m/z 253.1 (91, M+1-HCl), 170.0 (100).

erythro- and threo-(3-Chlorophenyl)(2-piperidyl) acetic Acids (8, X=3-Cl)

A mixture of 5.20 g (0.018 mol) of 6 and 7 (X=3-Cl) and 100 mL of 6 N HCl solution was heated under reflux for 6 h. The solution was evaporated to dryness to give compounds 8 (71:29 erythro:threo by $^1$H NMR analysis, containing some $NH_4Cl$): $^1$H NMR ($D_2O$) δ 7.33-7.08 (m, 4H), 3.73 (d, J=8.9 Hz, 1H), 3.62-3.56 (m, 1H), 3.31-3.13 (m, 1H), 2.91-2.75 (m, 1H), 1.99-1.22 (m, 6H); MS-CI m/z 254.1 (57, M+1-HCl), 171.0 (100).

threo- and erythro-(3-Chlorophenyl)(2-piperidyl) acetic Acids (9 and 10, X=3-Cl)

Under a $N_2$ atmosphere, the above mixture of compounds 8 (X=3-Cl, ca. 0.018 mol) were mixed with 80 mL of 50% KOH solution and heated under reflux for 4 days, in a Teflon cup. The top oily layer was separated, dissolved in $CH_3OH$, acidified with concentrated HCl, and evaporated to dryness to give compounds 9 and 10 (83:17 by $^1$H NMR analysis): $^1$H NMR ($D_2O$) δ 7.31-7.08 (m, 4H), 3.84 (d, J=9.2 Hz), 3.74 (d, J=9.0 Hz), 3.63-3.56 (m, 1H), 3.32-3.17 (m, 1H), 2.96-2.85 (m, 1H), 1.73-1.18 (m, 6H).

Methyl threo-(3-Chlorophenyl)(2-piperidyl)acetate (1k)

To a solution of the above mixture of 9 and 10 (X=3-Cl, ca. 0.018 mol) in 193 mL of absolute $CH_3OH$ was slowly added 8 mL of $SOCl_2$, while cooling with an ice bath. The mixture was stirred at room temperature for 1 day and evaporated, water added, and the pH adjusted to ca. 11 with 15% NaOH solution. The mixture was extracted with 3×120 mL of EtOAc and the organic layer washed with $H_2O$ and dried. Removal of solvent gave 3.53 g (74% from compounds 6 and 7) of the free base of compounds 1 and 11 (91:9 by $^1$H NMR analysis) which was dissolved in MeOH, and excess concentrated HCl was then added, and the mixture was evaporated to dryness to give a white solid, which was washed with $Et_2O$ and EtOAc to give 3.16 g (90%) of pure 1 (by $^1$H NMR analysis). The analytical sample was recrystallized from MeOH: mp 197.0-197.9° C.; $^1$H NMR ($D_2O$) δ 7.31-7.23 (m, 3H), 7.11-7.08 (m, 1H), 3.84 (d, J=9.4 Hz, 1H), 3.71-3.64 (m, 1H), 3.58 (s, 3H), 3.33-3.27 (m, 1H), 2.93-2.89 (m, 1H), 1.69-1.22 (m, 6H); MS-CI m/z 268.2 (100, M$^+$+1-HCl). Anal. Calcd for $C_{14}H_{19}Cl_2$—$NO_2$: C, H, N, Cl.

Methyl erythro-(3-Chlorophenyl)(2-piperidyl)acetate (11d)

A mixture of 0.25 g (0.87 mmol) of compound 6 (X=3-Cl) and 10 mL of 6 N HCl solution was heated under reflux for 6 h. The solution was evaporated to dryness to give 9 and 10 (14:86 by $^1$H NMR analysis), which were mixed with 11 mL of $CH_3OH$ and 0.5 mL of $SOCl_2$. Using a procedure similar to that used for 1 and 11 above, this gave 0.20 g (86%) of the free base of 1 and 11 as a colorless oil which was dissolved in MeOH, and excess concentrated HCl was then added; evaporation to dryness gave a white solid, which was then recrystallized with MeOH/EtOAc (1:2) to give 0.125 g (overall yield 47%) of pure 11 (by $^1$H NMR analysis) as colorless crystals: mp 199.8-200.2° C.; $^1$H NMR ($D_2O$) δ 7.34-77.25 (m, 3H), 7.14 (m, 1H), 3.82 (d, J=8.9 Hz, 1H), 3.68-3.62 (m, 1H), 3.56 (s, 1H), 3.16-3.11 (m, 1H), 2.83-2.75 (m, 1H), 1.92-1.36 (m, 6H); MS-CI, m/z 268.1 (100, M+1-HCl). Anal. Calcd for $C_{14}H_{19}Cl_2NO_2$: C, H, N, Cl.

Isolation of Representative Ketone 4 (X=3-OMe)

A 45% yield of impure 3 (X=3-OMe) containing some 4 was obtained from 3-methoxyphenylacetonitrile and 2-bromopyridine according to the above general procedure (after removal of unreacted 2-bromopyridine by distillation). Impure 3 was mixed with concentrated HCl to give impure 5 (X=3-OMe) containing 4. This mixture was placed on an alumina column and eluted with EtOAc/hexane (2:1) which gave, in the early fractions, a 9% yield of 4 as a yellow oil: $^1$H NMR (CDCl$_3$) δ 8.73 (d, J=6.5 Hz, 1H), 8.03 (d, J=7.7 Hz, 1H), 7.91 (td, J=7.7, 1.5 Hz, 1H), 7.65-7.62 (m, 2H), 7.52-7.48 (m, 1H), 7.40 (t, J=8.2 Hz, 1H), 7.16 (dd, J=8.6, 2.6 Hz, 1H), 3.87 (s, 3H); MS-EI m/z 213 (M$^+$, 70), 135 (100).

Nitration of 1a. Compound Iv (X=4-NO$_2$)

To 30 mL of fuming nitric acid at −10° C., was added 3.9 g (0.015 mol) of ((±)-threo-ritalinic acid. After stirring for 15 min, ice was added and then ammonium hydroxide until pH=7. The solid was collected, washed with water, and dried to give 3.1 g (71%) of crude product. A portion (0.50 g) was converted to the methyl ester in the standard manner to yield 0.46 g (87%) of crude hydrochloride salt. Careful crystallization from acetone gave 0.066 g of pure 1 (R=4-NO$_2$). Anal. Calcd for $C_{14}H_{19}$—$ClN_2O_4$: C, H, N, Cl.

Demethylation of Methoxy Compounds

Each pure (±)-threo-methoxy compound was mixed with excess 48% HBr and refluxed for 4 h under $N_2$. The solution was evaporated to dryness and converted to methyl ester hydrochloride salts and purified in the standard manner. The compound from 1 (X=2-OCH$_3$) gave a mixture of erythro and threo isomers (ca. 1:1) which could not be separated.

Figure 36:
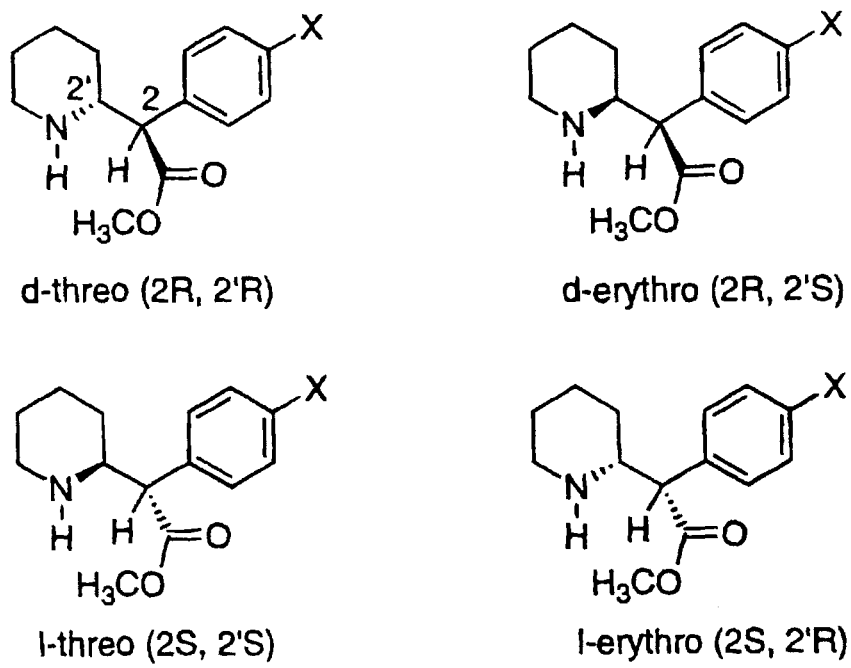
FIG. 36 depicts the That synthesis of enantiomerically pure methylphenidate.

That et al., *J. Med. Chem.*, 41:591-601 (1998) ("That") describes a method for the preparation of the optical isomers of 1 (FIG. 36) starting from chiral pipecolic acid in 27% yield and 99% enantiomeric purity for the d-threo enantiomer and in 30% yield and 96% enantiomeric purity for the 1-threo enantiomer. This synthetic methodology also provides the individual erythro enantiomers, and its versatility is demonstrated with the preparation of the threo enantiomers of p-bromo 2 and p-methoxy 3 derivatives all in 96-99% enantiomeric purity.

The That synthesis of the enantiomers of 1 relied upon pipecolic acid as the chiral educt. Optically pure pipecolic acid enantiomers were obtained by recrystallization of diastereomeric tartrate salts. Portoghese, et al., *J. Med. Chem.*, 11:12-15 (1968). The amino acid was separated from the tartaric acid by ion-exchange chromatography and subsequently amino-protected with a Boc group in 97% yield. Ponnusamy, et al., *Synthesis*, 48-49 (1986). To confirm the optical purity of the starting materials, the enantiomeric N-Boc pipecolic acids were derivatized to their 1-a-phenylethylamide using (benzotriazol-1-yloxy)tris(dimethylamino)-phosphonium hexafluorophosphate (BOP) as a coupling agent and analyzed by a GC-MS method capable of resolving the diastereomeric derivatives. Both optical isomers of N-Boc pipecolic acid were found to be >98% enantiomerically pure.

Figure 37:
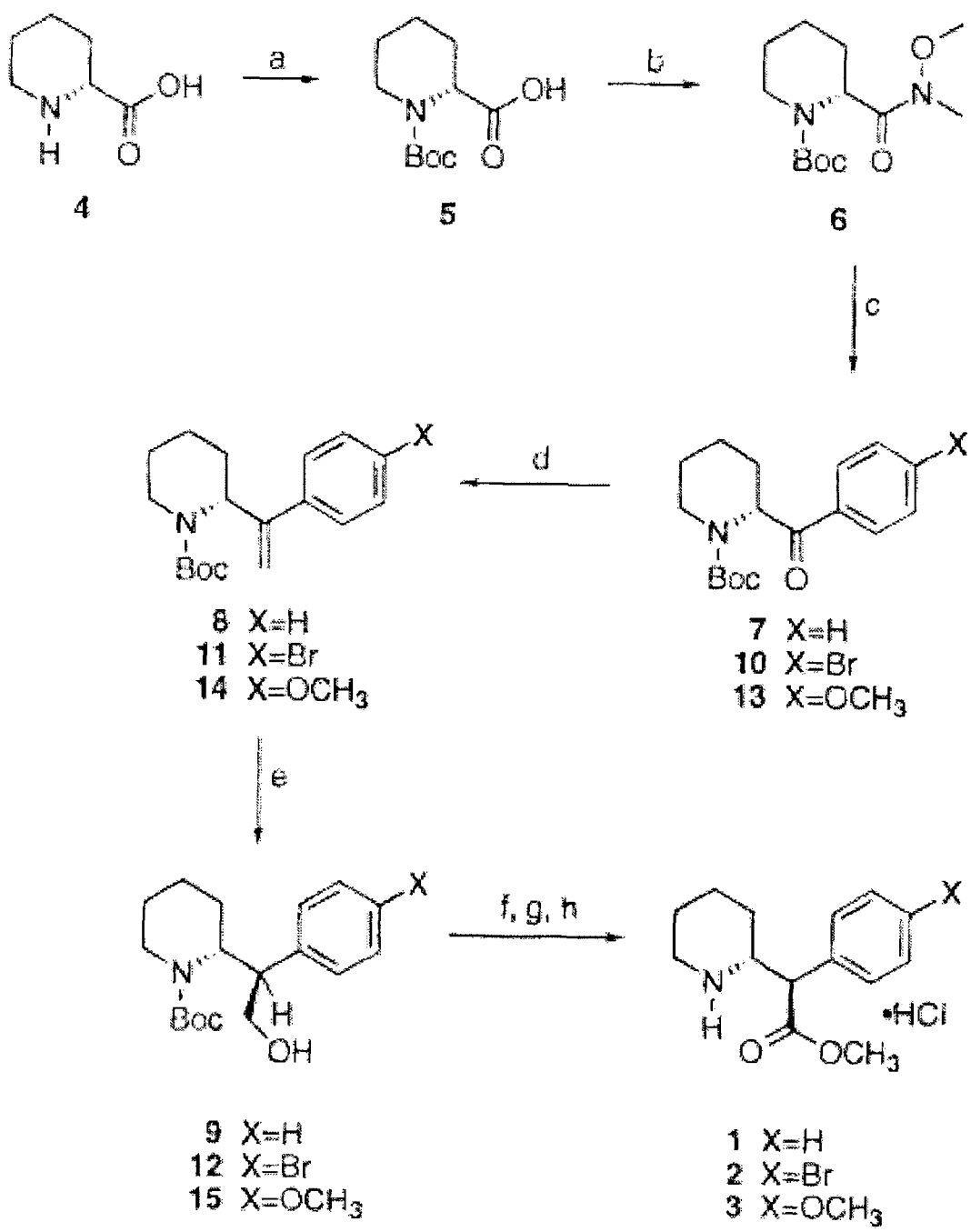
FIG. 37 depicts the synthesis of optically pure aromatic amino ketone.

The That synthesis of enantiomerically pure 1 (FIG. 36) depended upon the preparation of optically pure aromatic amino ketone 7 (FIG. 37). Prior literature on the preparation of optically pure amino ketones included two different strategies to aromatic products. Friedel-Crafts acylation of the corresponding N-protected amino acid chloride has been conducted on secondary and tertiary amines using benzene and anisole as electrophile acceptors. Nordlander, et al., *J. Org. Chem.* 1984, 49, 4107-4111; Nordlander, et al., *J. Org. Chem.* 1985, 50, 3481-3484; Buckley, et al., *J. Am. Chem. Soc.* 1981, 103, 6157-6163. However, this method lacks sufficient regiocontrol in the preparation of aromatic-substituted compounds and is not amenable to elaboration of nonphenyl aromatic systems. Organometallic addition to a suitably activated N-protected pipecolic derivative was an appealing approach which could provide better regiocontrol in the case of substituted aromatic derivatives and also allow the synthesis of a larger number of aromatic and heteroaromatic systems.

Though amino ketones of >99% enantiomeric purity have been obtained by organometallic methods, much of the work has concentrated on protected amino acid substrates containing abstractable carbamate protons. Buckley and Rapoport have shown that the presence of this abstractable proton is essential to maintaining configurational stability of the α-carbon by preventing deprotonation of the α-proton. Buckley, et al., *J. Am. Chem. Soc.* 1981, 103, 6157-6163. Nitrogen-protected pipecolic acid would not contain an abstractable carbamate proton which may then increase the likelihood of racemization under basic conditions. Cupps et al. have also evaluated several carboxylate-activating groups in the preparation of optically pure α,β-acetylenic ketones of alanine, methionine, and phenylalanine Cupps, et al., *J. Org. Chem.* 1985, 50, 3972-3979. Alternatively, Rapoport has developed extensive methodology using amino acids protected with the extremely bulky 9-(9-phenylfluorenyl) (Phfl) group. Lubell, et al., *J. Am. Chem. Soc.* 1987, 109, 236-239; Lubell, et al., *J. Am. Chem. Soc.* 1988, 110, 7447-7455; Lubell, et al., *J. Org. Chem.* 1990, 55, 3511-3522. The amino acids protected in this way can be transformed to their equivalent α-amino aldehydes, ketones, and esters with no detectable racemization. That's initial approach to preparing an optically pure aromatic amino ketone of pipecolic acid attempted to take advantage of the configurational stability of N-Phfl-protected amino acids. This route was found to be less fruitful because of the difficulties in synthesizing N-(Phfl)-D-pipecolate N,O-dimethylamide. Even after obtaining the desired aromatic ketone by a circuitous route, the Phfl ketone was nonreactive toward Wittig olefination. Because of these initial problems, That decided to switch to a Boc protecting group.

Figure 38:
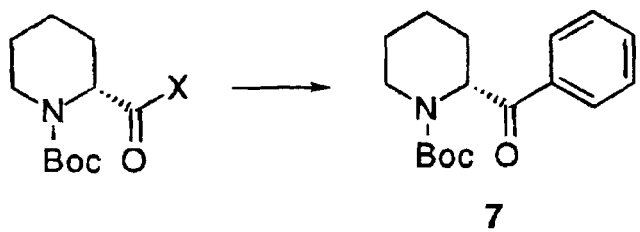
FIG. 38 shows the results of the reaction of metallobenzene with pipecolic acid derivatives.

Using the results of the experimental and literature investigation as a starting point to obtaining protected ketone 7 (FIG. 37) and its aromatic-substituted derivatives in enantiomerically pure form, derivatives of 5 such as its S-thiopyridyl ester (Corey, et al., *Tetrahedron Lett.* 1979, 2875-2878; Mukaiyama, et al., *J. Am. Chem. Soc.* 1973, 95, 4763-4765) diphenylphosphinoyl anhydride, (Ookawa, et al., *J. Chem. Soc. Perkin Trans.* 11987, 1465-1471) and N-methoxy-N-methylamide (Nahm, et al., *Tetrahedron Lett.* 1981, 22, 3815-3818) were treated with organometallic reagents under various reaction conditions. The results of the reaction of metallobenzene with pipecolic acid derivatives are summarized in FIG. 38.

When N-methoxy-N-methylamide 6 was treated with 110 mol % of phenyllithium in THF at −23° C., the isolated yield of 7 was 64%. Unfortunately, the product was found to be optically impure. The observed 10% racemization may have been the result of using a slight excess of the organolithium reagent. When the reaction was repeated in Et$_2$O at −23° C. with 100 mol % of organometallic reagent, the desired compound was obtained in enantiopure form and in 73% yield after recovery of starting material.

Once in hand, ketone 7 (FIG. 37) was converted to the chiral aromatic alkene 8 using a methylenetriphenylphosphonium ylide prepared from methyltriphenylphosphonium bromide and potassium tert-butoxide in THF at room temperature. With a slight excess (104 mol %) of Wittig reagent, the reaction did not go to completion, and the olefin was isolated in 50% yield. Increasing the amount of Wittig reagent to 150 mol % allowed clean transformation to a product which was easily purified by filtration though a short plug of silica gel in >90% yield.

The transformation of olefin 8 (FIG. 39) to the diastereomers of alcohol 9 was critical in generating the second stereocenter of the target compound. It was important to achieve stereocontrol in the hydroboration/oxidation of 8 in order to obtain the desired threo enantiomer. Examples of remarkable 1,2- and 1,3-asymmetric induction in the hydroboration of acyclic terminal olefins have appeared in the literature. Schmid, et al., *J. Am. Chem. Soc.* 1979, 101, 259-260; Evans, et al., *Tetrahedron Lett.* 1982, 23, 4577-4580. In these cases, the diastereofacial bias of the reaction was influenced significantly by the proximal asymmetric center of the substrate and not necessarily by the borane reagents used.

Figure 39:
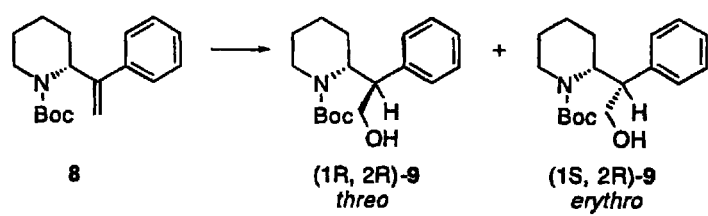
FIG. 39 shows the results of the borane reagent effect on the diastereoselectivity in the hydroboration/oxidation of N-Boc-phenylalkene.

That was interested in studying the 1,2-asymmetric inductive effects in the acyclic terminal olefinic system. Alkene 8 (FIG. 39) was treated with nonsubstituted, substituted, and chiral borane reagents. The results of the borane reagent effect on the diastereoselectivity in the hydroboration/oxidation of N-Boc-phenylalkene (8) are shown in FIG. 39.

Yields and diastereomer ratios were determined after isolation of the products by silica column chromatography. Though no simple model could explain the diastereomer ratios obtained, certain trends were still apparent. The combined yield of erythro and threo alcohols tended to decrease with increasing steric bulkiness of the borane reagents, suggesting that 8 is an extremely hindered alkene. This was apparent with dicyclohexylborane (Pelter, A. and Smith, K. In *Comprehensive Organic Chemistry*; Trost, B. M., Ed.; Pergamon Press: Oxford, 1979; Vol. 3.10, p 689) which provided only 18% yield of the isomeric alcohols and with diisopinocampheylborane (not shown) which gave no isolatable product. The threo alcohol was favored with non- and disubstituted boranes while the erythro alcohol was the major isomer in the presence of the monosubstituted thexylborane. With the boranes, (+)- and (−)-IPC.BH$_2$ (Brown, et al., *J. Org. Chem.* 1978, 43, 4395-4397; Brown, et al., *Synthesis* 1978, 146-147) the threo/erythro ratio was greatly influenced by the chirality of the hydroborating reagent. The ratio of the two diastereomers was 1:3 respectively in the presence of (−)-IPC.BH$_2$. On the other hand, only threo alcohol was isolated when the olefinic system was treated with (+)-IPC.BH$_2$. Hydroboration with BH3.THF gave the highest overall yield of threo isomer (64%) while BH$_3$.Me$_2$S gave the highest overall yield of erythro isomer (30%).

Each isomeric alcohol was subject to PDC-mediated oxidation in DMF followed by treatment with excess ethereal diazomethane. The resulting N-Boc-methyphenidate was deprotected with 3 N methanolic HCl to give 1 as a white solid after recrystallization from EtOH/Et$_2$O in 60-65% yield from alcohol 9. Assignment of threo and erythro stereochemistry was made by comparison of the products to standards by retention time on a GC and by $^1$H NMR. Furthermore, subsequent pharmacological evaluation of these synthesized compounds provided results consistent with available literature and revealed that the assigned threo isomer was more active than its erythro counterpart (not shown).

The above methodology was applied to the preparation of the enantiomers of threo p-bromo (2) and p-methoxy (3) derivatives of 1 (FIG. 37). Hydroxamate 6 was reacted with the appropriate para-substituted aryllithium under similar conditions as with the nonsubstituted organometallic reagent. Yields for the formation of the ketone varied between 28 and 56%. The p-bromo ketone 10 was isolated along with traces of nonsubstituted ketone 7 which may have been the result of lithium/halogen exchange on the aromatic moiety of 10 followed by protonation after aqueous quench. Conditions for preparation and isolation of subsequent enantiomeric para-substituted intermediates and products were similar to those of the parent compound. Enantiomeric purities of all the products were assessed by a GC-MS derivatization assay.

That reported the first asymmetric preparation of the four enantiomers of methylphenidate as well as the threo enantiomers of its p-bromo 2 and p-methoxy 3 derivatives. From d-pipecolic acid, the (2R,2'R)-enantiomers of 1, 2, and 3 along with the (2S,2'R)-enantiomer of 1 were synthesized in >99% optical purity and 10-27% overall yield. The (2S,2'S)-enantiomers of 1, 2, and 3 along with the (2R,2'S)-enantiomer of 1 were prepared from l-pipecolic acid in 96% optical purity and 8-30% overall yield. The synthetic methodology described above can be applied to the preparation of novel aromatic methylphenidate derivatives.

That also includes detailed experimental procedures for the synthesis of the methyphenidate derivatives. Some of these procedures are described below.

General Chemistry

THF was distilled over K/benzophenone, and triethylamine (TEA) was distilled over CaH$_2$. Diphenylphosphinic chloride was distilled under reduced pressure. Anhydrous Et$_2$O and CH$_2$Cl$_2$ were obtained from Aldrich. N,O-Dimethylhydroxylamine hydrochloride was purchased from TCI America. Pipecolic acid was obtained from Acros Organics as a racemic mixture and resolved into its d- and l-enantiomers by recrystallization of its diastereomeric tartrate salts. Portoghese et al., *J. Med. Chem.*, 1968, 11, 12-15. Anisoyl-lithium was prepared by the methods of Berree et al. (Berree et al., *J. Org. Chem.*, 1996, 61, 715-721) and used as a 0.43M ethereal solution, while (p-bromophenyl)-lithium was prepared by the methods of Trepka and Sonnenfeld used as a 0.37 M ethereal solution (Trepka et al., *J. Organomet. Chem.*, 1969, 16, 317-320). BOP was prepared by the methods of Castro (Dormoy et al., *Tetrahedron Lett.*, 1979, 35, 3321-3322). Thiopyridyl chloroformate was used as a 0.19 M solution in CH$_2$Cl$_2$ and prepared according the methods of Corey (Corey et al., *Tetrahedron Lett.* 1979, 2875-2878). All moisture-sensitive reactions were performed under a static Ar atmosphere (balloon) using dry solvents. Organic layers from aqueous extractions were dried over anhydrous MgSO$_4$ unless otherwise indicated and flash evaporated under reduced pressure. Thin layer chromatography was performed on Whatman 250µ F$_{254}$ silica gel plates and visualized by UV or by treatment with 0.2% ninhydrin in acetone followed by heating at 160° C. Liquid chromatography was performed on Whatman 230-400 mesh silica gel using air pressure. GC-MS was obtained on a Hewlett-Packard 5890 GC, 5970 mass selective detector (MSD) with a capillary direct interface, and 5940 HP-UX Chemstation. The MSD includes a Phasor HED (high-energy dynode). The column was an HP Ultra-2 (cross-linked 5% phenyl methyl silicone) fused silica capillary column, 12 m length, 0.20 mm i.d., film thickness 0.33 mm. Analytical conditions include the following: initial column oven temperature of 130° C. increased at a rate of 7° C./min to a final temperature of 290° C. The injector temperature was 290° C., the detector temperature 300° C., the helium (carrier gas) column flow (linear velocity) 38 cm/s, septum purge flow 1.8 mL/min, purge vent flow 61 mL/min. MSD was set on scan mode for masses between 25 and 800 m/e. The $^1$H and $^{13}$C NMR spectra were recorded in CDCl$_3$ or CD$_3$OD as noted at 300 and 75 Hz, respectively, and coupling constants were reported in hertz. Melting points were uncorrected. Elemental analyses were performed by Quantitative Technologies, Inc.

N-(tert-Butyloxycarbonyl)-D-pipecolic Acid (5)
(FIG. 37)

To a vigorously stirred solution of d-pipecolic acid (2.0 g, 15.5 mmol) and TEA (2.4 mL, 17.2 mmol) in methanol (22 mL) at 50° C. was added di-tert-butyl dicarbonate (7.12 mL, 31.0 mmol) via syringe. Stirring was continued at 50° C. for 5 min and at room temperature for 1 h. The reaction mixture was then concentrated to an oily residue and suspended between EtOAc (75 mL) and saturated NaHCO$_3$ (75 mL). The organic layer was extracted with saturated NaHCO$_3$ (2×25 mL) and H$_2$O (25 mL). Combined aqueous layers were brought to pH=2.0 with 3 M HCl and immediately extracted with EtOAc (50 mL, 2×25 mL). The combined organic layers were washed with dilute HCl, dried, filtered, and evaporated to give 3.45 g of (R)-5 as a white solid (97% yield): mp 123-124° C.; $[\alpha]^{20}_D$+59.5° (c 2.06, CH$_2$Cl$_2$); $^1$H NMR (CDCl$_3$) δ 11.34 (s, 1H), 4.83 (d, J=13.5, 1H), 3.94 (m, 1H), 2.93 (m, 1H), 2.21 (br s, 1H), 1.66 (br s, 3H), 1.44 (s, 9H), 1.28 (m, 2H); $^{13}$C NMR (CDCl$_3$) δ 177.8, 156.2, 80.36, 53.61, 42.11, 28.34, 26.63, 24.60, 20.74. Anal. (C$_{11}$H$_{19}$NO$_4$) C, H, N.

N-(tert-Butyloxycarbonyl)-L-pipecolic acid (5)
(FIG. 37)

98% yield: mp 123-124° C.; $[\alpha]^{20}_D$−58.7° (c 3.42, CH$_2$Cl$_2$); $^1$H NMR (CDCl$_3$) δ 11.42 (s, 1H), 1.65 (br s, 3H), 1.43 (s, 9H), 1.30 (m, 2H); $^{13}$C NMR (CDCl$_3$) δ 177.8, 156.1, 80.36, 53.57, 42.09, 28.31, 26.60, 24.74, 20.77. Anal. (C$_{11}$H$_{19}$NO$_4$) C, H, N.

N-(tert-Butyloxycarbonyl)-D-pipecolate N-(Methyl-methoxyl) amide (6) (FIG. 37)

(R)-Acid 5 (7.0 g, 30.6 mmol) was dissolved in CH$_2$Cl$_2$ (94 mL), and N,O-dimethylhydroxylamine hydrochloride (3.57 g, 36.6 mmol) and TEA (15.0 mL, 108 mL) were added. Solid BOP (14.8 g, 33.6 mmol) was then added and the reaction mixture stirred for 6 h. The reaction mixture was diluted with CH$_2$Cl$_2$ (450 mL) and transferred to a separatory funnel containing 1 M HCl (60 mL). The organic layer was washed consecutively with NaHCO$_3$ (3×60 mL), brine (2×60 mL), and H$_2$O (2×60 mL). Drying over MgSO$_4$, filtration, and evaporation provided an oil which was chromatographed on silica gel with 25% EtOAc in hexanes as eluant to give 7.74 g of (R)-6 as a colorless oil (93% yield): [α]$^{20}_D$−1.35° (c 2.89, CH$_2$Cl$_2$); $^1$H NMR (CDCl$_3$) δ 4.94 (d, J=9.0, 1H), 3.87 (m, 1H), 3.72 (s, 3H), 3.39 (m, 1H), 3.14 (s, 3H), 1.96 (d, J=5.2, 1H), 1.66 (m, 2H), 1.62 (m, 1H), 1.44 (s, 9H), 1.24 (m, 2H); $^{13}$C NMR (CDCl$_3$) δ 173.2, 155.9, 79.40, 61.06, 50.47, 42.09, 31.89, 28.24, 26.27, 24.74, 19.44. Anal. (C$_{13}$H$_{24}$N$_2$O$_4$) C, H, N.

N-(tert-Butyloxycarbonyl)-L-pipecolate N-(methyl-methoxyl) amide (6) (FIG. 37)

94% yield: [α]$^{20}_D$+1.88° (c 4.30, CH$_2$Cl$_2$); $^1$H NMR (CDCl$_3$) δ 5.05 (br s, 1H), 3.91 (m, 1H), 3.76 (s, 3H), 3.44 (m, 1H), 3.18 (s, 3H), 1.98 (d, J=3.4, 1H), 1.67 (m, 2H), 1.57 (m, 1H), 1.44 (s, 9H), 1.24 (m, 2H); $^{13}$C NMR (CDCl$_3$) δ 172.8, 155.5, 78.84, 60.61, 50.10, 41.71, 31.47, 27.81, 25.86, 24.32, 19.03. Anal. (C$_{13}$H$_{24}$N$_2$O$_4$) C, H, N: calcd, 57.33. found, 58.62.

(2R)—N-(tert-Butyloxycarbonyl)piperidin-2-yl Phenyl Ketone (7) (FIG. 37)

A solution of (R)-hydroxamate 6 (400 mg, 1.47 mmol) in Et$_2$O (6.3 mL) was brought to −23° C. under an inert atmosphere, and 2.0 M phenyllithium in hexanes (735 μL, 1.47 mmol) was added dropwise via syringe over 15 min. Stirring was continued at −23° C. for 3 h, after which the reaction mixture was poured into an ice-chilled 1 M KH$_2$PO$_4$ solution (20 mL). The aqueous layer was extracted with EtOAc (4×15 mL), and the combined EtOAc layer was dried, filtered, and evaporated. Chromatography over silica gel eluting with 7.5-20% EtOAc in hexanes gave 200 mg of ketone (R)-7 as a white solid along with 143 mg of recovered starting material (47% yield, 73% yield based on recovered starting material): mp 126-128° C.; [α]$^{20}_D$+25.8° (c 1.06, CH$_2$Cl$_2$); $^1$H NMR (CDCl$_3$) δ 7.87 (m, 2H), 7.50 (m, 1H), 7.41 (m, 2H), 5.55 (d, J=11.7, 1H), 3.89 (m, 1H), 3.12 (m, 1H), 2.06 (m, 1H), 1.78 (m, 1H), 1.56 (m, 2H), 1.43 (s, 9H), 1.36 (br s, 2H); $^{13}$C NMR (CDCl$_3$) δ 200.9, 155.8, 135.8, 132.8, 128.5, 128.1, 79.94, 56.09, 42.57, 28.29, 26.18, 24.95, 19.92. Anal. (C$_{17}$H$_{23}$NO$_3$) C, H, N.

(2S)—N-(tert-Butyloxycarbonyl)piperidin-2-ylphenyl ketone (7) (FIG. 37)

47% yield as a white solid, 88% based on recovered starting material: mp 123-125° C.; [α]$^{20}_D$−24.6° (c 2.03, CH$_2$Cl$_2$); $^1$H NMR (CDCl$_3$) δ 7.87 (m, 2H), 7.49 (m, 1H), 7.41 (m, 2H), 5.55 (d, J=11.6, 1H), 3.91 (m, 1H), 3.13 (m, 1H), 2.06 (m, 1H), 1.78 (m, 1H), 1.57 (m, 2H), 1.42 (s, 9H), 1.36 (br s, 2H); $^{13}$C NMR (CDCl$_3$) δ 200.9, 155.7, 135.8, 132.8, 128.5, 128.1, 79.88, 56.01, 42.53, 28.24, 26.14, 24.91, 19.85. Anal. (C$_{17}$H$_{23}$NO$_3$) C, H, N.

(2R)—N-(tert-Butyloxycarbonyl)piperidin-2-yl 4-bromophenyl ketone (10) (FIG. 37)

33% yield as a white solid: mp 124-125° C.; [α]$^{20}_D$+29.8° (c 1.31, CH$_2$Cl$_2$); $^1$H NMR (CDCl$_3$) δ 7.78 (m, 2H), 7.56 (m, 2H), 5.48 (d, J=11.9, 1H), 3.90 (m, 1H), 3.03 (m, 1H), 2.07 (m, 1H), 1.78 (m, 1H), 1.59 (m, 2H), 1.44 (br s, 11H); $^{13}$C NMR (CDCl$_3$) δ 200.0, 155.7, 134.6, 131.9, 129.8, 127.9, 80.23 56.10, 42.72, 28.34, 25.94, 24.98, 19.94. Anal. (C$_{17}$H$_{22}$NO$_3$Br) C, H, N.

(2S)—N-(tert-Butyloxycarbonyl)piperidin-2-yl 4-bromophenyl ketone (10) (FIG. 37)

28% yield as a white solid: mp 124-126° C.; [α]$^{20}_D$−26.3° (c 1.01, CH$_2$Cl$_2$); $^1$H NMR (CDCl$_3$) δ 7.79 (m, 2H), 7.58 (m, 2H), 5.49 (d, J=11.9, 1H), 3.91 (m, 1H), 3.04 (m, 1H), 2.08 (m, 1H), 1.80 (m, 1H), 1.61 (m, 2H), 1.45 (br s, 11H); $^{13}$C NMR (CDCl$_3$) δ 200.1, 155.7, 134.6, 131.9, 129.8, 128.0, 80.28, 56.25, 42.77, 28.40, 26.05, 25.07, 19.99.

(2R)—N-(tert-Butyloxycarbonyl)piperidin-2-yl-4-methoxyphenyl ketone (13) (FIG. 37)

46% yield as a white solid: mp 98-99° C.; [α]$^{20}_D$+17.3° (c 1.24, CH$_2$Cl$_2$); $^1$H NMR (CDCl$_3$) δ 7.90 (m, 2H), 6.91 (m, 2H), 5.52 (d, J=11.9, 1H), 3.87 (m, 1H), 3.84 (s, 3H), 3.16 (m, 1H), 2.08 (m, 1H), 1.79 (m, 1H), 1.56 (m, 2H), 1.44 (br s, 11H); $^{13}$C NMR (CDCl$_3$) δ 199.2, 163.3, 155.8, 130.5, 128.6, 113.7, 79.90, 56.67, 55.45, 42.61, 28.35, 26.52, 25.03, 19.90. Anal. (C$_{18}$H$_{25}$NO$_4$) C, H, N.

(2S)—N-(tert-Butyloxycarbonyl)piperidin-2-yl-4-methoxyphenyl ketone (13) (FIG. 37)

56% yield as a white solid: mp 97-99° C.; [α]$^{20}_D$−17.9° (c 1.33, CH$_2$Cl$_2$); $^1$H NMR (CDCl$_3$) δ 7.90 (m, 2H), 6.90 (m, 2H), 5.52 (d, J=12.0, 1H), 3.87 (m, 1H), 3.84 (s, 3H), 3.16 (m, 1H), 2.08 (m, 1H), 1.79 (m, 1H), 1.56 (m, 2H), 1.44 (br s, 11H); $^{13}$C NMR (CDCl$_3$) δ 199.2, 163.3, 155.8, 130.6, 128.5, 113.7, 79.91, 56.67, 55.45, 42.58, 28.36, 26.50, 25.11, 19.96. Anal. (C$_{18}$H$_{25}$NO$_4$) C, H, N: calcd, 67.69. found, 67.10.

1-[(2R)—N-(tert-Butyloxycarbonyl)piperidin-2-yl]-1-phenylethene (8) (FIG. 37)

To a suspension of methyltriphenylphosphonium bromide (230 mg, 0.644 mmol) in THF (1.0 mL) was added solid potassium tert-butoxide (72.2 mg, 0.644 mmol), and the resulting yellow suspension was allowed to stir for 10 min. A solution of (R)-7 (124 mg, 0.429 mmol) in THF (2.0 mL) was then added dropwise via syringe and the reaction allowed to proceed for 5 min. The reaction was quenched with H$_2$O (1.0 mL) and suspended between EtOAc (15 mL) and H$_2$O (15 mL). The aqueous layer was extracted with EtOAc (2×15 mL). The combined EtOAc layers were dried, filtered, and evaporated to an oil which was then filtered though a plug of silica gel eluting with 9% EtOAc in hexanes to give 115 mg (93%) of (R)-8 as a colorless oil: [α]$^{20}_D$−28.3° (c 1.16, CH$_2$Cl$_2$); $^1$H NMR (CDCl$_3$) δ 7.30 (m, 3H), 7.27 (m, 2H), 5.26 (br s, 2H), 5.04 (s, 1H), 3.95 (m, 1H), 2.89 (t, J=10, 1H), 1.78 (d, J=2.9, 1H), 1.62 (m, 2H), 1.45 (s, 9H), 1.26 (br s, 3H); $^{13}$C NMR (CDCl$_3$) δ 155.4, 148.2, 141.4, 128.2, 127.3, 127.0, 124.4, 114.1, 79.42, 40.27, 28.44, 26.81, 25.46, 19.18. Anal. ($C_{18}H_{25}NO_2$) C, H, N.

1-(2S)—N-(tert-butyloxycarbonyl)piperidin-2-yl]-1-phenylethene (8) (FIG. 37)

90% yield as a colorless oil: $[\alpha]^{20}_D$+26.6° (c 1.59, $CH_2Cl_2$); $^1$H NMR ($CDCl_3$) δ 7.30 (m, 3H), 7.27 (m, 2H), 5.26 (br s, 2H), 5.03 (s, 1H), 3.96 (m, 1H), 2.89 (t, J=8.9, 1H), 1.78 (d, J=3.2, 1H), 1.63 (m, 2H), 1.45 (s, 9H), 1.39 (br s, 3H); $^{13}$C NMR ($CDCl_3$) δ 155.3, 148.1, 141.3, 128.1, 127.2, 126.9, 124.2, 114.0, 79.32, 40.17, 28.33, 26.69, 25.33, 19.05. Anal. ($C_{18}H_{25}NO_2$) C, H, N.

1-[(2R)—N-(tert-Butyloxycarbonyl)piperidin-2-yl]-1-(4-bromophenyl)ethene (11) (FIG. 37)

95% yield as a colorless oil: $[\alpha]^{20}_D$-9.21° (c 3.28, $CH_2Cl_2$); $^1$H NMR ($CDCl_3$) δ 7.43 (m, 2H), 7.20 (m, 2H), 5.27 (br s, 2H), 5.07 (s, 1H), 3.86 (d, J=3.0, 1H), 2.82 (m, 1H), 1.83 (m, 1H), 1.63 (m, 2H), 1.45 (s, 9H), 1.41 (br s, 3H); $^{13}$C NMR ($CDCl_3$) δ 155.3, 147.3, 140.2, 132.0, 131.3, 128.7, 121.3, 114.8, 79.61, 40.34, 28.46, 26.72, 25.40, 19.15. Anal. ($C_{18}H_{24}NO_2Br$) C, H, N.

1-[(2S)—N-(tert-Butyloxycarbonyl)piperidin-2-yl]-1-(4-bromophenyl)ethene (11) (FIG. 37)

93% yield as a colorless oil: $[\alpha]^{20}_D$+7.55° (c 2.86, $CH_2Cl_2$); $^1$H NMR ($CDCl_3$) δ 7.43 (m, 2H), 7.20 (m, 2H), 5.27 (br s, 2H), 5.07 (s, 1H), 3.86 (d, J=3.0, 1H), 2.82 (m, 1H), 1.84 (m, 1H), 1.63 (m, 2H), 1.46 (s, 9H), 1.36 (br s, 3H); $^{13}$C NMR ($CDCl_3$) δ 155.3, 147.2, 140.2, 132.0, 131.3, 128.7, 121.3, 114.8, 79.61, 40.34, 28.47, 26.69, 25.43, 19.15. Anal. ($C_{18}H_{24}NO_2Br$) C, H, N; Calcd, 59.02. found, 59.54.

1-[(2R)—N-(tert-Butyloxycarbonyl)piperidin-2-yl]-1-(4-methoxyphenyl)ethene (14) (FIG. 37)

98% yield as a colorless oil: $[\alpha]^{20}_D$-22.7° (c 2.87, $CH_2Cl_2$); $^1$H NMR ($CDCl_3$) δ 7.28 (m, 2H), 6.87 (m, 2H), 5.25 (br s, 2H), 5.01 (s, 1H), 3.94 (m, 1H), 3.82 (s, 3H), 2.90 (m, 1H), 1.83 (m, 1H), 1.63 (m, 2H), 1.49 (br s, 12H); $^{13}$C NMR ($CDCl_3$) δ 158.9, 155.4, 147.5, 133.7, 128.0, 113.5, 113.1, 79.32, 55.19, 53.51, 40.24, 28.40, 26.75, 25.43, 19.12. Anal. ($C_{19}H_{27}NO_3$) C, H, N.

1-(2S)—N-(tert-Butyloxycarbonyl)piperidin-2-yl]-1-(4-methoxyphenyl)ethene (14) (FIG. 37)

96% yield as a colorless oil: $[\alpha]^{20}_D$+25.6° (c 1.07, $CH_2Cl_2$); $^1$H NMR ($CDCl_3$) δ 7.28 (m, 2H), 6.87 (m, 2H), 5.24 (br s, 2H), 5.05 (s, 1H), 3.95 (m, 1H), 3.81 (s, 3H), 2.92 (m, 1H), 1.83 (m, 1H), 1.60 (m, 2H), 1.48 (br s, 12H); $^{13}$C NMR ($CDCl_3$) δ 158.9, 155.4, 147.5, 133.7, 128.0, 113.5, 113.0, 79.32, 55.19, 53.60, 40.27, 28.40, 26.75, 25.43, 19.12. Anal. ($C_{19}H_{27}NO_3$) C, H, N.

(1R)-1-[(2R)—N-(tert-Butyloxycarbonyl)piperidin-2-yl]-1-phenyl-2-hydroxyethane and (1S)-1-[(2R)—N-(tert-Butyloxycarbonyl)piperidin-2-yl]-1-phenyl-2-hydroxyethane (9) (FIG. 37)

To a solution of (R)-8 (115 mg, 0.401 mmol) in THF (2.0 mL) was added 1.0 $MBH_3$·THF (802 µL, 0.802 mmol) dropwise at room temperature via syringe over about 5 min. The reaction mixture was then stirred for 4 h after which $H_2O$ (1.0 mL), 3 N NaOH (1.0 mL), and 30% $H_2O_2$ (2.0 mL) were added consecutively. Stirring was continued overnight. The resulting mixture was suspended between EtOAc (20 mL) and $H_2O$ (15 mL), and the aqueous layer was extracted with EtOAc (3×10 mL). The combined EtOAc layers were dried, filtered, and evaporated to an oil which was purified by silica gel chromatography eluting with 16-20% EtOAc in hexanes. The less polar (1R,2R)-9 was obtained as a white solid (78 mg, 64% yield): mp 80-81° C.; $[\alpha]^{20}_D$+12.4° (c 2.20, $CH_2Cl_2$); $^1$H NMR ($CDCl_3$) δ 7.29 (m, 5H), 4.60 (d, J=12, 1H), 4.00 (d, J=13, 1H), 3.70 (m, 2H), 3.52 (m, 2H), 3.03 (d, J=12, 2H), 2.81 (t, J=11, 1H), 1.60 (m, 2H), 1.46 (s, 9H), 1.39 (br s, 2H); $^{13}$C NMR ($CDCl_3$) δ 156.5, 141.3, 128.9, 128.6, 126.8, 80.39, 63.54, 50.33, 45.88, 39.92, 28.49, 26.09, 25.43, 18.88. The more polar (1S,2R)-9 (30 mg, 25% yield) was obtained as a colorless oil: $[\alpha]^{20}_D$+52.3° (c 1.06, $CH_2Cl_2$); $^1$H NMR ($CDCl_3$) δ 7.32 (m, 5H), 4.57 (m, 1H), 3.87 (m, 3H), 3.27 (m, 1H), 2.61 (m, 1H), 1.83 (m, 1H), 1.70 (m, 3H), 1.36 (s, 9H), 1.34 (br s, 2H).

(1S)-1-[(2S)—N-(tert-Butyloxycarbonyl)piperidin-2-yl]-1-phenyl-2-hydroxyethane and (1R)-1-[(2S)—N-(tert-Butyloxycarbonyl)piperidin-2-yl]-1-phenyl-2-hydroxyethane (9) (FIG. 37)

61% yield of (1S,2S)-9 as a white solid: mp 78-80° C.; $[\alpha]^{20}_D$-11.1° (c 1.32, $CH_2Cl_2$); $^1$H NMR ($CDCl_3$) δ 7.27 (m, 5H), 4.61 (d, J=11, 1H), 4.01 (d, J=12, 1H), 3.71 (m, 2H), 3.54 (m, 2H), 3.04 (d, J=11, 2H), 2.82 (t, J=12, 1H), 1.61 (m, 2H), 1.48 (s, 9H), 1.28 (br s, 2H); $^{13}$C NMR ($CDCl_3$) δ 156.2, 141.2, 128.6, 128.3, 126.5, 80.10, 50.17, 45.67, 39.70, 28.28, 25.88, 25.23, 18.67. Anal. ($C_{18}H_{27}NO_3$) C, H, N.

(1S,2R)-9 (FIG. 37) was obtained as an oil in 21% yield: $[\alpha]^{20}_D$-52.7° (c 1.09, $CH_2Cl_2$); $^1$H NMR ($CDCl_3$) δ 7.37 (m, 5H), 4.58 (m, 1H), 3.88 (m, 3H), 3.31 (m, 1H), 2.67 (m, 1H), 1.85 (m, 1H), 1.73 (m, 3H), 1.35 (s, 9H), 1.32 (br s, 2H). Anal. ($C_{18}H_{27}NO_3$) C, H, N.

(1R)-1-[(2R)—N-(tert-Butyloxycarbonyl)piperidin-2-yl]-1-(4-bromophenyl)-2-hydroxyethane (12) (FIG. 37)

58% yield as a white solid: mp 117-118° C.; $[\alpha]^{20}_D$+7.28° (c 3.09, $CH_2Cl_2$); $^1$H NMR ($CDCl_3$) δ 7.43 (m, 2H), 7.27 (m, 2H), 4.59 (d, J=12, 1H), 4.04 (d, J=13, 1H), 3.73 (m, 2H), 3.51 (t, J=12, 1H), 3.09 (d, J=12, 1H), 2.85 (t, J=13, 1H), 1.64 (br 1H), 1.50 (s, 9H), 1.47 (br s, 2H), 1.28 (m, 2H); $^{13}$C NMR ($CDCl_3$) δ 156.6, 140.5, 131.6, 130.6, 120.6, 80.66, 63.18, 50.10, 45.25, 39.98, 28.51, 26.08, 25.38, 18.87. Anal. ($C_{18}H_{26}NO_3Br$) C, H, N.

(1S)-1-[(2S)—N-(tert-Butyloxycarbonyl)piperidin-2-yl]-1-(4-bromophenyl)-2-hydroxyethane (12) (FIG. 37)

56% yield as a white solid: mp 114-117° C.; $[\alpha]^{20}_D$-7.18° (c 3.51, $CH_2Cl_2$); $^1$H NMR ($CDCl_3$) δ 7.44 (m, 2H), 7.27 (m, 2H), 4.59 (d, J=12, 1H), 4.04 (d, J=13, 1H), 3.71 (m, 2H), 3.51 (t, J=12, 1H), 3.02 (d, J=12, 1H), 2.82 (t, J=13, 1H), 1.59 (br s, 1H), 1.50 (s, 9H), 1.47 (br s, 2H), 1.26 (m, 2H); $^{13}$C NMR ($CDCl_3$) δ 156.6, 140.5, 131.6, 130.6, 120.6, 80.66, 63.17, 50.08, 45.23, 39.99, 28.50, 26.11, 25.40, 18.85. Anal. ($C_{18}H_{26}NO_3Br$) C, H, N.

(1R)-1-[(2R)—N-(tert-Butyloxycarbonyl)piperidin-2-yl]-1-(4-methoxyphenyl)-2-hydroxyethane (15) (FIG. 37)

62% yield as a white solid: mp 115-117° C.; $[\alpha]^{20}_D$+4.12° (c 1.31, CH$_2$Cl$_2$); $^1$H NMR (CDCl$_3$) δ 7.37 (m, 2H), 6.94 (m, 2H), 4.67 (d, J=11, 1H), 4.12 (d, J=13, 1H), 3.87 (s, 3H), 3.80 (m, 2H), 3.60 (br s, 2H), 3.12 (d, J=10, 1H), 2.93 (t, J=11, 1H), 1.71 (m, 1H), 1.58 (s, 9H), 1.49 (m, 3H); $^{13}$C NMR (CDCl$_3$) δ 158.3, 156.3, 133.3, 129.6, 113.9, 80.23, 63.57, 55.12, 50.41, 44.86, 39.82, 28.40, 25.95, 25.36, 18.79. Anal. (C$_{19}$H$_{29}$NO$_4$) C, H, N.

(1S)-1-[(2S)—N-(tert-Butyloxycarbonyl)piperidin-2-yl]-1-(4-methoxyphenyl)-2-hydroxyethane (15) (FIG. 37)

64% yield as a white solid: mp 116-117° C.; $[\alpha]^{20}_D$–4.18° (c 1.22, CH$_2$Cl$_2$); $^1$H NMR (CDCl$_3$) δ 7.37 (m, 2H), 6.94 (m, 2H), 4.66 (d, J=10, 1H), 4.11 (d, J=12, 1H), 3.86 (s, 3H), 3.80 (m, 2H), 3.60 (br s, 2H), 3.12 (d, J=11, 1H), 2.92 (t, J=11, 1H), 1.70 (m, 1H), 1.58 (s, 9H), 1.44 (m, 3H); $^{13}$C NMR (CDCl$_3$) δ 158.3, 156.3, 133.3, 129.6, 113.9, 80.23, 63.57, 55.13, 50.42, 44.86, 39.82, 28.41, 25.95, 25.37, 18.79. Anal. (C$_{19}$H$_{29}$NO$_4$) C, H, N.

(2R,2'R)-Methylphenidate Hydrochloride (1) (FIG. 37)

(1R,2R)-Alcohol 9 (228 mg, 0.748 mmol) was dissolved in DMF (3.0 mL), and PDC (984 mg, 2.62) was added. After 17 h of stirring, the reaction was quenched with H$_2$O (40 mL) and the resulting mixture extracted with Et$_2$O (6×20 mL). Combined Et$_2$O layers were then extracted with 0.5 N NaOH (4×30 mL) and the alkaline solution brought to pH=2.0 with 3 N HCl. A white precipitate formed and was extracted into EtOAc (4×30 mL) which was dried, filtered, and evaporated under reduced pressure to give a crude colorless oil (194 mg).

A portion (180 mg) of the crude oil was treated with excess diazomethane in ether (10 mL). The solution was evaporated to a light yellow oil which was stirred in 3 N methanolic HCl (10 mL) at room temperature overnight. Evaporation under reduced pressure provided a crude off-white solid which was recrystallized from EtOH/Et$_2$O to give 124 mg of (2R,2'R)-1 as a white solid (67% yield from (1R,2R)-9): mp 221-223° C.; $[\alpha]^{20}_D$+82.6° (c 1.09, MeOH); $^1$H NMR (CD$_3$OD) δ 7.38 (m, 2H), 7.30 (m, 3H), 3.89 (m, 2H), 3.73 (s, 3H), 3.47 (d, J=12.6, 1H), 3.31 (s, 1H), 3.11 (t, J=11.2, 1H), 1.78 (m, 3H), 1.48 (m, 3H); $^{13}$C NMR (CD$_3$OD) δ 173.4, 135.4, 130.5, 129.8, 59.35, 55.39, 53.52, 46.79, 27.73, 23.43, 22.95; HRMS calcd for C$_{14}$H$_{19}$NO$_2$ (MH$^+$) 234.1495. found, 234.1509.

(2S,2'R)-Methylphenidate Hydrochloride (1) (FIG. 37)

73% yield as a white solid from (1S,2R)-9.): mp 218-219° C.; $[\alpha]^{20}_D$–94.5° (c 1.59, MeOH); $^1$H NMR (CD$_3$OD) δ 7.44 (m, 5H), 4.03 (d, J=9.1, 1H), 3.78 (t, J=8.2, 1H), 3.70 (s, 3H), 3.32 (m, 1H), 3.00 (t, J=13, 1H), 2.10 (m, 1H), 1.91 (m, 2H), 1.71 (m, 3H); $^{13}$C NMR (CD$_3$OD) δ 172.6, 134.0, 130.8, 130.3, 130.0, 59.52, 55.92, 53.14, 47.01, 28.78, 23.31, 23.01; HRMS calcd for C$_{14}$H$_{19}$NO$_2$ (MH$^+$) 234.1495. found, 234.1495.

(2S,2'S)-Methylphenidate hydrochloride (1) (FIG. 37)

67% yield as a white solid from (1S,2S)-9: mp 219-221° C.; $[\alpha]^{20}_D$–81.8° (c 1.38, MeOH); $^1$H NMR (CD$_3$OD) δ 7.41 (m, 2H), 7.31 (m, 3H), 3.88 (m, 2H), 3.73 (s, 3H), 3.45 (d, J=11, 1H), 3.11 (t, J=13, 1H), 1.82 (m, 3H), 1.51 (m, 3H); $^{13}$C NMR (CD$_3$OD) δ 173.2, 135.3, 130.4, 129.6, 59.20, 55.21, 53.40, 46.64, 27.55, 23.24, 22.80; HRMS calcd for C$_{14}$H$_{19}$NO$_2$ (WO 234.1495. found, 234.1496. Anal. (C$_{14}$H$_{19}$NO$_2$.HCl.0.14H$_2$O) C, H, N.

(2R,2'S)-Methylphenidate hydrochloride (1) (FIG. 37)

68% yield as a white solid from (1R,2S)-9: mp 216-219° C.; $[\alpha]^{20}_D$+92.3° (c 1.11, MeOH); $^1$H NMR (CD$_3$OD) δ 7.45 (m, 5H), 3.97 (d, J=9.3, 1H), 3.81 (t, J=9.8, 1H), 3.73 (s, 3H), 3.35 (m, 1H), 3.01 (t, J=13, 1H), 2.13 (m, 1H), 1.95 (m, 2H), 1.72 (m, 3H); $^{13}$C NMR (CD$_3$OD) δ 172.5, 134.1, 130.7, 130.2, 130.0, 59.52, 55.86, 53.14, 46.99, 28.65, 23.22, 22.99; HRMS calcd for C$_{14}$H$_{19}$NO$_2$ (WO 234.1495. found, 234.1493. Anal. (C$_{14}$H$_{19}$NO$_2$.HCl.0.16H$_2$O) C, H, N.

(2R,2'R)-p-(Bromomethyl)phenidate hydrochloride (2) (FIG. 37)

62% yield as a white solid from (2R,2'R)-12. mp 222-223° C.; $[\alpha]^{20}_D$+69.1° (c 3.09, CH$_2$Cl$_2$); $^1$H NMR (CD$_3$OD) δ 7.56 (d, J=8.4, 2H), 7.26 (d, J=8.4, 2H), 3.99 (d, J=9.8, 1H), 3.84 (t, J=9.9, 1H), 3.73 (s, 3H), 3.46 (d, J=13, 1H), 3.11 (t, J=13, 1H), 1.79 (m, 3H), 1.49 (m, 3H); $^{13}$C NMR (CD$_3$OD) δ 172.8, 134.4, 133.5, 131.6, 123.6, 58.93, 54.60, 53.56, 46.67, 27.59, 23.25, 22.76; HRMS calcd for C$_{14}$H$_{18}$NO$_2$Br (MH$^+$) 312.0599. found, 312.0614.

(2S,2'S)-p-(Bromomethyl)phenidate hydrochloride (2) (FIG. 37)

58% yield as a white solid from (2S,2'S)-12: mp 213-216° C.; $[\alpha]^{20}_D$–64.6° (c 1.90, CH$_2$Cl$_2$); $^1$H NMR (CD$_3$OD) δ 7.57 (d, J=8.4, 2H), 7.25 (d, J=8.4, 2H), 3.94 (d, J=9.8, 1H), 3.83 (t, J=11, 1H), 3.74 (s, 3H), 3.45 (d, J=13, 1H), 3.10 (t, J=13, 1H), 1.78 (m, 3H), 1.48 (m, 3H); $^{13}$C NMR (CD$_3$OD) δ 172.8, 134.4, 133.5, 131.6, 123.7, 58.96, 54.63, 53.56, 46.70, 27.68, 23.29, 22.76; HRMS calcd for C$_{14}$H$_{18}$NO$_2$Br (MH$^+$) 312.0599. found, 312.0577.

(2R,2'R)-p-(Methoxymethyl)phenidate hydrochloride (3) (FIG. 37)

64% yield as a white solid from (2R,2'R)-15: mp 226-228° C.; $[\alpha]^{20}_D$+86.6° (c 1.98, MeOH); $^1$H NMR (CD$_3$OD) δ 7.22 (d, J=8.6, 2H), 6.95 (d, J=8.6, 2H), 3.86 (d, J=10, 1H), 3.79 (s, 3H), 3.77 (m, 1H), 3.72 (s, 3H), 3.44 (d, J=11, 1H), 3.10 (t, J=13, 1H), 1.80 (m, 3H), 1.48 (m, 3H); $^{13}$C NMR (CD$_3$OD) δ 173.5, 161.4, 130.7, 126.9, 115.7, 59.35, 55.83, 54.51, 53.34, 46.64, 27.65, 23.38, 22.83; HRMS calcd for C$_{15}$H$_{21}$NO$_3$ (MH$^+$) 264.1600. found, 264.1625. Anal. (C$_{15}$H$_{21}$NO$_3$.HCl) C, H, N: calcd. 60.09. found 59.52.

(2S,2'S)-p-(Methoxymethyl)phenidate hydrochloride (3) (FIG. 37)

60% yield as a white solid from (2S,2'S)-15: mp 226-228° C.; $[\alpha]^{20}_D$–87.7° (c 1.38, MeOH); $^1$H NMR (CD$_3$OD) δ 7.23 (d, J=8.6, 2H), 6.93 (d, J=8.6, 2H), 3.96 (d, J=10, 1H), 3.77 (br s, 4H), 3.71 (s, 3H), 3.47 (d, J=12, 1H), 3.11 (t, J=12, 1H), 1.82 (m, 3H), 1.45 (m, 3H); $^{13}$C NMR (CD$_3$OD) δ 173.5, 161.2, 130.7, 127.0, 115.7, 59.28, 55.86, 54.37, 53.36, 46.61, 27.46, 23.22, 22.83; HRMS calcd for $C_{15}H_{21}NO_3$ (MH$^+$) 264.1600. found, 264.1621.

Assessment of Enantiomeric Purity of N-Boc-pipecolic Acid (5) (FIG. 37)

Acid 5 (10 mg, 44 µmol) was dissolved in CH$_2$Cl$_2$ (200 µL) containing TEA (18.4 µL, 131 µmol). 1-(-)-α-phenyl-ethylamine (6.8 mL, 53 µmol) of >98% optical purity and BOP (23.2 mg, 52 µmol) were added, and the reaction was stirred in a sealed vial for 60 min. The reaction mixture was washed sequentially with 1.0 M HCl (500 µL) and saturated NaHCO$_3$ (500 µL). The organic layer (10 µL) was diluted in amyl acetate (10 mL), and a 1.0 µL aliquot was analyzed by capillary GC-MS under the conditions described above which allowed baseline separation of the enantiomers of 5. By this method, both enantiomers of 5 were found to be >98% enantiomerically pure.

Optical Purity of Chiral MPH and its Para-Substituted Analogues

The enantiomeric dispositions of each of the threo enantiomers of 1, 2, and 3 prepared in the laboratory were assessed by gas chromatographic derivatization technique. Each hydrochloride salt of the d- and l-threo enantiomers (2 µg) was dissolved in 2.0 mL of 10% aqueous Na$_2$CO$_3$ and chilled on ice for 10 min. A 0.1 M solution of (S)-methoxy-(trifluoromethyl)phenylacetyl chloride (Dale, et al., *J. Org. Chem.* 1969, 34, 2543-2549) in CH$_2$Cl$_2$ (25 µL) was added and the solution vortexed for 1 min. The reaction was allowed to proceed at room temperature for 1 h. Cyclohexane (4.0 mL) was added, and the tubes were shaken for 10 min. After a brief centrifugation to separate the layers, the top cyclohexane layer was transferred into a clean tube, dried in a Savant speed vac concentrator, and reconstituted in amyl acetate (100 µL). The samples were transferred to crimp-top vials with 100 µL volume silanized inserts and injected into a gas chromatography-mass spectrometer (GC-MS). MSD was set for selective ion monitoring of peaks at m/e 84, 189, and 300. The enantiomers of each racemic pair were baseline resolved to give >99% optical purity for all d-threo enantiomers and 96% optical purity for all l-threo enantiomers. The retention times for the (S)-MTPA derivatives of these compounds were: d-threo 1, 20.91 min; l-threo 1, 20.79 min; d-threo 2, 24.22 min; l-threo 2, 24.03 min; d-threo 3, 23.68 min; l-threo 3, 23.51 min.

If the compound of the present invention contains one or more chiral centers, the compound can be synthesized enantioselectively or a mixture of enantiomers and/or diastereomers can be prepared and separated. The resolution of the compounds of the present invention, their starting materials and/or the intermediates may be carried out by known procedures, e.g., as described in the four volume compendium *Optical Resolution Procedures for Chemical Compounds Optical Resolution Information Center*, Manhattan College, Riverdale, N.Y., and in *Enantiomers, Racemates and Resolutions*, Jean Jacques, Andre Collet and Samuel H. Wilen; John Wiley & Sons, Inc., New York, 1981, which are incorporated herein in their entirety. Basically, the resolution of the compounds is based on the differences in the physical properties of diastereomers by attachment, either chemically or enzymatically, of an enantiomerically pure moiety, resulting in forms that are separable by fractional crystallization, distillation or chromatography.

The pharmaceutically-acceptable salts of the compounds of formula I may also be used in the practice of the invention. Pharmaceutically-acceptable salts include conventional non-toxic salts, such as salts derived from inorganic acids (such as hydrochloric, hydrobromic, sulfuric, phosphoric, nitric, and the like), organic acids (such as acetic, propionic, succinic, glycolic, stearic, lactic, malic, tartaric, citric, glutamic, aspartic, benzoic, salicylic, oxalic, ascorbic acid, and the like) or bases (such as the hydroxide, carbonate or bicarbonate of a pharmaceutically-acceptable metal cation or organic cations derived from N,N-dibenzylethylenediamine, D-glucosamine, or ethylenediamine). The salts are prepared in a conventional manner, e.g., by reacting the free base form of the compound with an acid.

It is to be understood that the scope of this invention encompasses not only the use of the compounds of formula I themselves, but also the salts and prodrugs thereof. In addition, the present invention contemplates the use of the isomers of the compounds of formula I, and of the salts and prodrugs thereof, including pure isomers and various mixtures of isomers.

Compounds of formula I, pharmaceutically-acceptable salts thereof or prodrugs thereof, can be used to inhibit angiogenesis. Angiogenesis is the process of new blood vessel formation in the body. Angiogenesis is also used herein to mean the same as, or to include, neovascularization, vascularization, arterialization and vasculogenesis.

Compounds of formula I, pharmaceutically-acceptable salts thereof or prodrugs thereof, can also be used to treat angiogenic diseases and conditions. An angiogenic disease or condition is a disease or condition involving, caused by, exacerbated by, or dependent on, angiogenesis. Specific angiogenic diseases and conditions treatable according to the invention include neoplastic diseases, hypertrophy (e.g., cardiac hypertrophy induced by thyroid hormone), connective tissue disorders (e.g., rheumatoid arthritis and atherosclerosis), psoriasis, ocular angiogenic diseases, cardiovascular diseases, cerebral vascular diseases, endometriosis, polyposis, obesity, diabetes-associated diseases and hemophiliac joints. The compounds of formula I, pharmaceutically-acceptable salts thereof or prodrugs thereof, can also be used to inhibit the vascularization required for embryo implantation, thereby providing a method of birth control.

The compounds of formula I, pharmaceutically-acceptable salts thereof or prodrugs thereof, will be particularly useful for the treatment of ocular angiogenic diseases. Ocular angiogenic diseases include diabetic retinopathy, retinopathy of prematurity, macular degeneration, corneal graft rejection, neovascular glaucoma, retrolental fibroplasias, and rubeosis. The compounds of formula I, pharmaceutically-acceptable salts thereof or prodrugs thereof, will be especially useful for the treatment of diabetic retinopathy and macular degeneration.

The compounds of formula I, pharmaceutically-acceptable salts thereof or prodrugs thereof, will also be particularly useful for the treatment of neoplastic diseases. Neoplastic diseases treatable with the compounds of formula I, pharmaceutically-acceptable salts thereof or prodrugs thereof, include malignant tumors (e.g., tumors of the bladder, brain, breast, cervix, colon, rectum, kidney, liver, lung, ovary, pancreas, prostate, stomach and uterus), tumor metastasis, and benign tumors (e.g., hemangiomas, acoustic neuromas, neurofibromas, trachomas and pyrogenic granulomas)). The compounds of formula I, pharmaceutically-acceptable salts thereof or prodrugs thereof, will be especially useful for the treatment of tumors of the brain, breast, colon, liver and pancreas, most especially tumors of the brain (e.g., glioblastomas).

In addition to being able to inhibit angiogenesis, the compounds of formula I, pharmaceutically-acceptable salts thereof or prodrugs thereof, have been found to be able to inhibit the proliferation of cells, reduce the growth of cancer cells, inhibit the production of cytokines, inhibit Ras and RAP-1, and inhibit the production of NFκB and AP-1. Thus, the compounds of formula I, pharmaceutically-acceptable salts thereof or prodrugs thereof, will also be particularly useful for the treatment of a variety of proliferative disorders, including angiogenic diseases and conditions, especially neoplastic diseases (see above), and other cancers and other proliferative disorders.

Cancers treatable with the compounds of formula I, pharmaceutically-acceptable salts thereof or prodrugs thereof, include carcinomas, sarcomas, lymphomas, leukemias, solid tumors and hematologic malignancies. Specific cancers treatable with the compounds of formula I, pharmaceutically-acceptable salts thereof or prodrugs thereof, include brain cancers, head and neck cancers, breast cancers, ovarian cancers, prostate cancers, gastric cancers, colon cancers, pancreatic cancers, bladder cancers, thyroid cancers, hepatic cancers, lung cancers, bone cancers and skin cancers. The compounds of formula I, pharmaceutically-acceptable salts thereof or prodrugs thereof, will be especially useful for the treatment of brain cancers, breast cancers, colon cancers, liver cancers, pancreatic cancers, skin cancers, lymphomas and leukemias.

Other proliferative disorders include mesangial cell proliferation disorders, fibrotic disorders and hyperproliferative skin disorders. Mesangial cell proliferative disorders refer to disorders brought about by abnormal proliferation of mesangial cells. Mesangial cell proliferative disorders include renal diseases, such as glomerulonephritis, diabetic nephropathy, malignant nephrosclerosis, thrombotic microangiopathy syndromes and glomerulopathies. Fibrotic disorders refer to the abnormal formation of extracellular matrices. Examples of fibrotic disorders include hepatic cirrhosis, pulmonary fibrosis and atherosclerosis. Hyperproliferative skin disorders include psoriasis, skin cancer and epidermal hyperproliferation.

To treat an animal in need of treatment, a compound of formula I, pharmaceutically-acceptable salt thereof or prodrug thereof, is administered to the animal. Preferably, the animal is a mammal, such as a rabbit, goat, dog, cat, horse or human. Most preferably, the animal is a human.

Effective dosage forms, modes of administration and dosage amounts for the compounds of the invention may be determined empirically, and making such determinations is within the skill of the art. It is understood by those skilled in the art that the dosage amount will vary with the particular compound employed, the disease or condition to be treated, the severity of the disease or condition, the route(s) of administration, the rate of excretion of the compound, the duration of the treatment, the identify of any other active ingredient(s)s being administered to the animal, the age, size and species of the animal, and like factors known in the medical and veterinary arts. In general, a suitable daily dose of a compound of the present invention will be that amount of the compound which is the lowest dose effective to produce a therapeutic effect. However, the daily dosage will be determined by an attending physician or veterinarian within the scope of sound medical judgment. If desired, the effective daily dose may be administered as two, three, four, five, six or more sub-doses, administered separately at appropriate intervals throughout the day. Administration of the compound should be continued until an acceptable response is achieved.

The compounds useful in the present invention (i.e., the compounds of formula I and the pharmaceutically-acceptable salts and prodrugs thereof) may be administered to an animal patient for therapy by any suitable route of administration, including orally, nasally, rectally, vaginally, parenterally (e.g., intravenously, intraspinally, intraperitoneally, subcutaneously, or intramuscularly), intracisternally, transdermally, intracranially, intracerebrally, and topically (including buccally and sublingually). The preferred routes of administration are orally and topically.

While it is possible for a compound useful in the present invention to be administered alone, it is preferable to administer the compound as a pharmaceutical formulation (composition). The pharmaceutical compositions useful in the invention comprise one or more compounds of formula I, or pharmaceutically-acceptable salts or prodrugs thereof, as active ingredient(s) in admixture with one or more pharmaceutically-acceptable carriers and, optionally, with one or more other compounds, active ingredient(s) or other materials. Each carrier must be "acceptable" in the sense of being compatible with the other ingredients of the formulation and not injurious to the animal. Pharmaceutically-acceptable carriers are well known in the art. Regardless of the route of administration selected, the compounds of the present invention are formulated into pharmaceutically-acceptable dosage forms by conventional methods known to those of skill in the art. See, e.g., *Remington's Pharmaceutical Sciences*.

Formulations of the invention suitable for oral administration may be in the form of capsules, cachets, pills, tablets, powders, granules or as a solution or a suspension in an aqueous or non-aqueous liquid, or an oil-in-water or water-in-oil liquid emulsions, or as an elixir or syrup, or as pastilles (using an inert base, such as gelatin and glycerin, or sucrose and acacia), and the like, each containing a predetermined amount of a compound or compounds useful in the present invention as an active ingredient. A compound or compounds useful in the present invention may also be administered as bolus, electuary or paste.

In solid dosage forms for oral administration (capsules, tablets, pills, dragees, powders, granules and the like), the active ingredient(s) is (are) mixed with one or more pharmaceutically acceptable carriers, such as sodium citrate or dicalcium phosphate, and/or any of the following: (1) fillers or extenders, such as starches, lactose, sucrose, glucose, mannitol, and/or silicic acid; (2) binders, such as, for example, carboxymethylcellulose, alginates, gelatin, polyvinyl pyrrolidone, sucrose and/or acacia; (3) humectants, such as glycerol; (4) disintegrating agents, such as agar-agar, calcium carbonate, potato or tapioca starch, alginic acid, certain silicates, and sodium carbonate; (5) solution retarding agents, such as paraffin; (6) absorption accelerators, such as quaternary ammonium compounds; (7) wetting agents, such as, for example, cetyl alcohol and glycerol monosterate; (8) absorbents, such as kaolin and bentonite clay; (9) lubricants, such as talc, calcium stearate, magnesium stearate, solid polyethylene glycols, sodium lauryl sulfate, and mixtures thereof; and (10) coloring agents. In the case of capsules, tablets and pills, the pharmaceutical compositions may also comprise buffering agents. Solid compositions of a similar type may be employed as fillers in soft and hard-filled gelatin capsules using such excipients as lactose or milk sugars, as well as high molecular weight polyethylene glycols and the like.

A tablet may be made by compression or molding optionally with one or more accessory ingredients. Compressed tablets may be prepared using binder (for example, gelatin or hydroxypropylmethyl cellulose), lubricant, inert diluent, preservative, disintegrant (for example, sodium starch glycolate or cross-linked sodium carboxymethyl cellulose), surface-active or dispersing agent. Molded tablets may be made by molding in a suitable machine a mixture of the powdered compound moistened with an inert liquid diluent.

The tablets, and other solid dosage forms of the pharmaceutical compositions of the present invention, such as dragees, capsules, pills and granules, may optionally be scored or prepared with coatings and shells, such as enteric coatings and other coatings well known in the pharmaceutical-formulating art. They may also be formulated so as to provide slow or controlled release of the active ingredient therein using, for example, hydroxypropylmethyl cellulose in varying proportions to provide the desired release profile, other polymer matrices, liposomes and/or microspheres. They may be sterilized by, for example, filtration through a bacteria-retaining filter. These compositions may also optionally contain opacifying agents and may be of a composition that they release the active ingredient only, or preferentially, in a certain portion of the gastrointestinal tract, optionally, in a delayed manner. Examples of embedding compositions which can be used include polymeric substances and waxes. The active ingredient can also be in microencapsulated form.

Liquid dosage forms for oral administration of the compounds of the invention include pharmaceutically-acceptable emulsions, microemulsions, solutions, suspensions, syrups and elixirs. In addition to the active ingredient(s), the liquid dosage forms may contain inert diluents commonly used in the art, such as, for example, water or other solvents, solubilizing agents and emulsifiers, such as ethyl alcohol, isopropyl alcohol, ethyl carbonate, ethyl acetate, benzyl alcohol, benzyl benzoate, propylene glycol, 1,3-butylene glycol, oils (in particular, cottonseed, groundnut, corn, germ, olive, castor and sesame oils), glycerol, tetrahydrofuryl alcohol, polyethylene glycols and fatty acid esters of sorbitan, and mixtures thereof.

Besides inert diluents, the oral compositions can also include adjuvants such as wetting agents, emulsifying and suspending agents, sweetening, flavoring, coloring, perfuming and preservative agents.

Suspensions, in addition to the active compound(s), may contain suspending agents as, for example, ethoxylated isostearyl alcohols, polyoxyethylene sorbitol and sorbitan esters, microcrystalline cellulose, aluminum metahydroxide, bentonite, agar-agar and tragacanth, and mixtures thereof.

Pharmaceutical formulations for intraocular injection of a compound or compounds of the invention into the eyeball include solutions, emulsions, suspensions, particles, capsules, microspheres, liposomes, matrices, etc. See, e.g., U.S. Pat. No. 6,060,463, U.S. Patent Application Publication No. 2005/0101582, and PCT application WO 2004/043480, the complete disclosures of which are incorporated herein by reference. For instance, a pharmaceutical formulation for intraocular injection may comprise one or more compounds of the invention in combination with one or more pharmaceutically-acceptable sterile isotonic aqueous or non-aqueous solutions, suspensions or emulsions, which may contain antioxidants, buffers, suspending agents, thickening agents or viscosity-enhancing agents (such as a hyaluronic acid polymer). Examples of suitable aqueous and nonaqueous carriers include water, saline (preferably 0.9%), dextrose in water (preferably 5%), buffers, dimethylsulfoxide, alcohols and polyols (such as glycerol, propylene glycol, polyethylene glycol, and the like). These compositions may also contain adjuvants such as wetting agents and emulsifying agents and dispersing agents. In addition, prolonged absorption of the injectable pharmaceutical form may be brought about by the inclusion of agents which delay absorption such as polymers and gelatin. Injectable depot forms can be made by incorporating the drug into microcapsules or microspheres made of biodegradable polymers such as polylactide-polyglycolide. Examples of other biodegradable polymers include poly(orthoesters), poly(glycolic) acid, poly(lactic) acid, polycaprolactone and poly(anhydrides). Depot injectable formulations are also prepared by entrapping the drug in liposomes (composed of the usual ingredients, such as dipalmitoyl phosphatidylcholine) or microemulsions which are compatible with eye tissue. Depending on the ratio of drug to polymer or lipid, the nature of the particular polymer or lipid components, the type of liposome employed, and whether the microcapsules or microspheres are coated or uncoated, the rate of drug release from microcapsules, microspheres and liposomes can be controlled.

The compounds of the invention can also be administered surgically as an ocular implant. For instance, a reservoir container having a diffusible wall of polyvinyl alcohol or polyvinyl acetate and containing a compound or compounds of the invention can be implanted in or on the sclera. As another example, a compound or compounds of the invention can be incorporated into a polymeric matrix made of a polymer, such as polycaprolactone, poly(glycolic) acid, poly(lactic) acid, poly(anhydride), or a lipid, such as sebacic acid, and may be implanted on the sclera or in the eye. This is usually accomplished with the animal receiving a topical or local anesthetic and using a small incision made behind the cornea. The matrix is then inserted through the incision and sutured to the sclera.

A preferred embodiment of the invention is local topical administration of the compounds of the invention to the eye, and a particularly preferred embodiment of the invention is a topical pharmaceutical composition suitable for application to the eye. Topical pharmaceutical compositions suitable for application to the eye include solutions, suspensions, dispersions, drops, gels, hydrogels and ointments. See, e.g., U.S. Pat. No. 5,407,926 and PCT applications WO 2004/058289, WO 01/30337 and WO 01/68053, the complete disclosures of all of which are incorporated herein by reference.

Topical formulations suitable for application to the eye for treatment of an angiogenic disease or condition comprise one or more compounds of the invention in an aqueous or nonaqueous base. The topical formulations can also include absorption enhancers, permeation enhancers, thickening agents, viscosity enhancers, agents for adjusting and/or maintaining the pH, agents to adjust the osmotic pressure, preservatives, surfactants, buffers, salts (preferably sodium chloride), suspending agents, dispersing agents, solubilizing agents, stabilizers and/or tonicity agents. Topical formulations suitable for application to the eye for treatment of an angiogenic disease or condition will preferably comprise an absorption or permeation enhancer to promote absorption or permeation of the compound or compounds of the invention into the eye and/or a thickening agent or viscosity enhancer that is capable of increasing the residence time of a compound or compounds of the invention in the eye. See PCT applications WO 2004/058289, WO 01/30337 and WO 01/68053. Exemplary absorption/permeation enhancers include methysulfonylmethane, alone or in combination with dimethylsulfoxide, carboxylic acids and surfactants. Exemplary thickening agents and viscosity enhancers include dextrans, polyethylene glycols, polyvinylpyrrolidone, polysaccharide gels, Gelrite®, cellulosic polymers (such as hydroxypropyl methylcellulose), carboxyl-containing polymers (such as polymers or copolymers of acrylic acid), polyvinyl alcohol and hyaluronic acid or a salt thereof.

Liquid dosage forms (e.g., solutions, suspensions, dispersions and drops) can be prepared, for example, by dissolving, dispersing, suspending, etc. a compound or compounds of the invention in a vehicle, such as, for example, water, saline, aqueous dextrose, glycerol, ethanol and the like, to form a solution, dispersion or suspension. If desired, the pharmaceutical formulation may also contain minor amounts of non-toxic auxillary substances, such as wetting or emulsifying agents, pH buffering agents and the like, for example sodium acetate, sorbitan monolaurate, triethanolamine sodium acetate, triethanolamine oleate, etc.

Aqueous solutions and suspensions can include, in addition to a compound or compounds of the invention, preservatives, surfactants, buffers, salts (preferably sodium chloride), tonicity agents and water. If suspensions are used, the particle sizes should be less than 10 µm to minimize eye irritation. If solutions or suspensions are used, the amount delivered to the eye should not exceed 50 µl to avoid excessive spillage from the eye.

Colloidal suspensions are generally formed from microparticles (i.e., microspheres, nanospheres, microcapsules or nanocapsules, where microspheres and nanospheres are generally monolithic particles of a polymer matrix in which the formulation is trapped, adsorbed, or otherwise contained, while with microcapsules and nanocapsules the formulation is actually encapsulated). The upper limit for the size of these microparticles is about 5µ to about 10µ.

Ophthalmic ointments include a compound or compounds of the invention in an appropriate base, such as mineral oil, liquid lanolin, white petrolatum, a combination of two or all three of the foregoing, or polyethylene-mineral oil gel. A preservative may optionally be included.

Ophthalmic gels include a compound or compounds of the invention suspended in a hydrophilic base, such as Carpobol-940 or a combination of ethanol, water and propylene glycol (e.g., in a ratio of 40:40:20). A gelling agent, such as hydroxylethylcellulose, hydroxypropylcellulose, hydroxypropylmethylcellulose or ammoniated glycyrrhizinate, is used. A preservative and/or a tonicity agent may optionally be included.

Hydrogels are formed by incorporation of a swellable, gel-forming polymer, such as those listed above as thickening agents or viscosity enhancers, except that a formulation referred to in the art as a "hydrogel" typically has a higher viscosity than a formulation referred to as a "thickened" solution or suspension. In contrast to such preformed hydrogels, a formulation may also be prepared so to form a hydrogel in situ following application to the eye. Such gels are liquid at room temperature but gel at higher temperatures (and thus are termed "thermoreversible" hydrogels), such as when placed in contact with body fluids. Biocompatible polymers that impart this property include acrylic acid polymers and copolymers, N-isopropylacrylamide derivatives and ABA block copolymers of ethylene oxide and propylene oxide (conventionally referred to as "poloxamers" and available under the Pluronic® tradename from BASF-Wayndotte).

Preferred dispersions are liposomal, in which case the formulation is enclosed within liposomes (microscopic vesicles composed of alternating aqueous compartments and lipid bilayers).

Eye drops can be formulated with an aqueous or non-aqueous base also comprising one or more dispersing agents, solubilizing agents or suspending agents. Drops can be delivered by means of a simple eye dropper-capped bottle or by means of a plastic bottle adapted to deliver liquid contents dropwise by means of a specially shaped closure.

The compounds of the invention can also be applied topically by means of drug-impregnated solid carrier that is inserted into the eye. Drug release is generally effected by dissolution or bioerosion of the polymer, osmosis, or combinations thereof. Several matrix-type delivery systems can be used. Such systems include hydrophilic soft contact lenses impregnated or soaked with the desired compound of the invention, as well as biodegradable or soluble devices that need not be removed after placement in the eye. These soluble ocular inserts can be composed of any degradable substance that can be tolerated by the eye and that is compatible with the compound of the invention that is to be administered. Such substances include, but are not limited to, poly(vinyl alcohol), polymers and copolymers of polyacrylamide, ethylacrylate and vinylpyrrolidone, as well as cross-linked polypeptides or polysaccharides, such as chitin.

Dosage forms for the other types of topical administration (i.e., not to the eye) or for transdermal administration of compounds of the invention include powders, sprays, ointments, pastes, creams, lotions, gels, solutions, patches, drops and inhalants. The active ingredient may be mixed under sterile conditions with a pharmaceutically-acceptable carrier, and with any buffers, or propellants which may be required. The ointments, pastes, creams and gels may contain, in addition to the active ingredient, excipients, such as animal and vegetable fats, oils, waxes, paraffins, starch, tragacanth, cellulose derivatives, polyethylene glycols, silicones, bentonites, silicic acid, talc and zinc oxide, or mixtures thereof. Powders and sprays can contain, in addition to the active ingredient, excipients such as lactose, talc, silicic acid, aluminum hydroxide, calcium silicates and polyamide powder or mixtures of these substances. Sprays can additionally contain customary propellants such as chlorofluorohydrocarbons and volatile unsubstituted hydrocarbons, such as butane and propane. Transdermal patches have the added advantage of providing controlled delivery of compounds of the invention to the body. Such dosage forms can be made by dissolving, dispersing or otherwise incorporating one or more compounds of the invention in a proper medium, such as an elastomeric matrix material. Absorption enhancers can also be used to increase the flux of the compound across the skin. The rate of such flux can be controlled by either providing a rate-controlling membrane or dispersing the compound in a polymer matrix or gel.

Formulations of the pharmaceutical compositions for rectal or vaginal administration may be presented as a suppository, which may be prepared by mixing one or more compounds of the invention with one or more suitable nonirritating excipients or carriers comprising, for example, cocoa butter, polyethylene glycol, a suppository wax or salicylate, and which is solid at room temperature, but liquid at body temperature and, therefore, will melt in the rectum or vaginal cavity and release the active compound. Formulations of the present invention which are suitable for vaginal administration also include pessaries, tampons, creams, gels, pastes, foams or spray formulations containing such carriers as are known in the art to be appropriate.

Pharmaceutical formulations include those suitable for administration by inhalation or insufflation or for nasal or intraocular administration. For administration to the upper (nasal) or lower respiratory tract by inhalation, the compounds of the invention are conveniently delivered from an insufflator, nebulizer or a pressurized pack or other convenient means of delivering an aerosol spray. Pressurized packs may comprise a suitable propellant such as dichlorodifluoromethane, trichlorofluoromethane, dichlorotetrafluoroethane, carbon dioxide, or other suitable gas. In the case of a pressurized aerosol, the dosage unit may be determined by providing a valve to deliver a metered amount.

Alternatively, for administration by inhalation or insufflation, the composition may take the form of a dry powder, for example, a powder mix of one or more compounds of the invention and a suitable powder base, such as lactose or starch. The powder composition may be presented in unit dosage form in, for example, capsules or cartridges, or, e.g., gelatin or blister packs from which the powder may be administered with the aid of an inhalator, insufflator or a metered-dose inhaler.

For intranasal administration, compounds useful in the invention may be administered by means of nose drops or a liquid spray, such as by means of a plastic bottle atomizer or metered-dose inhaler. Liquid sprays are conveniently delivered from pressurized packs. Typical of atomizers are the Mistometer (Wintrop) and Medihaler (Riker).

Drops, such as eye drops or nose drops, may be formulated with an aqueous or nonaqueous base also comprising one or more dispersing agents, solubilizing agents or suspending agents. Drops can be delivered by means of a simple eye dropper-capped bottle or by means of a plastic bottle adapted to deliver liquid contents dropwise by means of a specially shaped closure.

Pharmaceutical compositions suitable for parenteral administrations comprise one or more compounds useful in the invention in combination with one or more pharmaceutically-acceptable sterile isotonic aqueous or non-aqueous solutions, dispersions, suspensions or emulsions, or sterile powders which may be reconstituted into sterile injectable solutions or dispersions just prior to use, which may contain antioxidants, buffers, solutes which render the formulation isotonic with the blood of the intended recipient or suspending or thickening agents.

Examples of suitable aqueous and nonaqueous carriers which may be employed in the pharmaceutical compositions of the invention include water, ethanol, polyols (such as glycerol, propylene glycol, polyethylene glycol, and the like), and suitable mixtures thereof, vegetable oils, such as olive oil, and injectable organic esters, such as ethyl oleate. Proper fluidity can be maintained, for example, by the use of coating materials, such as lecithin, by the maintenance of the required particle size in the case of dispersions, and by the use of surfactants.

These compositions may also contain adjuvants such as wetting agents, emulsifying agents and dispersing agents. It may also be desirable to include isotonic agents, such as sugars, sodium chloride, and the like in the compositions. In addition, prolonged absorption of the injectable pharmaceutical form may be brought about by the inclusion of agents which delay absorption such as aluminum monosterate and gelatin.

In some cases, in order to prolong the effect of the active ingredient(s), it is desirable to slow the absorption of the active ingredient(s) from subcutaneous or intramuscular injection. This may be accomplished by the use of a liquid suspension of crystalline or amorphous material having poor water solubility. The rate of absorption of the active ingredient(s) then depends upon its rate of dissolution which, in turn, may depend upon crystal size and crystalline form. Alternatively, delayed absorption of a parenterally-administered active ingredient(s) is accomplished by dissolving or suspending the active ingredient(s) in an oil vehicle.

Injectable depot forms are made by forming microencapsule matrices of the active ingredient(s) in biodegradable polymers such as polylactide-polyglycolide. Depending on the ratio of active ingredient(s) to polymer, and the nature of the particular polymer employed, the rate of release of the active ingredient(s) can be controlled. Examples of other biodegradable polymers include poly(orthoesters) and poly (anhydrides). Depot injectable formulations are also prepared by entrapping the active ingredient(s) in liposomes or microemulsions which are compatible with body tissue. The injectable materials can be sterilized for example, by filtration through a bacterial-retaining filter.

The formulations may be presented in unit-dose or multi-dose sealed containers, for example, ampules and vials, and may be stored in a lyophilized condition requiring only the addition of the sterile liquid carrier, for example water for injection, immediately prior to use. Extemporaneous injection solutions and suspensions may be prepared from sterile powders, granules and tablets of the type described above.

Additional objects, advantages, and novel features of this invention will become apparent to those skilled in the art upon examination of the following examples thereof, which are not intended to be limiting.

EXAMPLES

Example 1

Whole blood was drawn from GR283, a human volunteer with known allergies, into a glass vacutainer tube containing no anticoagulant. This blood was allowed to clot, and the serum was removed by centrifugation and then heat inactivated by placing it in a water bath at 56° C. for 30 minutes. Whole blood from GR283 was also drawn into a glass vacutainer tube containing heparin and used for peripheral blood lymphocytes (PBL) isolation as follows. Whole blood was layered over room temperature Histopaque 1077 solution and centrifuged at 2000 rpm for 15 minutes at room temperature. Cells at the plasma-Histopaque interface were then removed and washed with culture medium (IMDM medium with 10% heat-inactivated GR283 serum plus 1% penicillin/streptomycin) at 37° C.

The compound of formula II (see above) and methylphenidate (both obtained from Dr. Jeffrey D. Winkler, University of Pennsylvania, Philadelphia, Pa.) in culture medium were added to wells of a 96-well plate to give final concentrations of 5 µg/ml, 15 µg/ml and 50 µg/ml of the compound of formula II and of methylphenidate. Sterile 18 MS2 water, the solvent for the compound of formula II, and dexamethasone (obtained from Sigma) (final concentration of 10 µg/ml in water) were used as controls. Then, GR283's PBL in culture medium were added to the wells to give a final concentration of 150,000 cells per well, and the plates were incubated at 37° C., 5% $CO_2$ for 24 hours. After this incubation, phytohemagglutinin (PHA) in culture medium was added to give final concentrations of 2 µg/ml, 5 µg/ml or 20 µg/ml, final total volume of 200 µl/well, and the cells were incubated for an additional 72 hours at 37° C., 5% $CO_2$. All cultures were performed in triplicate.

At the end of this incubation, cell clumping was examined by photographing representative wells with a digital camera mounted to an inverted microscope. The compound of formula II reduced the amount of cell clumping induced by 5 µg/ml PHA in a dose-dependent manner. The compound of formula II attenuated cell clumping, presumably, as a result of decreased expression of cellular adhesion molecules on the surfaces of the cells.

Figure 1B:
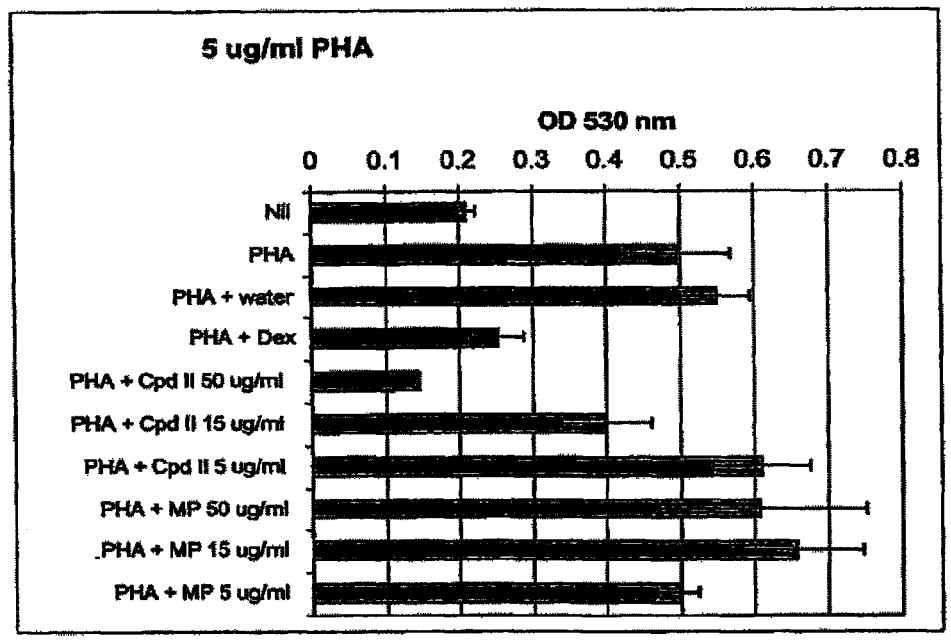
Figure 1C:
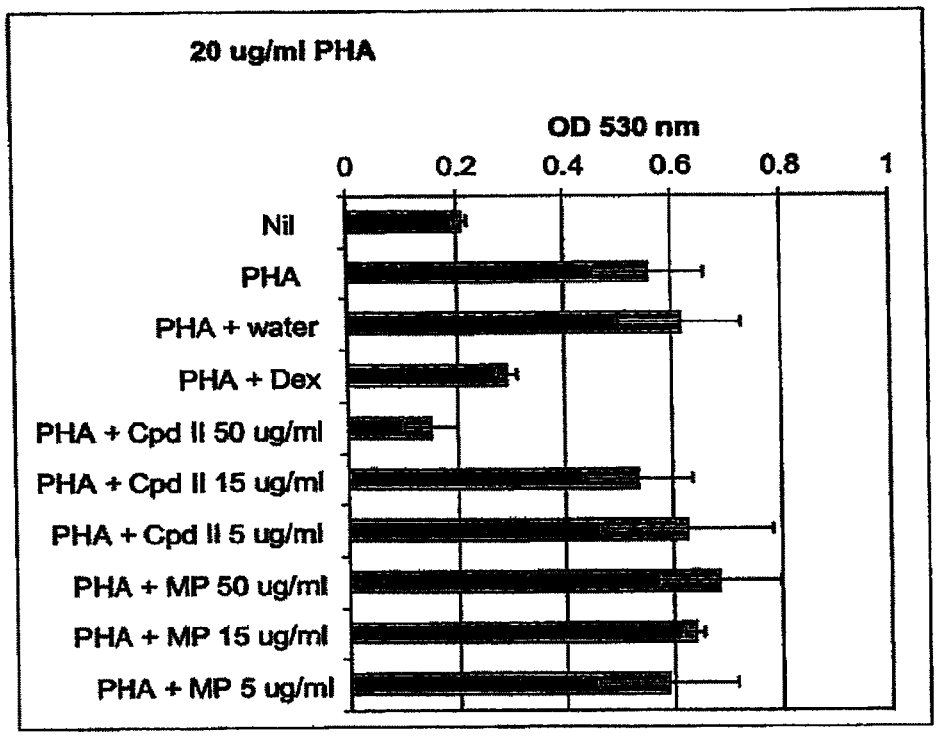

Cell proliferation was assayed by adding 20 µl of Promega cell titer solution to each well and incubating the plate for an additional 4 hours. Promega cell titer solution is a solution containing a tetrazolium dye that is reduced by living cells to a formazan dye, and this reduction is proportional to the number of living cells present in the well. After the 4-hour incubation, the optical density (OD) at 530 nm of each well was measured. The OD at 530 nm for blank wells containing no cells was subtracted from the OD of the experimental wells. The results of the proliferation assays are presented in FIGS. 1A-C. As can be seen from FIGS. 1A-C, the compound of formula II (Cpd. II) and dexamethasone (Dex) significantly inhibited the proliferation of PBL stimulated with PHA in a dose-dependent manner. Methylphenidate (MP) showed a significant effect at its highest dose and the lowest PHA dose. Otherwise, methylphenidate did not significantly reduce the proliferation of the PHA-stimulated PBL.

Example 2

Whole blood was drawn from GR467, a human volunteer with known allergies, and processed as described in Example 1 to give heat-inactivated serum and PBL. The compound of formula II and methylphenidate in culture medium (made using heat-inactivated GR467 serum) were added to wells of a 96-well plate to give final concentrations of 5 µg/ml, 15 µg/ml and 25 µg/ml of the compound of formula II and 15 µg/ml methylphendiate. Water and dexamethasone (final concentration of 10 µM) were used as controls. Then, GR467's PBL in culture medium were added to the wells to give a final concentration of 150,000 cells per well, and the plates were incubated at 37° C., 5% $CO_2$ for 24 hours. After this incubation, PHA was added to give a final concentration of 2 µg/ml, final total volume of 200 µl/well, and the cells were incubated for an additional 72 hours at 37° C., 5% $CO_2$. All cultures were performed in triplicate.

Figure 2:
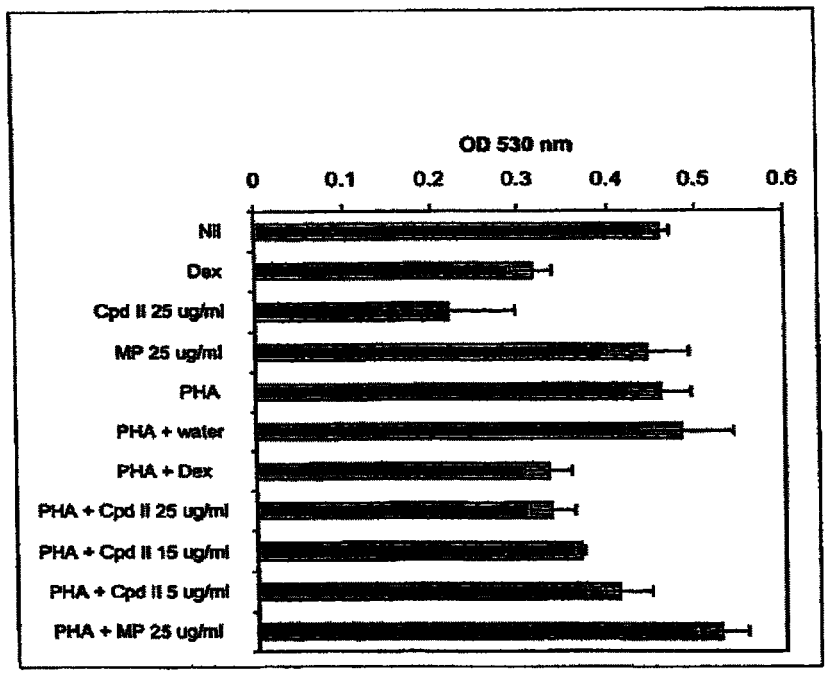
FIG. 2 is a graph of OD at 530 nm for various additives to PBL cultures stimulated with 2 µg/ml PHA.

At the end of this incubation, cell proliferation was determined as described in Example 1. The results are presented in FIG. 2. As can be seen from FIG. 2, the compound of formula II (Cpd II) and dexamethasone (Dex) significantly inhibited the proliferation of PBL, both unstimulated and stimulated with PHA, whereas methylphenidate did not.

The release of cytokines by the PBL was also measured by culturing the PBL in 1 ml tubes, at $1.3 \times 10^6$ cells per ml, with 15 µg/ml of the compound of formula II, 15 µg/ml methylphenidate or 10 µM dexamethasone at 37° C., 5% $CO_2$ for 24 hours. After this incubation, PHA was added to give a final concentration of 2 µg/ml, and the cells were incubated for an additional 96 hours at 37° C., 5% $CO_2$. All cultures were performed in triplicate. Cells were then removed by centrifugation at 1000 rpm for 10 minutes, and the culture medium collected.

IL-13 is made by activated $T_H2$ cells, and IL-13's primary targets are B-cells and monocytes. IL-13 stimulates humoral immune responses, and it has been implicated in the pathogenesis of asthma. IL-13 is secreted by lymphoma cell lines and may be an autocrine growth factor. IL-13 is also expressed in pancreatic cancer. However, IL-13 has also been reported to inhibit the growth of other types of tumors, such as gliomas and renal cell carcinomas IFNγ is a proinflammatory cytokine made by activated T-cells and other cells. IFNγ can activate neutrophils, endothelial cells and macrophages, as well as cause an increase in MHC molecule expression. IFNγ drives the cell-mediated immune response. IFNγ plays an important role in the immune-mediated rejection of established tumors. IFNγ has antiproliferative effects on some tumors, can have apoptotic effects on others, can induce the production of angiostatic chemokines and enhances the immunogenicity of tumor cells.

Release of IL-13 and interferon gamma (IFNγ) into the culture medium was measured by ELISA. To perform the ELISA, matched pairs of antibodies against human IL-13 and IFNγ were purchased from Pierce Biotechnology and Biosource, respectively. ELISA strip well plates were coated with 10 µg/ml of antibody (in phosphate-buffered saline (PBS)) to IL-13 and 4 µg/ml of antibody to IFNγ (in PBS) overnight at room temperature. The plates were then blocked using a 4% BSA solution in PBS for one hour, followed by the addition of 50 µl of experimental culture medium per well in duplicate. The plates were incubated at room temperature for one hour and then washed using 50 mM Tris pH 8.0 with 0.1% Tween 20. Then, solutions of 400 ng/ml biotinylated second antibody to IL-13 and 500 ng/ml biotinylated second antibody to IFNγ were made in blocking buffer, and 100 µl were added per well. The plates were incubated for 1 hour and washed again. A 1:8000 dilution of Strepavidin HRP (Pierce Biotechnology) conjugate was made in blocking buffer, and 100 µl were added to the wells and incubation continued for 30 minutes. A final wash step was performed, after which 100 µl Pierce Biotechnology TMB substrate were added to each well. Color was developed for 30 minutes and stopped by adding 100 µl 0.18 N $H_2SO_4$. OD was determined using microplate reader with a 450 nM filter.

Figure 3:
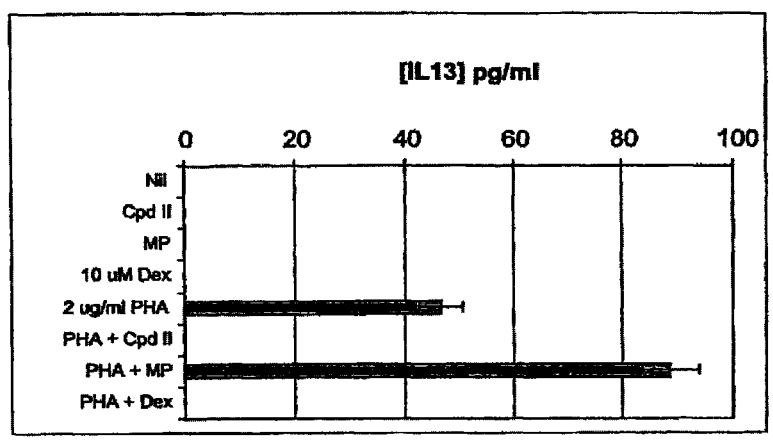
FIG. 3 is a graph of concentration of IL-13 for various additives to PBL cultures stimulated with 2 µg/ml PHA.

The results for IL-13 are shown in FIG. 3. As can be seen, the compound of formula II (Cpd. II) and dexamethasone (Dex) significantly inhibited IL-13 release induced by PHA. Methylphenidate (MP) did not inhibit the release of IL-13. Indeed, methylphenidate increased the release of IL-13 by the PHA-stimulated cells.

Figure 4:
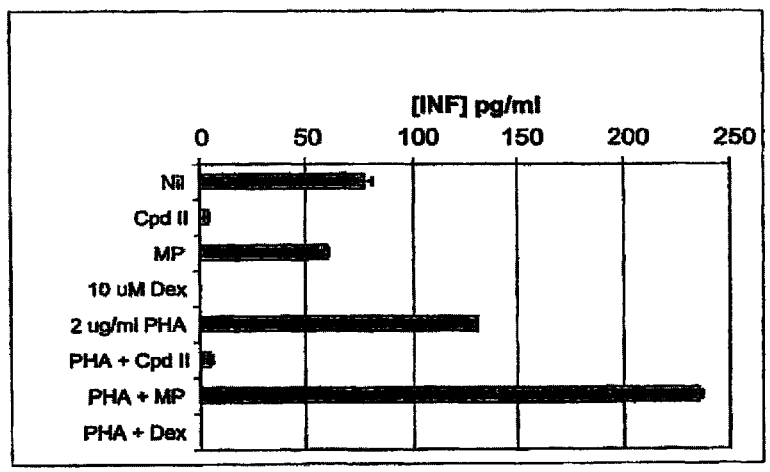
FIG. 4 is a graph of concentration of IFNγ for various additives to PBL cultures stimulated with 2 µg/ml PHA.

The results for IFNγ are shown in FIG. 4. As can be seen, the compound of formula II (Cpd. II) and dexamethasone (Dex) significantly inhibited IFNγ release in both unstimulated cells and in cells stimulated with PHA. Methylphenidate (MP) had some effect on the release of IFNγ by unstimulated cells, but did not significantly suppress the release of IFNγ from cells stimulated with PHA. Indeed, methylphenidate increased the release of IFNγ by the PHA-stimulated cells.

Example 3

Whole blood was drawn from GR191, a normal human volunteer, and processed as described in Example 1 to give heat-inactivated serum and PBL. The compound of formula II and methylphenidate in culture medium (made using heat-inactivated GR191 serum) were added to wells of a 96-well plate to give final concentrations of 5 µg/ml, 15 µg/ml, 25 µg/ml and 50 µg/ml of the compound of formula II and 50 µg/ml methylphendiate. Water, mouse nerve growth factor (Upstate Biotechnology, Inc) (NGF) (final concentration of 250 ng/ml) and dexamethasone (final concentration of 10 µM) were used as controls. Then, GR191's PBL in culture medium were added to the wells to give a final concentration of 150,000 cells per well, and the plates were incubated at 37° C., 5% $CO_2$ for 24 hours. After this incubation, PHA was added to give final concentrations of 2 µg/ml and 5 µg/ml, final total volume of 200 µl/well, and the cells were incubated for an additional 72 hours at 37° C., 5% $CO_2$. All cultures were performed in triplicate.

Figure 5A:
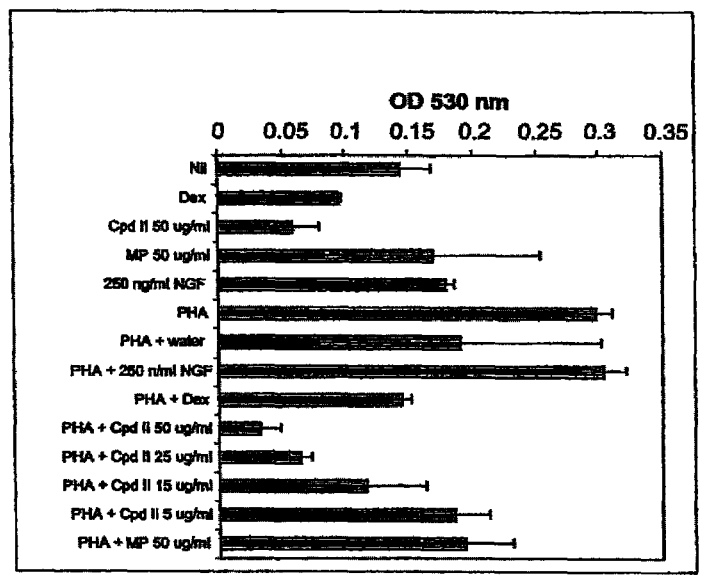
FIGS. 5A-B are graphs of OD at 530 nm for various additives to PBL cultures stimulated with 2 µg/ml and 5 µg/ml PHA, respectively.
Figure 5B:
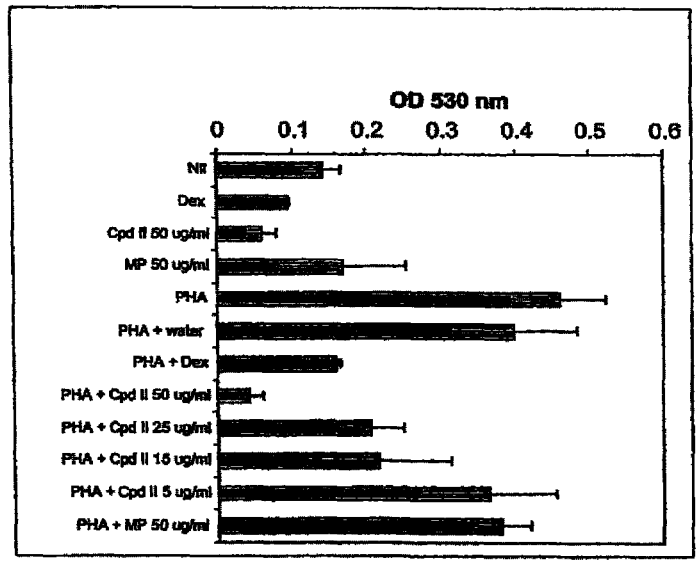

At the end of this incubation, cell proliferation was determined as described in Example 1. The results are presented in FIGS. 5A-B. As can be seen from FIGS. 5A-B, the compound of formula II (Cpd. II) and dexamethasone (Dex) significantly inhibited the proliferation of PBL, both unstimulated and stimulated with PHA, whereas methylphenidate (MP) did not.

The release of cytokines by the PBL was also measured by culturing the PBL in 1 ml tubes, at 1×10$^6$ cells per ml, with 15 µg/ml and 50 µg/ml of the compound of formula II or 10 µM dexamethasone at 37° C., 5% $CO_2$ for 24 hours. After this incubation, PHA was added to give a final concentration of 5 µg/ml, and the cells were incubated for an additional 72 hours at 37° C., 5% $CO_2$. All cultures were performed in triplicate. Cells were then removed by centrifugation at 1000 rpm for 10 minutes.

Figure 6:
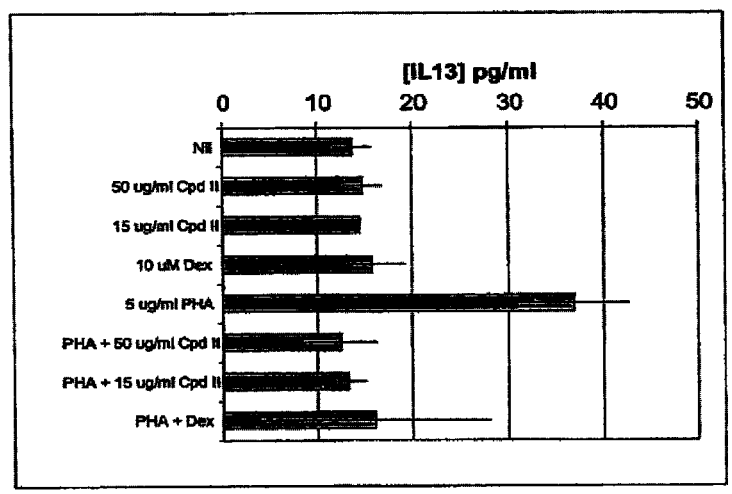
FIG. 6 is a graph of concentration of IL-13 for various additives to PBL cultures stimulated with 5 µg/ml PHA.

The supernatants were collected, and the concentrations of IL-13 and tumor necrosis factor alpha (TNFα) in the supernatants were measured by ELISA. The IL-13 ELISA was performed as described in Example 2. The results are presented in FIG. 6. As can be seen in FIG. 6, the compound of formula II (Cpd. II) and dexamethasone (Dex) significantly inhibited the release of IL-13 from the PHA-stimulated PBL.

TNFα is a proinflammatory cytokine made by activated T-cells and other cells. TNFα causes endothelial cells to express adhesion molecules and may play a role in the recruitment of immune cells to the sites of inflammation. TNFα has been detected in multiple solid and hemotologic malignancies. A number of different intracellular signals are induced by TNFα, including signals for both cells survival through NFκB and AP-1 and cell death through caspase activation. NFκB is a key regulator of cell survival and promoter of carcinogenesis in multiple tumor types.

Figure 7:
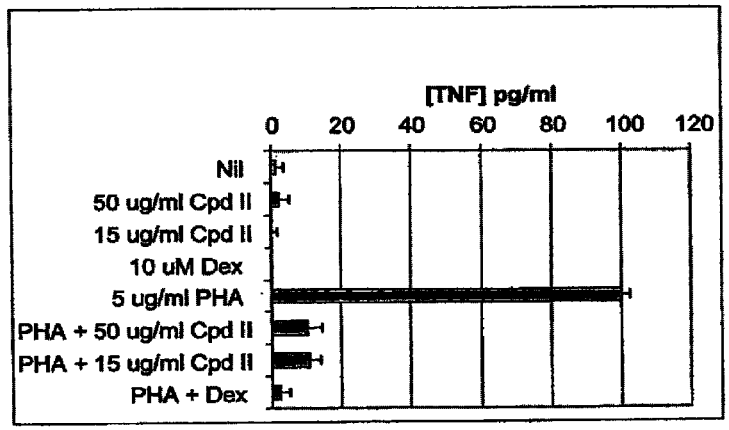
FIG. 7 is a graph of concentration of TNFα for various additives to PBL cultures stimulated with 2 µg/ml PHA.

The TNFα ELISA was performed as described in Example 2 using matched pair antibodies from Pierce Endogen (2 µg/ml for the coating antibody and 250 ng/ml for the second antibody). The results are presented in FIG. 7. As can be seen in FIG. 7, the compound of formula II (Cpd. II) and dexamethasone (Dex) significantly inhibited the release of TNFα from PHA-stimulated PBL.

The cells were further analyzed by flow cytometry Annexin was used to determine populations of dead or dying cells. Anti-CD69 antibody was used to establish the level of cellular activation. Antibody to T-cell receptor αβ (TCR) was also used. Recombinant Annexin 5 (PE and FITC conjugates) and the antibodies were all purchase from Caltag (Burlingham, Calif.) and used following the manufacturer's recommendations. The following results were observed.

Cell Death:

Annexin staining of TCR-positive cells increased from 7.3% (background) to 45% and 23% with 50 µg/ml and 15 µg/ml of the compound of formula II, respectively, signifying an increase in cell death in the T-cell population. Stimulation with PHA at 5 µg/ml increased the annexin staining of TCR-positive cells to 67%. This indicates that PHA can also induce cell death in the T-cell population. Cell death decreased slightly as a result of treatment with PHA plus 15 µg/ml of the compound of formula II (62% of the TCR-positive cells stained for annexin with PHA and IMM 0001 versus 67% with PHA alone). PHA plus 50 µg/ml of the compound of formula II caused 87% cell death in the TCR-positive subset of cells as seen by annexin staining. These results show that the higher 50 µg/ml concentration of the compound of formula II caused significant death of T-cells, whereas the lower 15 µg/ml concentration did not. Dexamethasone rescued the PHA-induced increase in annexin staining of TCR-positive cells (decreased from 84% to 48%), demonstrating that the control compound is working properly.

Activation of T-Cells:

CD69+TCR staining (activated T cells) was not detected in any of the controls (nil, compound of formula II alone and dexamethasone alone). PHA increased CD69+TCR staining to 84%. Only PHA caused T-cell activation as detectable by increased CD 69 staining CD69+TCR staining of PHA-stimulated cells dropped from 84% to 54% with 50 µg/ml of the compound of formula II and to 64% with 15 µg/ml of the compound of formula II. Dexamethasone was less effective than the compound of formula II at reducing the CD69+TCR staining of PHA-stimulated cells. Thus, the compound of formula II is more effective at decreasing T-cell activation than dexamethasone, a potent anti-inflammatory.

Example 4

Whole blood was drawn from GR-192, a normal human volunteer, and processed as described in Example 1 to give heat-inactivated serum and PBL. Then, GR-192's PBL were cultured in 1 ml tubes, at 1.3×10$^6$ cells per ml, with 15 µg/ml of the compound of formula II (in culture medium made using 10% heat-inactivated GR-192 serum) or 10 µM dexamethasone, at 37° C., 5% $CO_2$ for 24 hours. After this incubation, PHA was added to give a final concentration of 2 µg/ml, and the cells were incubated for an additional 96 hours at 37° C., 5% $CO_2$. All cultures were performed in triplicate. Cells were then removed by centrifugation at 1000 rpm for 10 minutes, and the culture medium collected.

Release of IL-8 into the culture medium was measured by ELISA. IL-8 is a proinflammatory cytokine and a potent chemoattractant and activator of neutrophils. It has also been reported to be a chemoattractant and activator of T-lymphocytes and eosinophils. IL-8 is produced by immune cells (including lymphocytes, neutrophils, monocytes and macrophages), fibroblasts and epithelial cells. IL-8 has potent angiogenic activity.

To perform the ELISA, matched pairs of antibodies against human IL-8 were purchased from Pierce Biotechnology and Biosource, respectively. ELISA strip well plates were coated with 2 µg/ml of antibody to IL-8 (in phosphate-buffered saline (PBS)) overnight at room temperature. The plates were then blocked using a 4% BSA solution in PBS for one hour, followed by the addition of 50 µA of experimental culture medium per well in duplicate. The plates were incubated at room temperature for one hour and then washed using 50 mM Tris pH 8.0 with 0.1% Tween 20. Then, solutions of 100 ng/ml biotinylated second antibody to IL-8 were made in blocking buffer, and 100 µl were added per well. The plates were incubated for 1 hour and washed again. A 1:8000 dilution of Strepavidin HRP (Pierce Biotechnology) conjugate was made in blocking buffer, and 100 µl were added to the wells and incubation continued for 30 minutes. A final wash step was performed, after which 100 µl Pierce Biotechnology TMB substrate were added to each well. Color was developed for 30 minutes and stopped by adding 100 µl 0.18 N $H_2SO_4$. OD was determined using microplate reader with a 450 nm filter.

Figure 8:
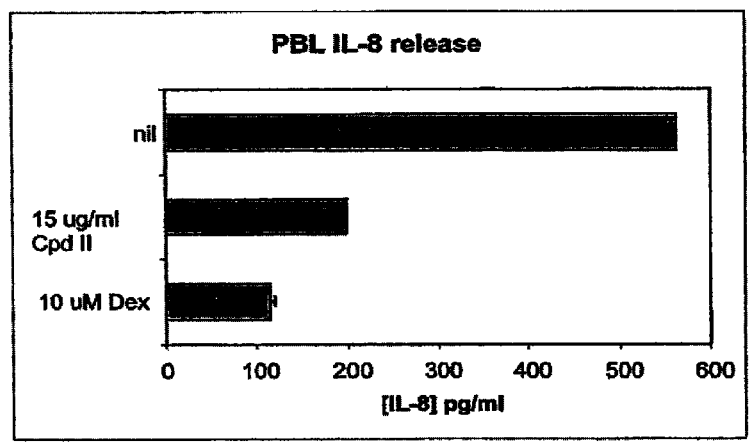
FIG. 8 is a graph of concentration of IL-8 for various additives to PBL cultures stimulated with 2 µg/ml PHA.

The results are shown in FIG. 8. As can be seen, the compound of formula II (Cpd. II) and dexamethasone (Dex) significantly inhibited IL-8 release induced by PHA.

A CD4-positive human T-lymphocyte cell line (TRiPS), which was isolated from an influenza-immunized donor and is specific for hemagglutinin peptide 307-319, was stimulated for passage using approximately $4 \times 10^5$ cells on day 18-20 after a previous stimulation. Cells were washed once in cold Iscove's Modified Dulbecco Minimal Essential Medium (IMDM, Sigma) plus 10% fetal bovine serum (FBS; American Type Culture Collection (ATCC)) and resuspended in 1.0 ml cold IMDM medium containing a 1:500 dilution of anti-CD3 monoclonal antibody OKT3 (prepared from mouse ascites fluid). Cells were incubated with antibody for 30 minutes on ice, then washed with cold medium without FBS and combined with approximately $2 \times 10^6$ 4000R-irradiated normal human donor peripheral blood leukocytes (PBL), as feeder cells, in medium plus 50 U/ml human IL-2 (Xenometrix). Cultures were expanded by the addition of fresh IMDM medium with FBS plus IL-2 on day 3. Day of culture is measured from the day of stimulation with OKT3. Cells can be used for experiments starting on day 7 (at maximum proliferation), typically on day 14 (most sensitive to re-stimulation) and up until day 21 (resting cells approaching senescence).

Activation experiments were performed by withdrawing an aliquot of cells and washing twice with warmed (37° C.) IMDM. For each specific assay, $2 \times 10^5$ viable cells were pre-incubated in a total volume of 0.9 ml warmed IMDM medium containing 15 µg/ml of the compound of formula II or 10 µM dexamethasone for 15 minutes at 37° C. An aliquot of $2 \times 10^5$ CD3/CD28 Dynabeads (Dynal), as activating stimulus, in 0.1 ml warmed IMDM was then added, and the cultures incubated 24 hours at 37° C. Supernatants of the cell cultures were harvested after pelleting the cells by centrifugation.

Cytokine content was assayed by specific IL-8 ELISA as described above. It was found that the compound of formula II had no effect on IL-8 production by the TRiPS cell line.

Example 5

THP-1 is a monocyte cell line obtained from American Type Culture Collection (ATCC) (catalog no. TIB-202). THP-1 cells were placed in medium (RPMI containing 10% FCS and 8 ng/ml monothioglycerol (obtained from Sigma)) at a concentration of 250,000 cells per ml and incubated with 15 µg/ml of compound of formula II or 10 µM dexamethasone for one hour at 37° C. and 5% $CO_2$. After 1 hour, lipopolysaccharide (LPS) (obtained from Sigma) was added to the cultures to give a final concentration of 200 ng/ml, and the cells were then incubated for an additional 4 hours or for an additional 24 hours. After the incubation, the cells were centrifuged, and the supernatants were collected. The concentrations of IL-8 and TNFα in the supernatants were determined by ELISA.

The concentrations of IL-8 in the supernatants were determined by ELISA performed as described in Example 4. The results are presented in Table 1 below. As can be seen in Table 1, the compound of formula II (Cpd. II) and dexamethasone (Dex) significantly inhibited the release of IL-8 from the LPS-stimulated monocytes.

The TNFα ELISA was performed as described in Example 2. The results are presented in Table 2 below. As can be seen in Table 2, the compound of formula II (Cpd. II) and dexamethasone (Dex) significantly inhibited the release of TNFα from the LPS-stimulated monocytes.

TABLE 1

| Sample | Time Of Incubation | Mean IL-8 Concentration (pg/ml) | % Inhibition |
| --- | --- | --- | --- |
| Control (no additives) | 4 hours | 75.96 ± 12.73 | N/A |
| LPS | 4 hours | 2844.60 ± 180.55 | N/A |
| LPS + Cpd II | 4 hours | 2185.00 ± 78.30 | 23% |
| LPS + Dex | 4 hours | 2102.18 ± 52.20 | 26% |
| Control (no additives) | 24 hours | 46.09 ± 22.42 | N/A |
| LPS | 24 hours | 6653.20 ± 193.18 | N/A |
| LPS + Cpd II | 24 hours | 4490.20 ± 264.46 | 33% |
| LPS + Dex | 24 hours | 2300.00 ± 283.41 | 66% |

TABLE 2

| Sample | Time Of Incubation | Mean TNFα Concentration (pg/ml) | % Inhibition |
| --- | --- | --- | --- |
| Control (no additives) | 24 hours | 1.415 ± 1.464 | N/A |
| LPS | 24 hours | 138.655 ± 0.601 | N/A |
| LPS + Cpd II | 24 hours | 65.370 ± 0.891 | 53% |
| LPS + Dex | 24 hours | 94.759 ± 8.755 | 32% |

Example 6

The Jurkat T-lymphocyte leukemia cell line was obtained from American Type Culture Collection (ATCC), Rockville, Md. (catalog no. TIB-152). Jurkat cells, at $1 \times 10^5$ cells/ml, were cultured at 37° C. and 5% $CO_2$ in IMDM medium (ATCC) with 10% FCS for 72 hours with 7.5 µg/ml or 15 µg/ml of the compound of formula II (Cpd II). Following the incubation, the cells were washed with Hepes buffered saline, split into three equal volumes, and then incubated with 5 µM ethidium bromide dimer-1 (ETH-D1) (obtained from Molecular Probes) and 5 µM calcein AM solution (obtained from Promega) for one hour at 37° C. and 5% $CO_2$ in 96-well culture plates to assay for cell viability. The fluorescence in each well was measured using a plate reader at excitation/emission 485/530 nm and 530/645 nm. Relative percentage of dead to live cells was calculated by dividing ETH-D1 fluorescence by calcein AM fluorescence. The results are shown in Table 3 below.

TABLE 3

| Sample | Relative Percentage Dead/Live |
| --- | --- |
| Control (no additives) | 20.85% ± 1.42% |
| 7.5 µg/ml Cpd II | 16.74% ± 2.15% |
| 15 µg/ml Cpd II | 40.79% ± 1.81% |

Example 7

Passage 4 (i.e., four cell population doublings) human umbilical vein endothelial cells (HUVECs), human source lot number 9713 (obtained from ATCC) in 1 ml of endothelial growth medium-2 (EGM-2) (obtained from Cambrex) were mixed with 30 µg of the compound of formula II (Cpd II) in endothelial basal medium-2 (EBM-2) (Cambrex) or 30 µg methylphenidate (MP) in EBM-2. Water (vehicle for the two test compounds) was used as a control, and the PI3 kinase inhibitor, LY 294002 (Sigma), at 50 µM, was included as a positive control. Then, the cells were seeded at 10,000 cells/well into the wells of a plate contained in a tube formation assay kit obtained from BD Biosciences, Rockville, Md. The wells of the plate contained an extracellular matrix protein gel. Fetal calf serum (FCS) (ATCC) was added to a final concentration of 5% to initiate tube formation. Then, the plates were incubated for 18 hours at 37° C. and 5% $CO_2$. Following the incubation, the plates were photographed with a digital camera attached to an inverted microscope (Olympus IMT-2 set at a phase contrast (PC) of 10).

When endothelial cells are cultured on extracellular matrix protein gels in the presence of angiogenic signals, they arrange themselves into structures loosely resembling capillary blood vessels. To establish the basal tube formation for this assay, cells were treated with the same amount of water as present in the solutions of Cpd II and MP. This treatment produced a lattice of endothelial cell structures with multiple branch points. Treatment with Cpd II and LY 294002 reduced the amount of branching and cellular interaction in the wells, leaving the cells in isolated clusters. MP had no observable effect on the ability of the endothelial cells to organize into structures resembling capillary blood vessels. These data indicate that Cpd II, but not MP, interferes with this step of angiogenesis.

Example 8

Passage 4 HUVECs, lot number 9713, in either EGM-2 plus 50 ng/ml vascular endothelial growth factor (VEGF) (obtained from Sigma) or in EGM-2 complete medium (containing 2% FCS, hydrocortisone, human fibroblast growth factor B, VEGF, recombinant insulin-like growth factor-1, ascorbate, human epithelial growth factor, gentamycin and heparin) (obtained from Cambrex) were put into the wells of a 96-well tissue culture plate at 5,000 cells/well. The following additives were added to the cells: water (vehicle control); 5 μg/ml of the compound of formula II (Cpd II); 15 μg/ml Cpd II; or 30 μg/ml of Cpd II. After 48 hours of culture at 37° C. and 5% $CO_2$, cell proliferation was evaluated by the Promega cell titer assay as described in Example 1, except that the plates were incubated for only 2 hours after addition of the Promega cell titer reagent.

The results are shown in Table 4 below. As can be seen from Table 4, Cpd II reduced the number of cells detected in the wells in a dose-dependent manner. The reductions seen with 15 μg/ml Cpd II and 30 μg/ml Cpd II were statistically significant. Since wells with no growth factors were not included, it is not possible to determine if the reductions in cell numbers seen with Cpd II are due to inhibition of proliferation or a cytotoxic effect.

TABLE 4

| Sample | Medium | Mean OD at 530 nm | p value (versus vehicle control) |
|---|---|---|---|
| Control (no additives) | EGM-2 + VEGF | 0.141 ± 0.004 | N/A |
| Vehicle control (water added) | EGM-2 + VEGF | 0.224 ± 0.011 | N/A |
| 5 μg/ml Cpd II | EGM-2 + VEGF | 0.189 ± 0.014 | 0.0324 |
| 15 μg/ml Cpd II | EGM-2 + VEGF | 0.132 ± 0.022 | 0.0069 |
| 30 μg/ml Cpd II | EGM-2 + VEGF | 0.046 ± 0.012 | 0.0003 |
| Control (no additives) | EGM-2 + growth factors | 0.243 ± 0.002 | N/A |
| Vehicle control (water added) | EGM-2 + growth factors | 0.299 ± 0.011 | N/A |
| 5 μg/ml Cpd II | EGM-2 + growth factors | 0.271 ± 0.022 | 0.1131 |
| 15 μg/ml Cpd II | EGM-2 + growth factors | 0.239 ± 0.019 | 0.0283 |
| 30 μg/ml Cpd II | EGM-2 + growth factors | 0.066 ± 0.003 | 0.0001 |

Example 9

HepG2 is a human hepatic cancer cell line, which was obtained from ATCC. HepG2 cells were grown to confluence in 25 $cm^2$ flasks in IMDM medium containing 10% FCS. Then, the cells were trypsinized as follows. The medium in each flask was aspirated and replaced with 5 ml of 0.025% trypsin/EDTA (Cambrex). The cells were monitored on a microscope until they no longer adhered to the flasks. Then, 5 ml of trypsin neutralizing solution (TNS) (Cambrex) were added to each flask to stop the reaction. The cell suspension was centrifuged at 1000 rpm for 10 minutes, and the supernatants were aspirated. The cells were reconstituted in fresh medium and counted. Then, 4 ml of the cell suspension in medium containing at $1.22 \times 10^6$ cells/ml were mixed with an additional 1 ml of medium. Next, 0.5 ml/well of the resulting cell suspension was added to wells in a 24-well culture plate (about 500,000 cells/well). The cells were treated as indicated in Table 5 below and incubated for 24 hours at 37° C., with or without 5% $CO_2$. The supernatants were removed from the wells and centrifuged to remove debris. Next, the supernatants were analyzed for erythropoietin (EPO) production. EPO was measured by ELISA using a kit obtained from R & D Systems, Minneapolis, Minn. (catalog no. DE900) following the manufacturer's instructions.

The results are shown in Table 5 below. As can be seen from Table 5, Cpd II significantly inhibited the release of EPO from the HepG2 cells. A decrease in EPO would have an inhibitory effect on angiogenesis. A viability assay was not performed, but the morphology of the cells appeared normal based on microscopic analysis.

TABLE 5

| Treatment | Mean Units/ml EPO | p value versus hypoxia alone |
|---|---|---|
| Control (no treatment) | 74.90 ± 2.65 | N/A |
| Hypoxia (5% $CO_2$) | 108.39 ± 2.81 | N/A |
| Hypoxia + 15 μg/ml Cpd II | 71.60 ± 2.01 | 0.005 |
| Hypoxia + 25 μM LY 294002 | 52.99 ± 1.04 | 0.016 |

Example 10

Passage 4 HUVECs, lot number 9713, were put into the wells of a 48-well tissue culture plate at 20,000 cells/well in 500 μl of EGM-2 complete medium (but without serum or ascorbate) supplemented with ITSS (insulin, transferrin and sodium selenite) (obtained from Sigma). Also, passage 4 HUVECs, human source lot number 7016 (obtained from ATCC), were put into the wells of a 48-well tissue culture plate at 20,000 cells/well in 500 μl of EGM-2 complete medium (but without serum or ascorbate) supplemented with ITSS. The following additives were added to the cells: water (vehicle control) and 15 μg/ml of the compound of formula II (Cpd II). After incubation for 1 hour at 37° C. and 5% $CO_2$, LPS was added to give a final concentration of 200 ng/ml, and the cells were incubated overnight at 37° C. and 5% $CO_2$. After this incubation, the supernatants were collected, and the amount of IL-8 in the supernatants determined by ELISA as described in Example 4.

The results are shown in Table 6 below. As can be seen in Table 6, Cpd II complete eliminated IL-8 release by the 7016 HUVECs and decreased IL-8 release by 90% in the 9713 HUVECs.

TABLE 6

| Cells | Treatment | IL-8 (pg/ml) |
|---|---|---|
| 7016 HUVECs | Control (LPS only) | 53.3 |
| 7016 HUVECs | LPS + 15 µg/ml Cpd II | Below detection |
| 9713 HUVECs | Control (LPS only) | 485.0 |
| 9713 HUVECs | LPS + 15 µg/ml Cpd II | 49.8 |

Example 11

Passage 4 HUVECs, human source lot number 8710 (obtained from ATCC), were put into the wells of a 24-well tissue culture plate at 5,000 cells/well in EGM-2 medium and cultured for 72 hours at 37° C. and 5% $CO_2$. Then, the medium was replaced with fresh medium, and the following additives were added to the cells: water (vehicle control); 1 µg/ml, 5 µg/ml, 10 µg/ml, 15 µg/ml or 30 µg/ml of the compound of formula II (Cpd II); 15 µg/ml methylphenidate (MP); 10 µM LY 294002; or 10 µM dexamethasone (Dex). After incubation for 1 hour at 37° C. and 5% $CO_2$, TNFα (Pierce) was added to give a final concentration of 10 ng/ml, and the cells were incubated for an additional 18 hours at 37° C. and 5% $CO_2$. After this incubation, the supernatants were collected, and the amount of IL-8 in the supernatants determined by ELISA as described in Example 4.

The results are shown in Table 7 below. As can be seen in Table 7, Cpd II decreased IL-8 release stimulated by TNFα in a dose-dependent manner, although there did appear to be some cell death caused by the highest dose (30 µg/ml). Dex and MP slightly decreased IL-8 release and LY 294002 significantly decreased IL-8 release.

TABLE 7

| Treatment | Mean IL-8 (pg/ml) | p value | % inhibition |
|---|---|---|---|
| No additives | 207.15 ± 66.17 | | |
| 30 µg/ml Cpd II | 0 | | |
| 15 µg/ml Cpd II | 400.35 | | |
| 10 ng/ml TNFα | 34695 ± 301.9 | | |
| 10 ng/ml TNFα + water | 35572 ± 967.74 | | |
| 10 ng/ml TNFα + 30 µg/ml Cpd II | 4829.8 ± 214.13 | | 86.93% |
| 10 ng/ml TNFα + 15 µg/ml Cpd II | 20817 ± 674.63 | 0.002 | 41.72% |
| 10 ng/ml TNFα + 10 µg/ml Cpd II | 22050 ± 727.27 | 0.003 | 38.24% |
| 10 ng/ml TNFα + 5 µg/ml Cpd II | 34482 ± 2127.22 | 0.124 | 3.08% |
| 10 ng/ml TNFα + 1 µg/ml Cpd II | 53657 ± 3935.18 | 0.011 | (−51.1%) |
| 10 ng/ml TNFα + 15 µg/ml MP | 30183 ± 3448.01 | 0.051 | 15.24% |
| 10 ng/ml TNFα + 10 µM LY 294002 | 9196.1 ± 150.97 | | 74.58% |
| 10 ng/ml TNFα + 10 µM Dex | 35952 ± 2197.14 | 0.072 | 6.88% |

Example 12

The transcription factor NFκB (nuclear factor κB) is implicated in the regulation of the expression of a wide variety of genes that code for mediators of the immune, acute phase and inflammatory responses. NFκB is a key regulator of cell survival and promoter of carcinogenesis. There are five subunits of the NFκB family in mammals: p50, p65 (RelA), c-Rel, p52 and RelB. The p50/p65 heterodimers and the p50 homodimers are the most common dimers found the NFκB signaling pathway. NFκB can be activated by a number of stimuli, including components of bacterial cell walls, such as lipopolysaccharide, or inflammatory cytokines, such as TNFα or IL-1β.

Activator protein-1 (AP-1) is a transcription factor that is activated during the cell cycle to promote cell survival, differentiation and adaptive responses. AP-1 proteins play a role in the expression of many genes involved in proliferation and cell cycle progression. For instance, cell transformation by oncogenes that function in the growth factor signal transduction pathway, such as ras, rasF and mek, results in a high increase in AP-1 component protein expression. Therefore, AP-1 regulated genes support the invasive process observed during malignancy and metastasis. AP-1 belongs to a large family of structurally related transcription factors that includes ATFI-4, c-Fos, c-Jun, c-Myc and C/EBP. AP-1 is composed of a mixture of heterodimeric complexes of proteins derived from the Fos and Jun families, including c-Fos, FosB, Fra-1, Fra-2, c-Jun, JunB and JunD. Primarily, AP-1 dimers bind to DNA on a TPA-response element (TRE). AP-1 expression is induced by multiple stimuli such as serum, growth factors, phorbol esters, oncogenes, cytokines of the TGF-β, TNF and interferon families, neuronal depolarization and cellular stress.

Passage 5 HUVECs, human source lot number 8750, were grown to confluence in 25 $cm^2$ flasks in EGM-2 medium. The following additives were added to the flasks (total volume of 5 ml/flask) in EGM-2 medium containing 2% FCS, GA1000 (gentamycin), heparin and ascorbic acid (all from Cambrex): 1 µg/ml of the compound of formula II (Cpd II); 5 µg/ml Cpd II; 15 µg/ml of Cpd II; 15 µg/ml methylphenidate (MP); or 10 µM LY 294002. The flasks were incubated overnight at 37° C., 5% $CO_2$. After this incubation, VEGF was added to give a final concentration 10 ng/ml, and the flasks were incubated for an additional 30 minutes.

Then, the amount of NFκB was determined using a TransAM™ NFκB p65/NFκB p50 Transcription Factor Assay Kit and a Nuclear Extract Kit from Active Motif North America, Carlsbad, Calif., according to the manufacturer's instructions. Briefly, a nuclear extract of the cells was prepared using the Nuclear Extract Kit. Then, the nuclear extract was added to the wells of the 96-well plate of the TransAM™ kit. Oligonucleotide containing an NFκB consensus binding site was immobilized in the wells, and the activated NFκB contained in the nuclear extract was bound to the oligonucleotide. Then, an antibody directed against the NFκB p65 or p50 subunit was added, and the NFκB complex bound to the oligonucleotide was detected. A secondary antibody conjugated to horseradish peroxidase (HRP) was next added to provide a colorimetric readout that was quantified by spectrophotometry (measurement at 450 nm).

The amount of c-Jun was determined using a TransAM™ AP-1 Family Transcription Factor Assay Kit and a Nuclear Extract Kit from Active Motif North America, Carlsbad, Calif., according to manufacturer's instructions. Briefly, a nuclear extract of the cells was prepared using the Nuclear Extract Kit. Then, the nuclear extract was added to the wells of a 96-well plate in which oligonucleotide containing a TPA-responsive element (TRE) was immobilized. Activator protein-1 (AP-1) dimers contained in the nuclear extract were bound to this oligonucleotide and were detected using an antibody specific for c-Jun. A secondary antibody conjugated to horseradish peroxidase (HRP) was next added to provide a colorimetric readout that was quantified by spectrophotometry (measurement at 450 nm).

The results are shown in Tables 8 and 9 below. As can be seen from Table 8, VEGF treatment of HUVECs caused almost a doubling of activated NFκB as detected by the TransAM assay. Cpd II at 15 µg/ml and 5 µg/ml reduced the amount of activated NFκB back to basal levels. As can be seen from Table 9, VEGF treatment of HUVECs caused an increase of c-Jun. Cpd II at 15 µg/ml and 5 µg/ml completely eliminated the increase in the amount of c-Jun.

TABLE 8

| Sample | Mean OD 450 nm (NFκB) |
|---|---|
| Control (no additives) | 0.070 ± 0.002 |
| VEGF only | 0.111 ± 0.007 |
| VEGF + 15 µg/ml Cpd II | 0.060 ± 0.008 |
| VEGF + 5 µg/ml Cpd II | 0.065 ± 0.010 |
| VEGF + 1 µg/ml Cpd II | 0.097 ± 0.013 |
| VEGF + 15 µg/ml MP | 0.093 ± 0.011 |
| VEGF + 10 µM LY 294002 | 0.138 ± 0.008 |

TABLE 9

| Sample | Mean OD 450 nm (c-Jun) |
|---|---|
| Control (no additives) | 0.204 ± 0.016 |
| VEGF only | 0.261 ± 0.013 |
| VEGF + 15 µg/ml Cpd II | 0.204 ± 0.010 |
| VEGF + 5 µg/ml Cpd II | 0.185 ± 0.025 |
| VEGF + 1 µg/ml Cpd II | 0.221 ± 0.008 |
| VEGF + 15 µg/ml MP | 0.230 ± 0.016 |
| VEGF + 10 µM LY 294002 | 0.340 ± 0.020 |

Example 13

Passage 8 (human iliac artery endothelial cells (HIAECs) (obtained from ATCC; catalog no. CC-2545) were grown to confluence in 25 cm$^2$ flasks in EGM-2 medium. Eighteen hours prior to the experiment, the medium was replaced with EGM-2 medium containing 0.1% FCS plus heparin, GA1000 (gentamycin) and bovine pituitary extract (all from Cambrex) to place the cells in a resting state. To perform the experiment the medium was aspirated from the flasks, and the following additives were added to the flasks in fresh medium (total volume of 5 ml/flask): 15 µg/ml of the compound of formula II (Cpd II) or 10 µM LY 294002. The flasks were incubated 2 hours at 37° C., 5% CO$_2$. After this incubation, VEGF or TNFα was added to give a final concentration 10 ng/ml, and the flasks were incubated for an additional 30 minutes. Then, the amount of NFκB was determined using a TransAM™ NFκB p65/NFκB p50 Transcription Factor Assay Kit and a Nuclear Extract Kit from Active Motif North America, Carlsbad, Calif., as described in Example 12.

The results are shown in Table 10 below. As can be seen from Table 10, TNFα treatment of HUVECs caused an extremely large increase in the amount of activated NFκB as detected by the TransAM assay. Cpd II at 15 µg/ml reduced the amount of activated NFκB about 82%. The treatment with VEGF did not result in as large an increase in activated NFκB as achieved with TNFα, but the increased amount was reduced 70% by Cpd. II.

TABLE 10

| Sample | Mean OD 450 nm (NFκB) | Percent Inhibition |
|---|---|---|
| Control (no additives) | 0.174 ± 0.004 | |
| TNFα only | 0.881 ± 0.021 | |
| TNFα + 15 µg/ml Cpd II | 0.302 ± 0.003 | 81.89% |
| TNFα + 10 µM LY 294002 | 0.810 ± 0.007 | 10.04% |
| VEGF only | 0.220 ± 0.007 | |
| VEGF + 15 µg/ml Cpd II | 0.066 ± 0.005 | 70.00% |

Example 14

Day 18 TRiPS cells, 1×10$^6$, were incubated for 30 minutes at 37° C., either with nothing added ("Nil"), with 1 µl CD3/CD28 Dynabeads (Dynal, Oslo, Norway) ("CD3/CD28 beads") per 100,000 cells, or with CD3/CD28 beads and 15 µg/ml of the compound of formula II (Cpd II). After the incubation, the cells were lysed in Cell-Lytic Mammalian Cell Extraction Reagent (Sigma). After centrifugation to pellet cellular debris, the supernatants (cell extracts) were obtained.

The cell extracts (supernatants) were then analyzed using a Custom AntibodyArray™ manufactured by Hypromatrix Inc., Worcester, Mass., following the manufacturer's instructions. The Custom AntibodyArray™ is a nylon membrane blotted with antibodies to the proteins listed below. Briefly, the cell extracts were incubated with duplicate Custom AntibodyArray™'s for 2 hours at room temperature with slow shaking, followed by three washes with Tris buffer (150 mM NaCl, 25 mM Tris, 0.05% Tween-20, pH 7.5). HRP-labeled antibodies specific for phosphorylated-tyrosine, phosphorylated-serine and phosphorylated-threonine in Tris buffer were added, and the arrays incubated for 2 hours. After three more washes with Tris buffer, a peroxidase-reactive luminescent substrate was added. The arrays were visualized by exposure to X-ray film. Densitometry of the X-ray films was measured by scanning and computer analysis. The results are summarized in Table 11 below.

TABLE 11

| Protein | Effect of Cpd II on the protein in CD3/CD28 stimulated TRiPS cells |
|---|---|
| RAP1 | Activated |
| RAP2 | Activated |
| JAK2 | Activated |
| STAT4 | Activated |
| STAT5b | Activated |
| PI3kinaseP85 | Activated |
| MEK1 | Decreased level to below basal levels (Nil control) |
| JNK1 | Decreased level back to basal levels (Nil control) |
| JNK2 | Decreased level back to basal levels (Nil control) |
| JNK3 | Decreased level back to basal levels (Nil control) |
| MEKK1 | Decreased level back to basal levels (Nil control) |
| IkB-β | Decreased level back to basal levels (Nil control) |
| IkB-r | Decreased level back to basal levels (Nil control) |
| IL-2 | Decreased level back to basal levels (Nil control) |
| IL-4 | Decreased level back to basal levels (Nil control) |
| IL-7y | Decreased level back to basal levels (Nil control) |
| 14-3-3 | Slightly decreased the level |
| STAT6 | Slightly decreased the level |
| IkB-ε | Slightly decreased the level |
| IkB-α | Slightly decreased the level |
| VAV | No effect |
| STAT2 | No effect |

Example 15

Cells of the MC/9 murine fibroblast cell line (obtained from ATCC, catalog no. CRL-8305) were placed into the wells of a 96-well tissue culture plate at 25,000 cells/well. The culture medium was Delbecco's Modified Eagle's Medium (DMEM) (obtained from Cambrex) containing 10% FCS. Nil control wells contained no additives. The remaining wells contained either 25 ng/ml murine nerve growth factor (NGF) (obtained from Upstate Biotechnology, Lake Placid, N.Y.) or 25 ng/ml NGF and 5% TSTIM (a culture supplement prepared from rats and containing concanavalin A which was obtained from BD Biosciences). In addition, the following additives were added to the cells: water (vehicle control); 5 µg/ml of the compound of formula II (Cpd II); 15 µg/ml Cpd II; or 30 µg/ml of Cpd II. After 72 hours of culture at 37° C. and 5% $CO_2$, cell proliferation was evaluated by the Promega cell titer assay as described in Example 1. The results are shown in Table 12 below.

TABLE 12

| Additive | Mean OD 530 nm |
|---|---|
| No additives | 0.058 ± 0.008 |
| NGF | 0.116 ± 0.029 |
| NGF + water | 0.101 ± 0.022 |
| NGF + 1 µg/ml Cpd II | 0.117 ± 0.015 |
| NGF + 5 µg/ml Cpd II | 0.108 ± 0.012 |
| NGF + 15 µg/ml Cpd II | 0.049 ± 0.016 |
| NGF + TSTIM | 0.490 ± 0.047 |
| NGF + TSTIM + water | 0.365 ± 0.026 |
| NGF + TSTIM + 1 µg/ml Cpd II | 0.428 ± 0.027 |
| NGF + TSTIM + 5 µg/ml Cpd II | 0.373 ± 0.016 |
| NGF + TSTIM + 15 µg/ml Cpd II | 0.326 ± 0.024 |

Example 16

Figure 9A:
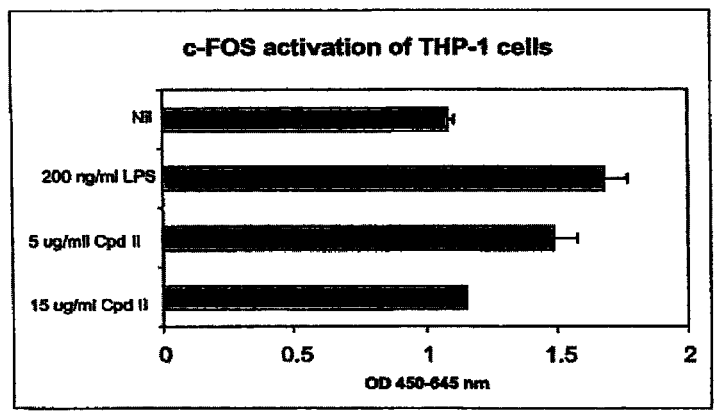
FIGS. 9A-B are graphs of OD for various additives to THP-1 monocyte cultures stimulated with lipopolysaccharide (LPS).
Figure 9B:
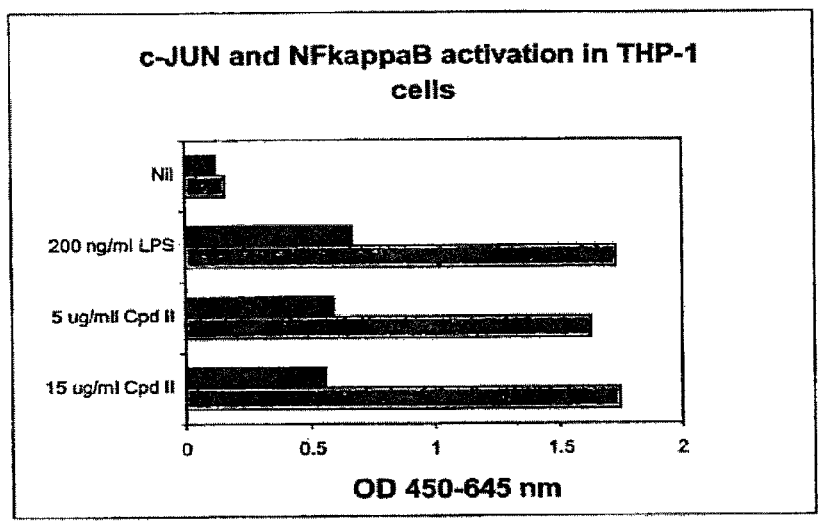

THP-1 cells were placed in medium (RPMI containing 10% FCS and 8 ng/ml monothioglycerol) at a concentration of 250,000 cells per ml and incubated with 5 µg/ml of compound of formula II (Cpd II) or 15 µg/ml of Cpd II for one hour at 37° C. and 5% $CO_2$. After 1 hour, lipopolysaccharide (LPS) was added to the cultures to give a final concentration of 200 ng/ml, and the cells were then incubated for an additional 24 hours. After the incubation, the amount of NFkB and c-Jun were determined as described in Example 12. Also, the amount of c-Fos was determined using a TransAM™ AP-1 Family Transcription Factor Assay Kit and a Nuclear Extract Kit from Active Motif North America, Carlsbad, Calif., according to manufacturer's instructions. Briefly, a nuclear extract of the cells was prepared using the Nuclear Extract Kit. Then, the nuclear extract was added to the wells of a 96-well plate in which oligonucleotide containing a TPA-responsive element (TRE) was immobilized. Activator protein-1 (AP-1) dimers contained in the nuclear extract were bound to this oligonucleotide and were detected using an antibody specific for c-Fos. A secondary antibody conjugated to horseradish peroxidase (HRP) was next added to provide a colorimetric readout that was quantified by spectrophotometry (measurement at 450 nm). The results are shown in FIGS. 9A-B.

Example 17

Day 10 TRiPS cells, 1×10$^6$, were incubated with 15 µg/ml of the compound of formula II (Cpd II) for 1 hour at 37° C. Then, the cells were incubated with CD3/CD28 beads (1 µl per 100,000 cells) (obtained from Dynal) for 10 minutes at 37° C. The cells were then lysed with a mild buffer (supplied with Pierce EZ-Detect activation kit described below) to produce cell extracts. Protein concentrations of the resulting extracts were determined by bicinchoninic acid (BCA) assay (Pierce) and placed on ice for immediate use.

Pulldown assays were performed using Pierce EZ-Detect activation kits according to the manufacturer's instructions utilizing GST-RAF-1-RBD and GST-RalGDS-RBD for Ras and RAP-1 respectively. Briefly, 400 µg total protein from each extract was combined with recombinant protein and glutathione resin and incubated at 4° C. for one hour with gentle shaking. The resin was then washed to remove unbound protein and the activated Ras and RAP-1 proteins were removed by boiling in the presence of SDS-PAGE loading dye containing reducing agent. Ras and RAP-1 western blots were performed to visualize the proteins using antibodies supplied with the kit. Densitometry of the X-ray films was done by scanning and computer analysis.

The results are shown in Table 13. As can be seen from Table 13, incubating the TRiPS cells with Cpd II resulted in very strong inhibition of Ras protein. Stimulation of the cells with CD3/CD28 beads did not increase the amount of RAP-1 protein as expected, but Cpd II also appeared to inhibit RAP-1.

TABLE 13

| Treatment | Integrated Optical Density for RAS assay | Integrated Optical Density for RAP-1 assay |
|---|---|---|
| No treatment | 66.83 | 259.27 |
| CD3/CD28 beads only | 245.91 | 213.66 |
| CD3/CD28 beads + 15 µg/ml Cpd II | 84.98 | 87.26 |

The foregoing discussion of the invention has been presented for purposes of illustration and description. The foregoing is not intended to limit the invention to the form or forms disclosed herein. Although the description of the invention has included description of one or more embodiments and certain variations and modifications, other variations and modifications are within the scope of the invention, e.g., as may be within the skill and knowledge of those in the art, after understanding the present disclosure. It is intended to obtain rights which include alternative embodiments to the extent permitted, including alternate, interchangeable and/or equivalent structures, functions, ranges or steps to those claimed, whether or not such alternate, interchangeable and/or equivalent structures, functions, ranges or steps are disclosed herein, and without intending to publicly dedicate any patentable subject matter.

What is claimed is:

1. A method of inhibiting the proliferation of a breast cancer cell, comprising contacting the cell with an effective amount of a compound of formula I:

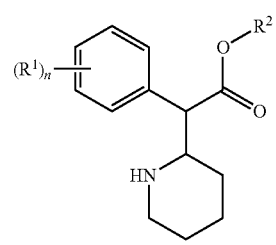

or a salt thereof, where n is 1, R1 is phenoxy, and wherein $R^2$ is hydrogen or lower alkyl.

2. The method of claim 1, wherein the breast cancer cell is a carcinoma cell.
3. The method of claim 1, wherein the compound has the structure:
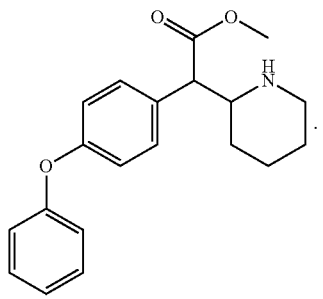 [SMILES: COC(=O)C(c1ccc(Oc2ccccc2)cc1)C1CCCCN1]
* * * * *